(12) United States Patent
Lee et al.

(10) Patent No.: US 12,076,377 B2
(45) Date of Patent: Sep. 3, 2024

(54) VARIANT SULFATASE ENZYMES WITH ENHANCED PROPERTIES

(71) Applicant: INTEGRATED MICRO-CHROMATOGRAPHY SYSTEMS, INC., Irmo, SC (US)

(72) Inventors: Lim Andrew Lee, Columbia, SC (US); Caleb Reece Schlachter, Irmo, SC (US); John Tomashek, Columbia, SC (US)

(73) Assignee: INTEGRATED MICRO-CHROMATOGRAPHY SYSTEMS, INC., Irmo, SC (US)

( * ) Notice: Subject to any disclaimer, the term of this patent is extended or adjusted under 35 U.S.C. 154(b) by 0 days.

(21) Appl. No.: 18/049,978

(22) Filed: Oct. 26, 2022

(65) Prior Publication Data
US 2023/0149519 A1 May 18, 2023

Related U.S. Application Data

(60) Provisional application No. 63/271,936, filed on Oct. 26, 2021.

(51) Int. Cl.
| | | |
|---|---|---|
| *A61K 38/46* | (2006.01) | |
| *A61K 38/16* | (2006.01) | |
| *C07K 14/00* | (2006.01) | |
| *C12N 9/16* | (2006.01) | |

(52) U.S. Cl.
CPC ............ *A61K 38/465* (2013.01); *A61K 38/16* (2013.01); *C07K 14/00* (2013.01); *C12N 9/16* (2013.01); *C12Y 301/06013* (2013.01)

(58) Field of Classification Search
CPC .... C12N 9/16; C12N 9/14; C12Y 301/06013; A61K 38/465; A61K 38/164
See application file for complete search history.

(56) References Cited

U.S. PATENT DOCUMENTS

| | | |
|---|---|---|
| 9,719,075 B2 | 8/2017 | Lee |
| 9,909,111 B2 | 3/2018 | Yang et al. |
| 9,920,306 B2 | 3/2018 | Lee |
| 2020/0040319 A1 | 2/2020 | Tomashek et al. |
| 2020/0109386 A1 | 4/2020 | Schlachter et al. |

OTHER PUBLICATIONS

Roberts et al., "Chapter 1: Introduction to enzymes, receptors and the action of small molecule drugs" in Introduction to Biological and Small Molecule Drug Research and Development—Theory and Case Studies, Ganellin et al., pp. 1-55, 2013, (Year: 2013).*
Betts et al., "Chapter 14: Amino Acid Properties and Consequences of Substitutions", in Bioinformatics for Genetics, Barnes et al., pp. 297-324 (Year: 2003).*
Uduwela et al. Supplemental Information, 2018, p. 1-26. (Year: 2018).*
Ainslie-Waldman, C. et al., "Contamination of deconjugation enzymes derived from Helix pomatia with the plant bioactive compounds 3,3'-diindolylmethane, 5-methoxypsoralen, and 8-methoxypsoralen," Food Chem. Toxicol., vol. 62: 188-193 (2013).
Ballet, C., et al., "New enzymatic and mass spectrometric methodology for the selective investigation of gut microbiota-derived metabolites," Chem. Sci. vol. 9: 6233-6239 (2018).
Barbeyron, T. et al., "Matching the Diversity of Sulfated Biomolecules: Creation of a Classification Database for Sulfatases Reflecting Their Substrate Specificity," PLoS One, vol. 11(10): e016846, 33 pages (2016).
Boltes, I. et al., "1.3 A structure of arylsulfatase from Pseudomonas aeruginosa establishes the catalytic mechanism of sulfate ester cleavage in the sulfatase family," Structure, vol. 9(6):483-491 (2001).
Cawley, L. P., et al., "Steric hindrance of the sulfatase Helix pomatia on some 17-ketosteroid sulfate conjugates," Am. J. Clin. Pathol, vol. 52: 652-655 (1969).
Chronopoulou, E. et al., "Site-saturation mutagenesis: a powerful tool for structure-based design of combinatorial mutation libraries," Curr. Protocols Protein Sci., vol. 63:26.6.1-26.6.10 (2011).
Davies, W., "The steroid sulfate axis and its relationship to maternal behavior and mental health,". J. Mol. Endocrinol, vol. 61: T199-T210 (2018).
Desdoits-Lethimonier, C. et al., "Parallel assessment of the effects of bisphenol A and several of its analogs on the adult human testis," Hum. Reprod., vol. 32(7):1465-1473 (2017).
Dierks, T., et al., "Posttranslational formation of formylglycine in prokaryotic sulfatases by modification of either cysteine or serine," J. Biol Chem., vol. 273:25560-25564 (1998).
Edwards, D. R., et al., "Catalytic Proficiency: The Extreme Case of S—O Cleaving Sulfatases," J. Am. Chem. Soc, vol. 134: 525-531 (2012).
Fitzgerald, C. et al., "Profiling Urinary Sulfate Metabolites With Mass Spectrometry," Front. Mol. Biosci., vol. 9: 829511 (2022).
Folz, R.J. et al., "Substrate specificity of eukaryotic signal peptidase. Site-saturation mutagenesis at position -1 regulates cleavage between multiple sites in human pre (delta pro) apolipoprotein A-II," J. Biol. Chem., vol. 263:2070-2078 (1988).
Forsdahl, G., et al., "Quantification of endogenous steroid sulfates and glucuronides in human urine after intramuscular administration of testosterone esters," Steroids, vol. 157, 108614 (2020).
Gomes, R. et al., "Analysis of conjugated steroid androgens: deconjugation, derivatisation and associated issues," J. Pharmaceut. Biomed. Anal., vol. 49(5):1133-1140 (2009).

(Continued)

*Primary Examiner* — Thea D' Ambrosio
*Assistant Examiner* — Claudia Espinosa
(74) *Attorney, Agent, or Firm* — Nelson Mullins Riley & Scarborough LLP; Jill Gorny Sloper, Esq.

(57) ABSTRACT

Mutated *Pseudomonas aeruginosa* sulfatase (PaS) enzymes with enhanced enzymatic activity as compared to the parental wild type enzyme are provided. The variant sulfatases of the invention advantageously allow for accurate analysis of bodily samples for the presence of drugs. Methods of using the mutated enzymes for hydrolysis of sulfate ester linkages are also provided, including with substrates such as opioids or steroids containing a sulfate ester linkage.

9 Claims, 25 Drawing Sheets

Specification includes a Sequence Listing.

(56) References Cited

OTHER PUBLICATIONS

Gomez, C., et al., "Alternative long-term markers for the detection of methyltestosterone misuse," Steroids, vol. 78: 44-52 (2013).
Hagelueken, G., et al., "The crystal structure of SdsA1, an alkylsulfatase from Psuedomonas aeruginosa, defines a third class of sulfatase," Proc. Natl. Acad. Sci. U. S. A., vol. 103:7631-7636 (2006).
James, L. C., et al., "Conformational diversity and protein evolution—a 60-year-old hypothesis revisited," Trends Biochem. Sci, vol. 28: 361-368 (2003).
Jenkinson, C., et al., "Circulating Conjugated and Unconjugated Vitamin D Metabolite Measurements by Liquid Chromatography Mass Spectrometry," J. Clin. Endocrinol. Metab., vol. 107: 435-449 (2022).
Kintses, B. et al., "Picoliter Cell Lysate Assays in Microfluidic Droplet Compartments for Directed Enzyme Evolution," Chem. Biol, vol. 19: 1001-1009 (2012).
Miton, C. et al., "Evolutionary repurposing of a sulfatase: A new Michaelis complex leads to efficient transition state charge offset," PNAS, vol. 115(31): E7293-7302 (2018).
Mueller, J. et al., "The Regulation of Steroid Action by Sulfation and Desulfation," Endocr. Rev. vol. 36:526-563 (2015).
Nakamura, T. et al., "Possible evidence of contamination by catechins in deconjugation enzymes from Helix pomatia and Abalone entrails," Biosci. Biotechnol. Biochem., vol. 75(8):1506-1510 (2011).
Pedersen, M., et al., "Optimised deconjugation of androgenic steroid conjugates in bovine urine," Food Addit. Contam, Part A 34: 482-488 (2017).
Steffens, D. et al., "Efficient site-directed saturation mutagenesis using degenerate oligonucleotides," J. Biomol. Tech., vol. 18(3):147-149 (2007).
Stevenson, B. et al., "Engineering Pseudomonas aeruginosa arylsulfatase for hydrolysis of alpha-configured steroid sulfates," Protein Eng Des Sel., vol. 35, gzac007 (2022).
Stevenson, B. J., et al., "In vitro directed evolution of enzymes expressed by E. coli in microtiter plates," Methods Mol. Biol., vol. 978: 237-249 (2013).
Stevenson, B. J., et al., "Pseudomonas aeruginosa arylsulfatase: a purified enzyme for the mild hydrolysis of steroid sulfates," Drug Test. Anal, vol. 7: 903-911 (2015).
Strahm, E. et al., "Profiling of 19-norandrosterone sulfate and glucuronide in human urine: implications in athlete's drug testing," Steroids, vol. 74: 359-364 (2009).
Stressler, T. et al., "Detection, production, and application of microbial arylsulfatases," Appl. Microbiol. Biotechnol., vol. 100(21):9053-9067 (2016).
Sun, N., et al., "Prognostic relevance of steroid sulfation in adrenocortical carcinoma revealed by molecular bhenotyping using high-resolution mass spectrometry imaging," Clin. Chem, vol. 65: 1276-1286 (2019).
Toesch, M. et al., "Microbial alkyl- and aryl-sulfatases: mechanism, occurrence, screening and stereoselectivities," Appl. Microbiol. Biotechnol., vol. 98(4):1485-1496 (2014).
Torrado, S. et al., "Urinary metabolic profile of 19-norsteroids in humans: glucuronide and sulphate conjugates after oral administration of 19-nor-4-androstenediol," Rapid Commun Mass Spectrom, vol. 22: 3035-3042 (2008).
Uduwela et al., "Enhancing the Steroid Sulfatase Activity of the Arylsulfatase from Pseudomonas aeruginosa," ACS Catal., vol. 8:8902: 24 pages (2018).
van Loo, B., et al., "Structural and mechanistic analysis of the choline sulfatase from Sinorhizobium melliloti: a class I sulfatase specific for an alkyl sulfate ester," J. Mol. Biol., vol. 430: 1004-1023 (2018).
Waller, C. C., et al., "A simple method for the small scale synthesis and solid-phase extraction purification of steroid sulfates," Steroids, vol. 92: 74-80 (2014).
Wang, F. et al.,"Advancing the analysis of terbutaline in urine samples using novel enzyme hydrolysis," Bioanalysis, vol. 10(22): (2018) 10.4155/bio-2018-0145.
Wingfield, P., "N-terminal methionine processing," Curr. Protoc. Protein Sci, vol. 88: 6.14.1-6.14.3 (2017).
Yang et al., "Development and Validation of a Novel LC-MS/MS Opioid Confirmation Assay: Evaluation of beta- glucuronidase Enzymes and Sample Cleanup Methods," J. Anal. Toxicol., vol. 40 (5):323-329 (2016).

* cited by examiner

```
  1  MSKRPNFLVI  VADDLGFSDI  GAFGGEIATP  NLDALAIAGL  RLTDFHTAST  CSPTRSMLLT
 61  GTDHHIAGIG  TMAEALTPEL  EGKPGYEGHL  NERVVALPEL  LREAGYQTLM  AGKWHLGLKP
121  EQTPHARGFE  RSFSLLPGAA  NHYGFEPPYD  ESTPRILKGT  PALYVEDERY  LDTLPEGFYS
181  SDAFGDKLLQ  YLKERDQSRP  FFAYLPFSAP  HWPLQAPREI  VEKYRGRYDA  GPEALRQERL
241  ARLKELGLVE  ADVEAHPVLA  LTREWEALED  EERAKSARAM  EVYAAMVERM  DWNIGRVVDY
301  LRRQGELDNT  FVLFMSDNGA  EGALLEAFPK  FGPDLLGFLD  RHYDNSLENI  GRANSYVWYG
361  PRWAQAATAP  SRLYKAFTTQ  GGIRVPALVR  YPRLSRQGAI  SHAFATVMDV  TPTLLDLAGV
421  RHPGKRWRGR  EIAEPRGRSW  LGWLSGETEA  AHDENTVTGW  ELFGMRAIRQ  GDWKAVYLPA
481  PVGPATWQLY  DLARDPGEIH  DLADSQPGKL  AELIEHWKRY  VSETGVVEGA  SPFLVR 536
```

VARIANT SULFATASE ENZYMES WITH ENHANCED PROPERTIES

RELATED APPLICATIONS

This application claims priority to U.S. Provisional Application No. 63/271,936, filed Oct. 26, 2021, the entire contents of which is hereby incorporated by reference.

SEQUENCE LISTING

The Sequence Listing is provided as a file entitled IMJ-016_SequenceListing_2022-10-25, created on Oct. 25, 2022, which is 233 kilobytes in size. The information in the electronic format of the sequence listing is incorporated herein by reference in its entirety.

BACKGROUND OF THE INVENTION

Urine drug testing (UDT) in clinical, forensic, and sports settings is complicated by a variety of factors. First, there are many potential targets that need to be detected. Second, multiple metabolic pathways alternately degrade and modify the targets into a further plethora of species that comprise a majority of secreted forms, primarily sulfate esters and sulfates (Morgan (1990) *Clin. Pharmacokinet.* 18: 270; Walle et al. (1996) *Clin. Rev. Allergy Immunol.* 14: 101). Third, differential ratios of secreted forms are a function of the age, health, gender, and other related aspects of the sample source. Fourth, different detection methods compatible with the different solubilities of targets and derivatives are required. These and other factors make screening even a small number of related targets a challenge for labs that perform these tests and must produce certifiable results with impactful legal and health consequences.

The practice of UDT has evolved and improved significantly over the past 50 years. Early on, the deconjugation of modified drug metabolites excreted in urine was recognized as an advantage because it reduced the number of targets that need to be detected and, likewise, reduced the number of required certified standards needed for quantitation. Initially, chemical (acid) hydrolysis was employed, which has the advantage that it removes most all excretion tags, regardless of type. However, this approach also has many downsides, including differential reaction times for different targets, side reactions that modify or degrade the targets, and a strict requirement for precise reaction conditions and protocols to ensure reproducibility. Enzyme alternatives to acid hydrolysis were quickly recognized as superior in many of these respects (Henry and Thevenet (1952) *Bull. Soc. Chim. Biol.* 34: 886).

Crude enzyme preparations from mollusk sources were used initially, but these require elevated temperature and reaction times in the hours to days (Graef et al. (1977) *Clin. Chem.* 23: 532; Romberg and Lee (1995) *J. Anal. Toxicol.* 19: 157; Yang et al. (2016) *J. Anal. Toxicol.* 40: 323). These enzymes are comprised primarily of glucuronidases, but they usually also contain arylsulfatases, which were initially regarded as a confounding variable (Nakamura et al. (2011) *Biosci. Biotechnol. Biochem.* 75: 1506; Ainslie-Waldman et al., (2013) *Food Chem. Toxicol.* 62: 188). As a result, partially purified and bacterially-expressed glucuronidases, both advertised as sulfatase-free, became preferred reagents for sample processing; the World Anti-Doping Agency (WADA) stipulates that only bacterial enzymes, and not mollusk enzymes, may be used for official anti-doping drug testing (WADA TD2018EAAS). Further efforts to improve the purity, broaden the substrate range, and increase the hydrolysis efficiency of glucuronidase enzymes have resulted in reaction times and conditions becoming shorter and simpler, thereby greatly increasing testing throughput and accuracy (U.S. Pat. Nos. 9,719,075; 9,909,111; 9,920,306; US 20200040319; US 20200109386). However, more recently it has become apparent that sulfated metabolites, generally disregarded, may also be important for certain samples or target molecules.

Clinical, forensic, and sports-related drug targets such as opioids, opiates, benzodiazepines, cannabinols, steroids, and β-agonists are partially or predominantly glucuronidated by adult humans for excretion, and this has driven the major market for glucuronidase enzymes. However, there are important exceptions. First, β-agonists and steroid hormones, prominent examples of important targets for testing in sports doping, are predominantly sulfated for excretion (Gomes et al. (2009) *J. Pharmaceut. Biomed. Anal.* 49:1133; Wang et al. (2018) *Bioanalysis* 10.4155/bio-2018-0145). This also applies for diagnosis and monitoring of steroid disorders. Second, sulfation is the primary pathway of phase II metabolism in neonates, for whom drug testing is important for establishing possible in utero exposures (Coughtrie (2015) *Drug Metab. Lett.* 9:99; Matalová et al. (2016) *Drug Metab. Rev.* 48:70). Third, there are emerging protocols in environmental testing for contaminants such as endocrine disruptors (e.g. bisphenols) and nutritional metabolites such as flavonoids that sulfatases, like glucuronidases, will likely improve by simplifying analysis and quantitation of targets (Desdoits-Lethimonier et al. (2017) *Hum. Reprod.* 32:1465; Galmés et al. (2021) *J. Agric. Food Chem.* 69:5281). When sulfate deconjugation has been required, chemical hydrolysis has usually been applied, and for some targets it remains superior to enzymes (Iannone et al. (2020) *J. Chromatogr. B* 1155:122280). But the same caveats apply as for deconjugation of sulfate esters: degradation and modification of targets, and stringent protocols required for accuracy, precision, and reproducibility. As a result, novel sulfatases that have new or expanded substrate profiles, and/or which have increased activity on target molecules, will become increasingly desirable and valuable.

Sulfatases occur in three unrelated protein superfamilies. Of these superfamilies—alkaline phosphatases (AP), non-heme iron(II) alpha-ketoglutarate-dependent dioxygenases, and metallo-beta-lactamases—the sulfatases of the AP superfamily are the most bountiful and best studied (SulfAtlas; Barbeyron et al. (2016) PLoS ONE 11: e016846). These sulfatases share a common structure: all have a modified amino acid residue—a formylglycine—generated by a second enzyme from either a cysteine or a serine occurring as part of a highly conserved sequence motif (Hanson et al. 2004 *Angew. Chem. Int. Ed.* 43:5736). Additionally, the enzyme requires a divalent cation, most often calcium, for activity. The calcium coordinates with the sulfate in the active site of the enzyme. The formylglycine displaces the molecule to which the sulfate is attached, forming a sulfo-enzyme intermediate, which is then hydrolyzed to release the free sulfate (Toesch et al. (2014) *Appl. Microbiol. Biotechnol.* 98:1485). This double displacement mechanism is akin to that of retaining glycosidases.

Products based on the arylsulfatase family have been commercialized and engineered for enhanced properties (Stressler et al. 2016, *Appl. Microbiol. Biotechnol.* 100: 9053), and several different sulfatase products based on naturally occurring enzymes, both crude and purified, and from mollusk and bacterial sources, are available on the market (cf. Sigma-Aldrich catalog: S9754, S1629, S9626, S9751, and S8504). Semi-rational and directed evolution protein engineering has been applied to improve and expand the substrate profile of the well-studied arylsulfatase from *Pseudomonas aeruginosa* (Uduwela et al. (2018) *ACS Catal.* 8:8902; Stevenson et al. (2022) *Protein Eng Des Sel.*). Furthermore, *P. aeruginosa* arylsulfatase has been engineered to be more efficient at hydrolyzing phenylphosphonate substrates while mostly retaining native activities on sulfate and mono- and di-ester phosphate substrates (Miton et al. (2018) *PNAS* 115:E7293-7302).

Additional *P. aeruginosa* arylsulfatase variants are still needed that have improved activity and substrate profiles on metabolic and drug targets of interest.

SUMMARY OF THE INVENTION

The invention provides variants of an arylsulfatase from *Pseudomonas aeruginosa*, termed PaS, that exhibit enhanced properties as compared to the parental enzyme from which they have been derived. In particular, the PaS variant enzymes of the disclosure exhibit enhanced enzymatic activity as compared to the parental enzyme from which they have been derived. Furthermore, the variant enzymes of the invention are produced recombinantly and thus can be prepared in a highly purified form without contaminating non-PaS proteins.

Accordingly, the disclosure pertains to PaS enzyme variants that comprise one or more mutations (e.g., amino acid substitutions at specified amino acid positions) as compared to the parental enzyme from which the variant is derived. In one aspect, the disclosure pertains to a variant *Pseudomonas aeruginosa* sulfatase (PaS) enzyme comprising at least one amino acid substitution at an amino acid position corresponding to A75, A139, R155, I156, K158, T160, I220, A323, L325, F328, K330, A376, F377 and/or M465 of a parental PaS enzyme comprising the amino acid sequence shown in SEQ ID NO: 1, wherein the variant PaS enzyme exhibits an increased level of enzymatic activity for one or more substrates as compared to the parental PaS enzyme, with the proviso that the variant PaS enzyme does not comprise R155P/I156V/L325F/K330V substitutions, R155P/L157V/K158I/K330V substitutions, R155P/I156L/L157V/K158V/T160S/K330V substitutions, I156L/K158E/L325F substitutions or R155P/P161A/A323D/L325F/P329R/K330V/W358N substitutions.

In embodiments, the variant PaS enzyme comprises an amino acid substitution selected from the group consisting of A139C, A139I, A139L, A139S and A139V. In embodiments, the variant PaS enzyme comprises an A139V substitution. In embodiments, the variant PaS enzyme comprises an amino acid sequence shown in SEQ ID NO: 2, 3, 4, 5 or 6.

In embodiments, the variant PaS enzyme comprises an amino acid substitution selected from the group consisting of R155D, R155E, R155G, R155P, R155Q and R155V. In embodiments, the variant PaS enzyme comprises an amino acid sequence shown in SEQ ID NO: 7, 8, 9, 10, 11 or 12. In one embodiment, the variant PaS enzyme consists of an R155P amino acid substitution (e.g., SEQ ID NO: 10). In one embodiment, the variant PaS enzyme comprises an R155P substitution, with the proviso that the variant PaS enzyme does not comprise R155P/I156V/L325F/F330V substitutions, R155P/L157V/K158I/K330V substitutions, R155P/I156L/L157V/K158V/T160S/K330V substitutions or R155P/P161A/A323D/L325F/P329R/K330V/W358N substitutions.

In embodiments, the variant PaS enzyme comprises an amino acid substitution selected from the group consisting of L325F, L325W and L325Y. In embodiments, the variant PaS enzyme comprises an amino acid sequence shown in SEQ ID NO: 13, 14 or 15. In one embodiment, the variant PaS enzyme consists of an L325F amino acid substitution (e.g., SEQ ID NO: 13). In one embodiment, the variant PaS enzyme comprises an L325F substitution, with the proviso that the variant PaS enzyme does not comprise R155P/I156V/L325F/F330V substitutions, I156L/K158E/L325F substitutions or R155P/P161A/A323D/L325F/P329R/K330V/W358N substitutions.

In embodiments, the variant PaS enzyme comprises an amino acid substitution selected from the group consisting of F328C, F328S and F328W. In embodiments, the variant PaS enzyme comprises an amino acid sequence shown in SEQ ID NO: 16, 17 or 18.

In embodiments, the variant PaS enzyme comprises an amino acid substitution K330T. In embodiments, the variant PaS enzyme comprises an amino acid sequence shown in SEQ ID NO: 19.

In embodiments, the variant PaS enzyme comprises an amino acid substitution selected from the group consisting of A376E, A376H, A376I, A376S, A376T and A376V. In embodiments, the variant PaS enzyme comprises an amino acid sequence shown in SEQ ID NO: 20, 21, 22,23, 24 or 25.

In embodiments, the variant PaS enzyme comprises an amino acid substitution selected from the group consisting of F377C, F377V and F377W. In embodiments, the variant PaS enzyme comprises an amino acid sequence shown in SEQ ID NO: 26, 27 or 28.

In embodiments, the variant PaS enzyme comprises an amino acid substitution selected from the group consisting of M465Q, M465S and M465T. In embodiments, the variant PaS enzyme comprises an amino acid sequence shown in SEQ ID NO: 29, 30 or 31.

In embodiments, the variant PaS enzyme comprises an amino acid substitution at amino acid position A139 and at least one additional amino acid substitution at a position(s) selected from the group consisting of R155, I156, I220, L325, F328, K330 and M465. Non-limiting examples include the variant PaS enzymes comprising the amino acid sequences shown in SEQ ID NOs: 32-40, 42-58 and 60-75.

In embodiments, the variant PaS enzyme comprises an amino acid substitution at amino acid position I220 and at least one additional amino acid substitution at a position(s) selected from the group consisting of A139, R155 and L325. Non-limiting examples include the variant PaS enzymes comprising the amino acid sequences shown in SEQ ID NOs: 41, 48 and 59.

In embodiments, the variant PaS enzyme comprises amino acid substitutions selected from the group consisting of A139V/R155C, A139V/R155D, A139V/R155E, A139V/R155G, A139V/R155K, A139V/R155L, A139V/R155S, A139V/R155V and A139V/R155W. In embodiments, the variant PaS enzyme comprises an amino acid sequence shown in any one of SEQ ID NOs: 32-40.

In embodiments, the variant PaS enzyme comprises amino acid substitutions at amino acid positions corresponding to R155 and I220 of a parental PaS enzyme comprising the amino acid sequence shown in SEQ ID NO: 1. In embodiments, the variant PaS enzyme comprises the amino acid substitutions R155E/I220M. In embodiments, the variant PaS enzyme comprises the amino acid sequence shown in SEQ ID NO: 41.

In embodiments, the variant PaS enzyme comprises amino acid substitutions at amino acid positions corresponding to A139 and I156 of a parental PaS enzyme comprising the amino acid sequence shown in SEQ ID NO: 1. In embodiments, the variant PaS enzyme comprises amino acid substitutions selected from the group consisting of A139V/I156A, A139V/I156D, A139V/I156E, A139V/I156G, A139V/I156T and A139V/I156W. In embodiments, the variant PaS enzyme comprises an amino acid sequence shown in any one of SEQ ID NOs: 42-47.

In embodiments, the variant PaS enzyme comprises amino acid substitutions at amino acid positions corresponding to A139 and I220 of a parental PaS enzyme comprising the amino acid sequence shown in SEQ ID NO: 1. In embodiments, the variant PaS enzyme comprises the amino acid substitutions A139V/I220M. In embodiments, the variant PaS enzyme comprises the amino acid sequence shown in SEQ ID NO: 48.

In embodiments, the variant PaS enzyme comprises amino acid substitutions at amino acid positions corresponding to A139 and L325 of a parental PaS enzyme comprising the amino acid sequence shown in SEQ ID NO: 1. In embodiments, the variant PaS enzyme comprises amino acid substitutions selected from the group consisting of A139V/L325C, A139V/L325H, A139V/L325G, A139V/L325K, A139V/L325P, A139V/L325T, A139V/L325V, A139V/L325Y, A139V/L325W and A139V/L325F. In embodiments, the variant PaS enzyme comprises an amino acid sequence shown in any one of SEQ ID NOs: 49-58. In one embodiment, the variant PaS enzyme consists of amino acid substitutions A139V and L325F (e.g., SEQ ID NO: 58).

In embodiments, the variant PaS enzyme comprises amino acid substitutions at amino acid positions corresponding to L325 and I220 of a parental PaS enzyme comprising the amino acid sequence shown in SEQ ID NO: 1. In embodiments, the variant PaS enzyme comprises the amino acid substitutions L325Y/I220M. In embodiments, the variant PaS enzyme comprises the amino acid sequence shown in SEQ ID NO: 59.

In embodiments, the variant PaS enzyme comprises amino acid substitutions at amino acid positions corresponding to A139 and F328 of the parental sulfatase enzyme comprising the amino acid sequence shown in SEQ ID NO: 1. In embodiments, the variant PaS enzyme comprises amino acid substitutions selected from the group consisting of A139V/F328A, A139V/F328C, A139V/F328L and A139V/F328W. In embodiments, the variant PaS enzyme comprises an amino acid sequence shown in any one of SEQ ID NOs: 60-63.

In embodiments, the variant PaS enzyme comprises amino acid substitutions at amino acid positions corresponding to A139 and K330 of a parental PaS enzyme comprising the amino acid sequence shown in SEQ ID NO: 1. In embodiments, the variant PaS enzyme comprises amino acid substitutions selected from the group consisting of A139V/K330D, A139V/K330S, A139V/K330T, A139V/K330V and A139V/K330Y. In embodiments, the variant PaS enzyme comprises an amino acid sequence shown in any one of SEQ ID NOs: 64-68.

In embodiments, the variant PaS enzyme comprises amino acid substitutions at amino acid positions corresponding to A139 and M465 of a parental PaS enzyme comprising the amino acid sequence shown in SEQ ID NO: 1. In embodiments, the variant PaS enzyme comprises amino acid substitutions selected from the group consisting of A139V/M465F, A139V/M465I, A139V/M465Q, A139V/M465S, A139V/M465E, A139V/M465P and A139V/M465V. In embodiments, the variant PaS enzyme comprises an amino acid sequence shown in any one of SEQ ID NOs: 69-75.

In embodiments, the variant PaS enzyme comprises amino acid substitutions at amino acid positions corresponding to A139, L325 and R155 of a parental PaS enzyme comprising the amino acid sequence shown in SEQ ID NO: 1. In embodiments, the variant PaS enzyme comprises amino acid substitutions selected from the group consisting of A139V/L325W/R155F, A139V/L325W/R155E, A139V/L325W/R155D, A139V/L325W/R155C, A139V/L325W/R155K, A139V/L325W/R155V, A139V/L325W/R155S, A139V/L325W/R155L and A139V/L325W/R155G. In embodiments, the variant PaS enzyme comprises an amino acid sequence shown in any one of SEQ ID NOs: 76-84.

In embodiments, the variant PaS enzyme comprises amino acid substitutions at amino acid positions corresponding to A139, L325 and K158 of a parental PaS enzyme comprising the amino acid sequence shown in SEQ ID NO: 1. In embodiments, the variant PaS enzyme comprises amino acid substitutions selected from the group consisting of A139V/L325W/K158D, A139V/L325W/K158N, A139V/L325W/K158W and A139V/L325W/K158I. In embodiments, the variant PaS enzyme comprises an amino acid sequence shown in any one of SEQ ID NOs: 85-88.

In embodiments, the variant PaS enzyme comprises amino acid substitutions at amino acid positions corresponding to A139, L325 and F328 of a parental PaS enzyme comprising the amino acid sequence shown in SEQ ID NO: 1. In embodiments, the variant PaS enzyme comprises amino acid substitutions selected from the group consisting of A139V/L325W/F328W, A139V/L325W/F328V, A139V/L325W/F328G, A139V/L325W/F328C and A139V/L325W/F328A. In embodiments, the variant PaS enzyme comprises an amino acid sequence shown in any one of SEQ ID NOs: 89-93.

In embodiments, the variant PaS enzyme comprises amino acid substitutions at amino acid positions corresponding to A139, L325 and M465 of a parental PaS enzyme comprising the amino acid sequence shown in SEQ ID NO: 1. In embodiments, the variant PaS enzyme comprises amino acid substitutions selected from the group consisting of A139V/L325W/M465A, A139V/L325W/M465Y, A139V/L325W/M465T, A139V/L325W/M465Q, A139V/L325W/M465N, A139V/L325W/M465L, A139V/L325W/M465I, A139V/L325W/M465W, A139V/L325W/M465C and A139V/L325W/M465F. In embodiments, the variant PaS enzyme comprises an amino acid sequence shown in any one of SEQ ID NOs: 94-103.

In embodiments, the variant PaS enzyme comprises amino acid substitutions at amino acid positions corresponding to A139, R155, L325 and K158 of a parental PaS enzyme comprising the amino acid sequence shown in SEQ ID NO: 1. In embodiments, the variant PaS enzyme comprises amino acid substitutions selected from the group consisting of A139V/R155E/L325W/K158V, A139V/R155E/L325W/K158R, A139V/R155E/L325W/K158N, A139V/R155E/L325W/K158M, A139V/R155E/L325W/K158I and A139V/R155E/L325W/K158D. In embodiments, the variant PaS enzyme comprises an amino acid sequence shown in any one of SEQ ID NOs: 104-109.

In embodiments, the variant PaS enzyme comprises amino acid substitutions at amino acid positions corresponding to A139, R155, L325 and A323 of a parental PaS enzyme comprising the amino acid sequence shown in SEQ ID NO: 1. In embodiments, the variant PaS enzyme comprises amino acid substitutions selected from the group consisting of A139V/R155E/L325W/A323Y, A139V/R155E/L325W/A323V, A139V/R155E/L325W/A323T, A139V/R155E/L325W/A323M, A139V/R155E/L325W/A323L, A139V/

R155E/L325W/A323I, A139V/R155E/L325W/A323F and A139V/R155E/L325W/A323C. In embodiments, the variant PaS enzyme comprises an amino acid sequence shown in any one of SEQ ID NOs: 110-117.

In embodiments, the variant PaS enzyme comprises amino acid substitutions at amino acid positions corresponding to A139, R155, L325 and F328 of a parental PaS enzyme comprising the amino acid sequence shown in SEQ ID NO: 1. In embodiments, the variant PaS enzyme comprises amino acid substitutions selected from the group consisting of A139V/R155E/L325W/F328G, A139V/R155E/L325W/F328C and A139V/R155E/L325W/F328V. In embodiments, the variant PaS enzyme comprises an amino acid sequence shown in any one of SEQ ID NOs: 118-120.

In embodiments, the variant PaS enzyme comprises amino acid substitutions at amino acid positions corresponding to A139, R155, L325 and M465 of a parental PaS enzyme comprising the amino acid sequence shown in SEQ ID NO: 1. In embodiments, the variant PaS enzyme comprises amino acid substitutions selected from the group consisting of A139V/R155E/L325W/M465W, A139V/R155E/L325W/M465V, A139V/R155E/L325W/M465S, A139V/R155E/L325W/M465Q, A139V/R155E/L325W/M465I and A139V/R155E/L325W/M465E. In embodiments, the variant PaS enzyme comprises an amino acid sequence shown in any one of SEQ ID NOs: 121-126.

In embodiments, the variant PaS enzyme comprises amino acid substitutions at amino acid positions corresponding to A139, R155, L325 and A75 of a parental PaS enzyme comprising the amino acid sequence shown in SEQ ID NO: 1. In embodiments, the variant PaS enzyme comprises amino acid substitutions selected from the group consisting of A139V/R155E/L325W/A75R, A139V/R155E/L325W/A75Q, A139V/R155E/L325W/A75H, A139V/R155E/L325W/A75G and A139V/R155E/L325W/A75F. In embodiments, the variant PaS enzyme comprises an amino acid sequence shown in any one of SEQ ID NOs: 127-131.

In embodiments, the variant PaS enzyme comprises amino acid substitutions at amino acid positions corresponding to A139, R155, L325 and T160 of a parental PaS enzyme comprising the amino acid sequence shown in SEQ ID NO: 1. In embodiments, the variant PaS enzyme comprises amino acid substitutions selected from the group consisting of A139V/R155E/T160S/L325W. In embodiments, the variant PaS enzyme comprises an amino acid sequence shown in SEQ ID NO: 132.

In embodiments, the variant PaS enzyme comprises amino acid substitutions at amino acid positions corresponding to A139, R155, T160, L325 and A75 of a parental PaS enzyme comprising the amino acid sequence shown in SEQ ID NO: 1. In embodiments, the variant PaS enzyme comprises amino acid substitutions selected from the group consisting of A75G/A139V/R155E/T160S/L325W. In embodiments, the variant PaS enzyme comprises an amino acid sequence shown in SEQ ID NO: 133.

In another aspect, the disclosure pertains to a variant *Pseudomonas aeruginosa* sulfatase (PaS) enzyme comprising an A139V substitution as compared to a parental PaS enzyme comprising the amino acid sequence shown in SEQ ID NO: 1. In embodiments, the variant PaS enzyme further comprises at least one amino acid substitution at an amino acid position corresponding to A75, R155, I156, K158, T160, I220, A323, L325, F328, K330, A376, F331, F377 and/or M465 of the parental PaS enzyme comprising the amino acid sequence shown in SEQ ID NO: 1.

In another aspect, the disclosure pertains to a variant PaS enzyme which comprises at least two amino acid substitutions at amino acid positions selected from the group consisting of A139/F328; A139/R155; A139/I156; A139/I220; A139/L325; A139/K330; A139/M465; I220/R155; and I220/L325.

In another aspect, the disclosure pertains to a variant PaS enzyme which comprises at least three amino acid substitutions at amino acid positions selected from the group consisting of A139/R155/L325; A139/K158/L325; A139/L325/F328; and A139/L325/M465.

In another aspect, the disclosure pertains to a variant PaS enzyme of claim 1, which comprises at least four amino acid substitutions at amino acid positions selected from the group consisting of A139/R155/K158/L325; A139/R155/A323/L325; A139/R155/L325/F328; A139/R155/L325/M465; A75/A139/R155/L325; and A139/R155/T160/L325.

In another aspect, the disclosure pertains to a variant *Pseudomonas aeruginosa* sulfatase (PaS) enzyme comprising at least one amino acid substitution as compared to a parental PaS enzyme comprising the amino acid sequence shown in SEQ ID NO: 1, wherein the at least one amino acid substitution is selected from the group consisting of A75F, A75G, A75H, A75Q, A75R, A139C, A139I, A139L, A139S, A139V, R155C, R155D, R155E, R155F, R155G, R155K, R155L, R155Q, R155S, R155V, K158D, K158M, K158N, K158R, K158W, T160S, A323C, A323F, A323I, A323L, A323M, A323T, A323V, A323Y, L325W, L325Y, F328A, F328C, F328G, F328S, F328V, F328W, K330T, A376E, A376H, A376I, A376S, A376T, A376V, F377C, F377V, F377W, M465A, M465C, M465E, M465F, M465I, M465L, M465Q, M465N, M465S, M465T, M465V, M465W, M465Y, and combinations thereof.

In another aspect, the disclosure pertains to a variant *Pseudomonas aeruginosa* sulfatase (PaS) enzyme comprising an amino acid sequence shown in any one of SEQ ID NOs: 2-133.

In another aspect, the disclosure pertains to formulations of the variant PaS enzymes. In embodiments, the formulations comprise a variant PaS enzyme of the disclosure and at least one excipient.

In another aspect, the disclosure pertains to a method of hydrolyzing a substrate comprising a sulfate ester linkage, the method comprising contacting the substrate with a variant PaS enzyme of the disclosure such that hydrolysis of the sulfate ester linkage occurs. In embodiments, the substrate is a steroid or an opioid. In embodiments, the substrate is selected from the group consisting of cortisol 21-sulfate (CS), 17α-estradiol sulfate (αES), 17β-estradiol sulfate (βES), boldenone sulfate (BS), dehydroepiandrosterone 3-sulfate (DHEAS), testosterone sulfate (TS), epiandrosterone sulfate (EAS), androsterone sulfate (AS), epitestosterone sulfate (ETS) and etiocholanolone sulfate (ECS), or derivatives thereof. In embodiments, the substrate is selected from the group consisting of morphine-3-sulfate (M3S), morphine-6-sulfate (M6S), hydromorphone-3-sulfate (H3S), oxymorphone-3-sulfate (O3S), codeine-6-sulfate (C6S) and tapentadol O-sulfate (TAPS), or derivatives thereof.

In one embodiment, the variant PaS enzyme comprises the amino acid sequence shown in SEQ ID NO: 6 (comprising an A139V substitution) and the substrate is cortisol 21-sulfate (CS), boldenone sulfate (BS) or dehydroepiandrosterone 3-sulfate (DHEAS).

In one embodiment, the variant PaS enzyme comprises the amino acid sequence shown in SEQ ID NO: 13 (comprising an L325F substitution) and the substrate is cortisol 21-sulfate (CS), boldenone sulfate (BS) or dehydroepiandrosterone 3-sulfate (DHEAS).

In one embodiment, the variant PaS enzyme comprises the amino acid sequence shown in SEQ ID NO: 14 (comprising an L325W substitution) and the substrate is cortisol 21-sulfate (CS) or boldenone sulfate (BS).

In one embodiment, the variant PaS enzyme comprises the amino acid sequence shown in SEQ ID NO: 15 (comprising an L325Y substitution) and the substrate is boldenone sulfate (BS).

In one embodiment, the variant PaS enzyme comprises the amino acid sequence shown in SEQ ID NO: 29 (comprising an M465Q substitution) and the substrate is 17α-estradiol sulfate (αES) or dehydroepiandrosterone 3-sulfate (DHEAS).

In one embodiment, the variant PaS enzyme comprises the amino acid sequence shown in SEQ ID NO: 34 (comprising A139V/R155E substitutions) and the substrate is boldenone sulfate (BS) or dehydroepiandrosterone 3-sulfate (DHEAS).

In one embodiment, the variant PaS enzyme comprises the amino acid sequence shown in SEQ ID NO: 56 (comprising A139V/L325Y substitutions) and the substrate is cortisol 21-sulfate (CS) or boldenone sulfate (BS).

In one embodiment, the variant PaS enzyme comprises the amino acid sequence shown in SEQ ID NO: 57 (comprising A139V/L325W substitutions) and the substrate is cortisol 21-sulfate (CS) or boldenone sulfate (BS).

In one embodiment, the variant PaS enzyme comprises the amino acid sequence shown in SEQ ID NO: 58 (comprising A139V/L325F substitutions) and the substrate is cortisol 21-sulfate (CS) or boldenone sulfate (BS).

In one embodiment, the variant PaS enzyme comprises the amino acid sequence shown in SEQ ID NO: 77 (comprising A139V/R155E/L325W substitutions) and the substrate is cortisol 21-sulfate (CS), boldenone sulfate (BS) or dehydroepiandrosterone 3-sulfate (DHEAS).

In one embodiment, the variant PaS enzyme comprises the amino acid sequence shown in SEQ ID NO: 130 (comprising A75G/A139V/R155E/L325W substitutions) and the substrate is boldenone sulfate (BS).

In one embodiment, the variant PaS enzyme comprises the amino acid sequence shown in SEQ ID NO: 132 (comprising A139V/R155E/T160S/L325W substitutions) and the substrate is boldenone sulfate (BS).

In one embodiment, the variant PaS enzyme comprises the amino acid sequence shown in SEQ ID NO: 133 (comprising A75G/A139V/R155E/T160S/L325W substitutions) and the substrate is boldenone sulfate (BS).

In one embodiment, the variant PaS enzyme comprises the amino acid sequence shown in SEQ ID NO: 114 (comprising A139V/R155E/A323L/L325W substitutions) and the substrate is dehydroepiandrosterone 3-sulfate (DHEAS).

BRIEF DESCRIPTION OF THE FIGURES

FIG. 1 (SEQ ID NO:1) shows the amino acid sequence of arylsulfatase from Pseudomonas aeruginosa with key residues selected for mutation highlighted (A75, A139, R155, I156, K158, T160, I220, A323, L325, F328, K330, F331, A376, F377, M465).

K158X, A139V/R155E/L325W/F328X and A139V/R155E/ L325W/M465X on cortisol 21-sulfate (CS).

Figure 20:
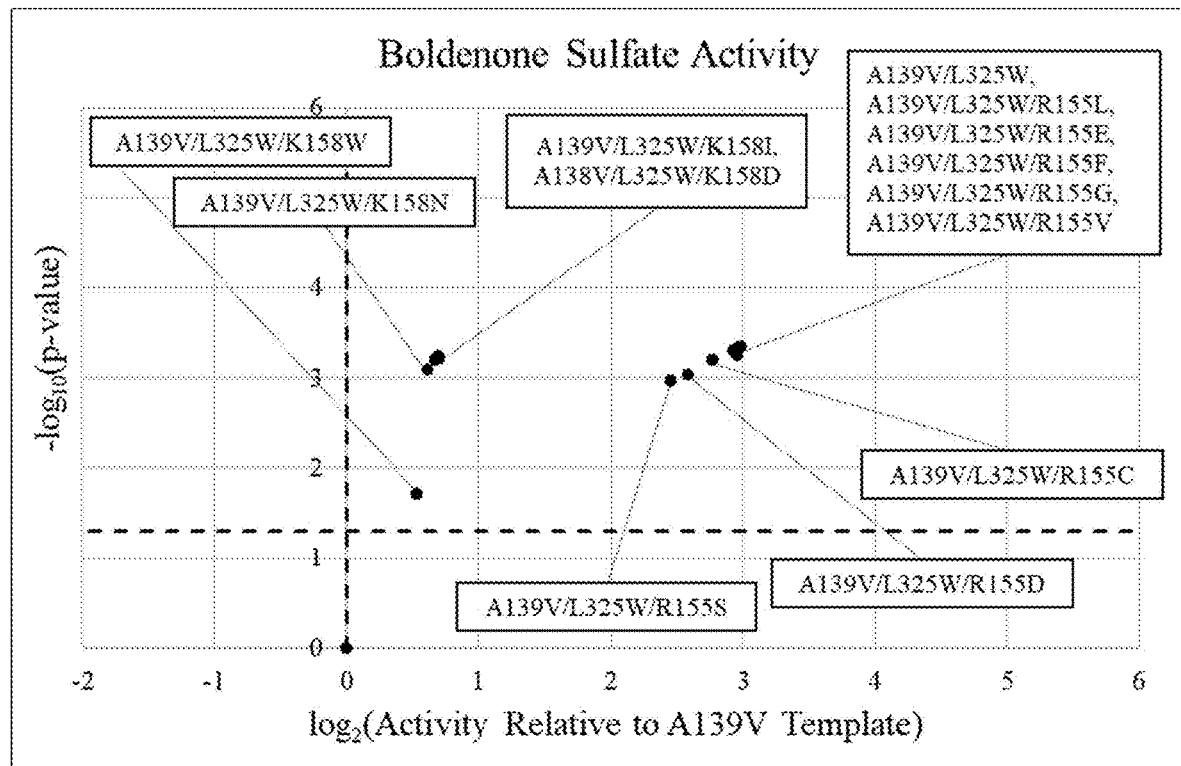

FIG. 20 is a graph showing the significant enzymatic activity of sulfatase variants A139V/L325W/R155X and A139V/L325W/K158X on boldenone sulfate (BS).

Figure 21:
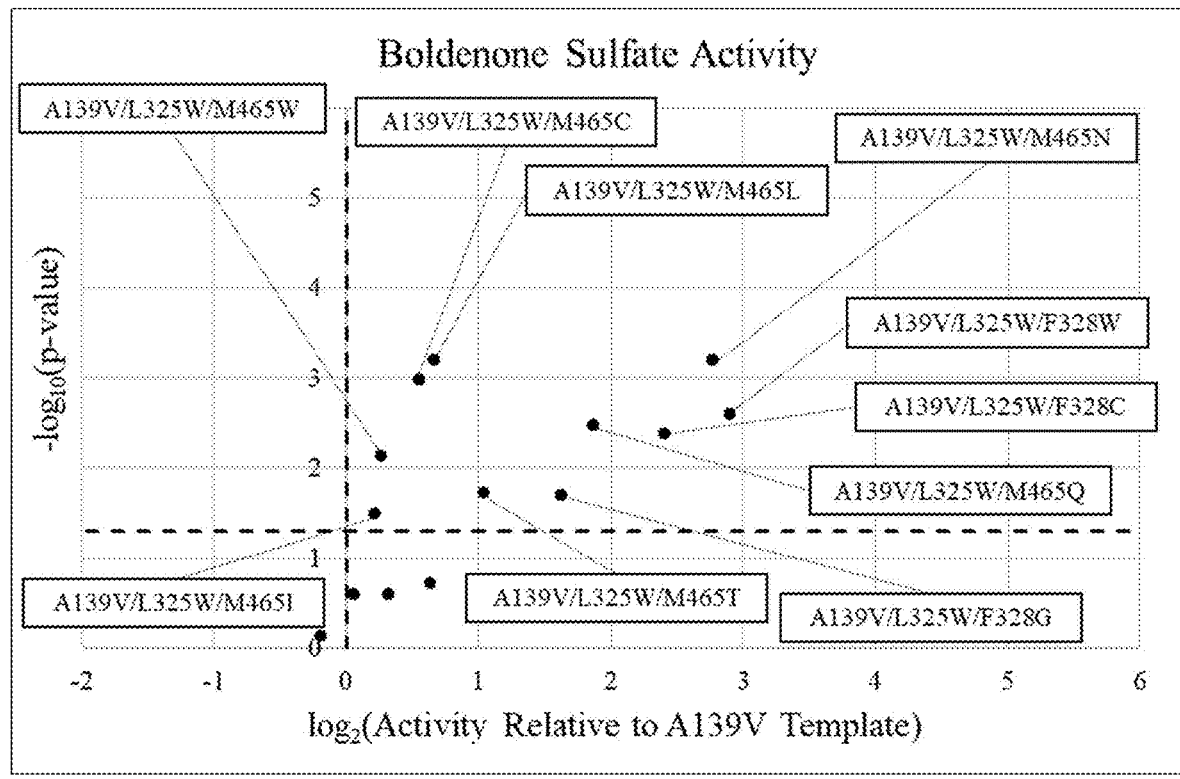

FIG. 21 is a graph showing the significant enzymatic activity of sulfatase variants A139V/L325W/F328X and A139V/L325W/M465X on boldenone sulfate (BS).

Figure 22:
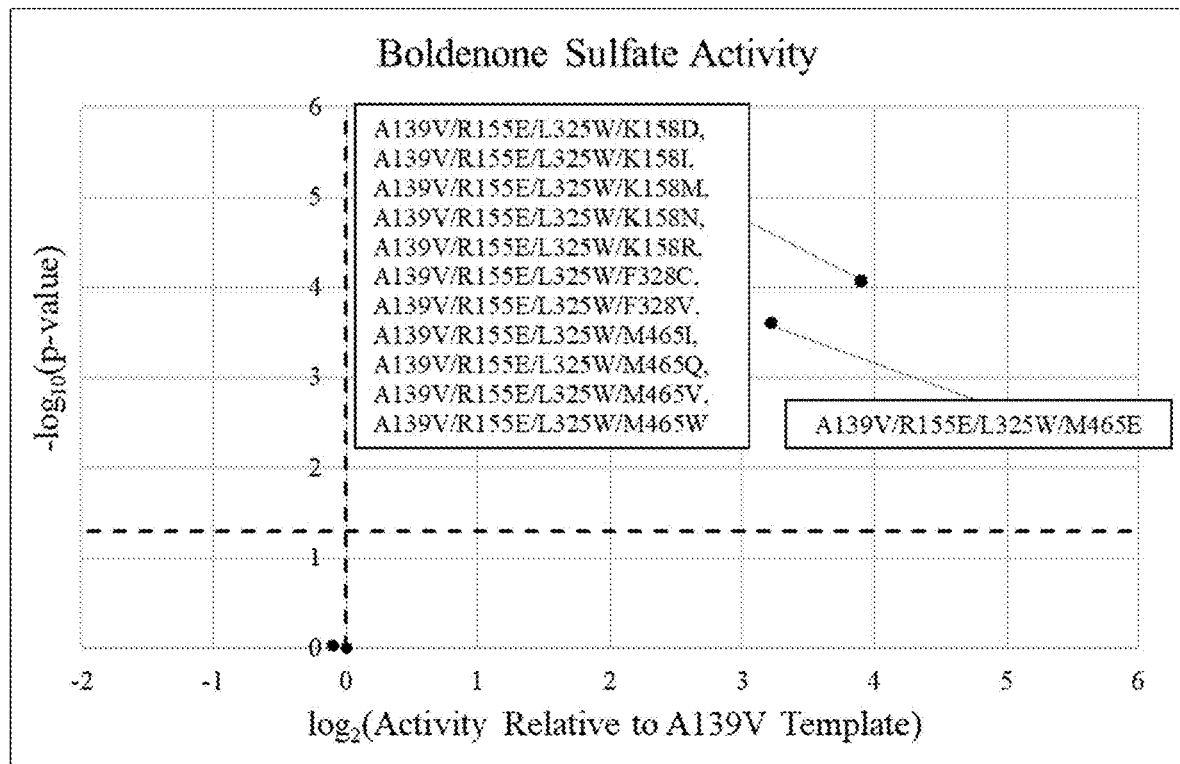

FIG. 22 is a graph showing the significant enzymatic activity of sulfatase variants A139V/R155E/L325W/ K158X, A139V/R155E/L325W/F328X and A139V/R155E/ L325W/M465X on boldenone sulfate (BS).

Figure 23:
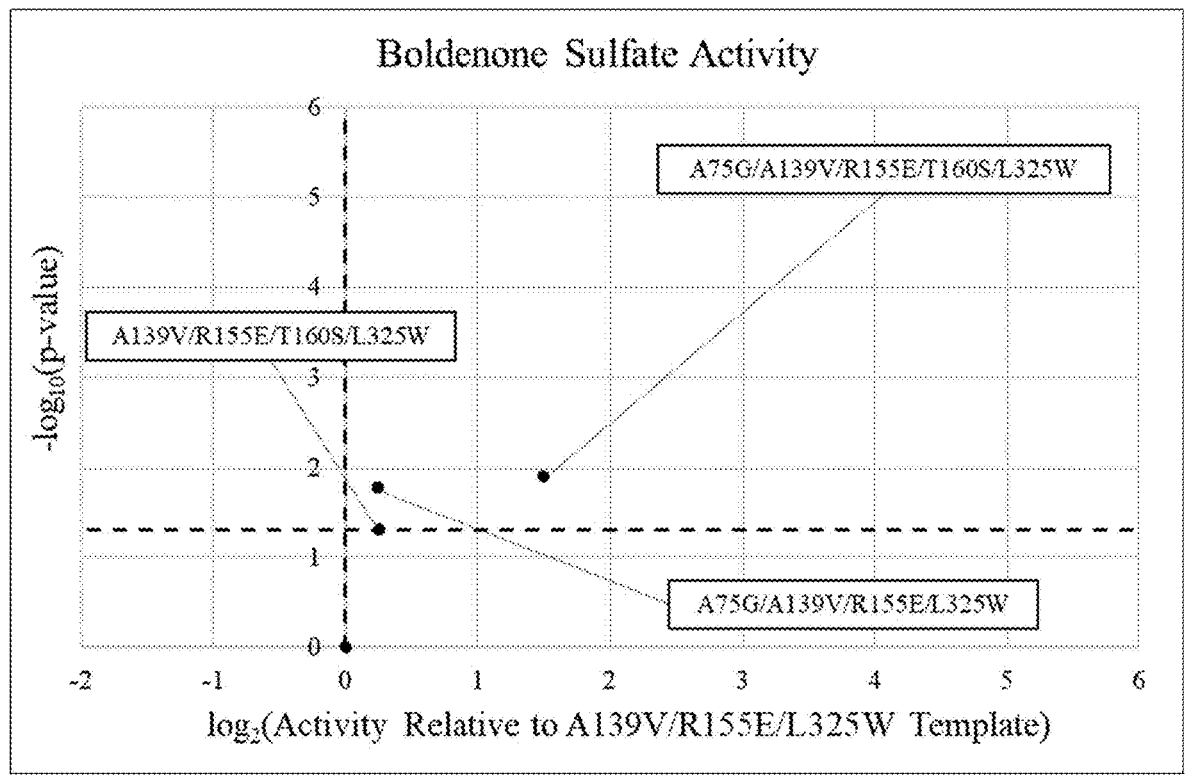

FIG. 23 is a graph showing the significant enzymatic activity of sulfatase variants A75G/A139V/R155E/T160S/ L325W, A139V/R155E/T160S/L325W and A75G/A139V/ R155E/L325W on boldenone sulfate (BS).

Figure 24:
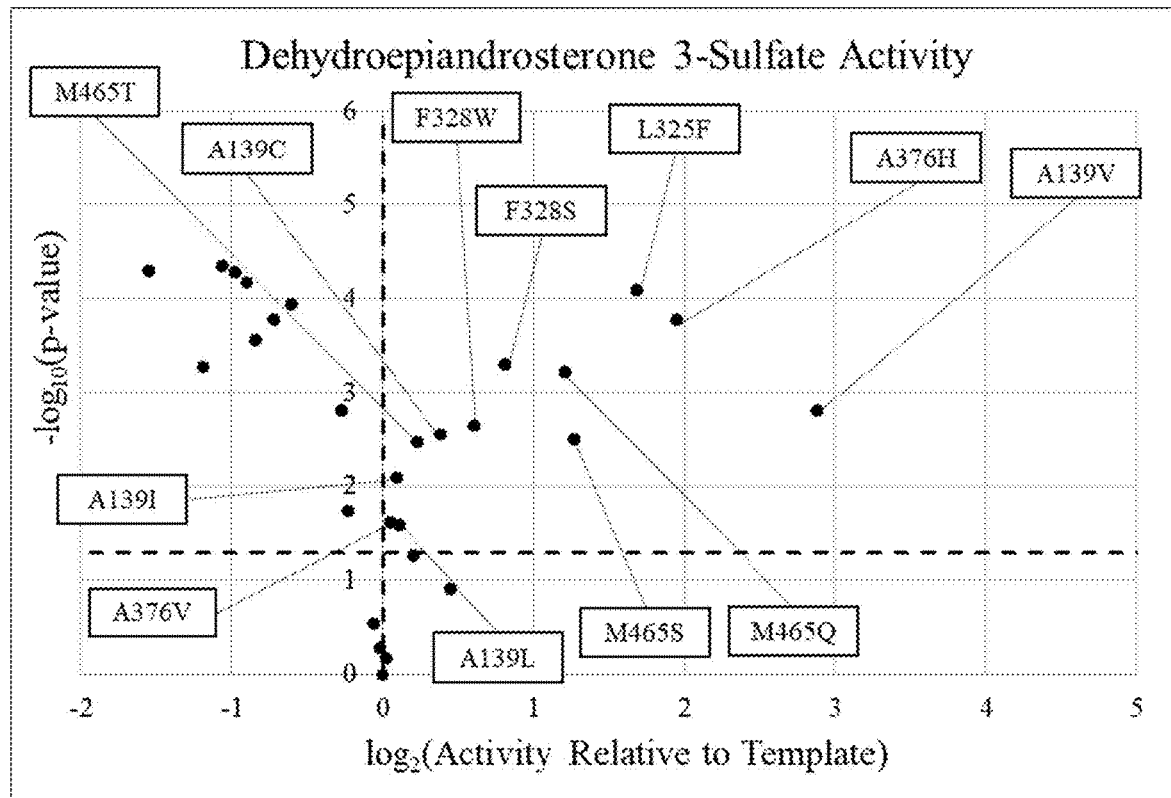

FIG. 24 is a graph showing the significant enzymatic activity of sulfatase variants A139X, R155X, L325X, F328X, A376X, F377X and M465X dehydroepiandrosterone 3-sulfate (DHEAS).

Figure 25:
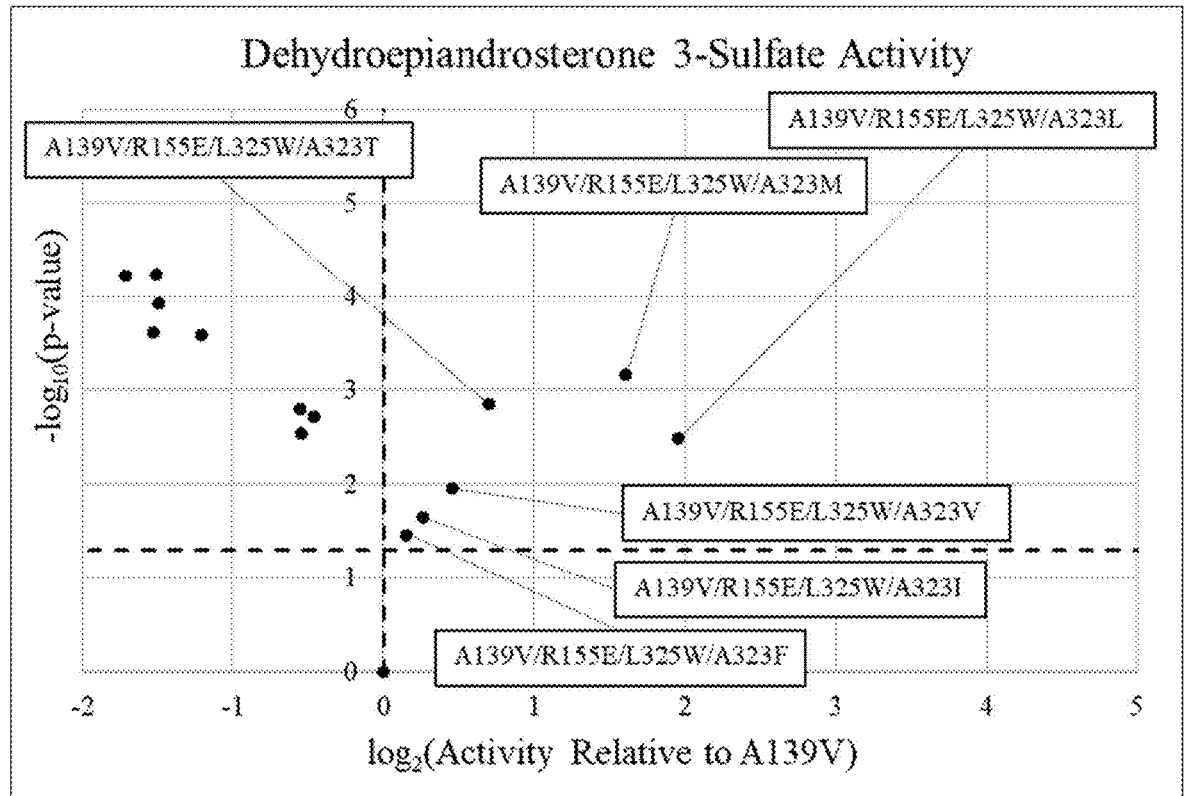

FIG. 25 is a graph showing the significant enzymatic activity of sulfatase variants A139V/R155E/L325W/T160S, A139V/R155E/L325W/I156L, A139V/R155E/L325W/ I156V and A139V/R155E/L325W/A323X on dehydroepiandrosterone 3-sulfate (DHEAS).

DETAILED DESCRIPTION OF THE INVENTION

The invention pertains to multiple variants of an arylsulfatase enzyme from *Pseudomonas aeuruginosa* (PaS) having enhanced properties as compared to the parental enzyme from which the variant form was derived, as well as packaged formulations thereof and methods of using the enzymes for hydrolysis of sulfate ester linkages.

The sequence of arylsulfatase from *P. aeruginosa*, referred to herein as PaS, is known (FIG. 1; GenBank: NC_002516.2) and contains 536 amino acids with a molecular weight of 59.9 kDa. PaS has been well characterized in the literature (see e.g., Boltes et al. (2001) *Structure* 9:483-91; Stevenson et al. (2015) *Drug Test. Anal.* 7:903-11; Uduwela et al. (2018) *ACS Catal.* 8:8902-14; Stevenson et al. (2022) *Protein Eng Des Sel.*), and there are several crystal structures of the enzyme available in the protein data bank (PDB). Amino acid residues D13, D14, C51 (converted to a formylglycine), H115, D317, and N318 are involved in coordinating the calcium ion and sulfate moiety of substrates in the active site (Boltes et al. (2001) *Structure* 9:483-91). While there are several PDB structures of PaS available, none of them are crystallized with relevant steroid sulfate substrates, and it can only be speculated which amino acid residues are responsible for substrate specificity.

Mutagenesis is a powerful approach for determining residues that are important in protein structure and function, and it can be used to possibly produce favorable properties of a target protein such as improved thermostability or function. The mutations can be made in the nucleotide sequence of the gene coding for the protein, and the modified gene can be expressed to produce variants of the original template sequence. Key residues that substantially impact a property of an enzyme can be altered specifically, if they are known or can be predicted based on sequence and structural data, by using site-directed saturation mutagenesis (Folz et al. (1988) *J. Biol. Chem.* 263:2070-2078). Substitution of a single key residue in a sequence will yield 20 possible variants (including the original template). This can be achieved by using site-saturation mutagenesis such that codons for all 20 possible amino acids are each substituted at the same key position in the sequence (Steffens et al. (2007) *J. Biomol. Tech.* 18:147-149; Chronopoulou et al. (2011) *Curr. Protocols Protein Sci.* 63:26.6.1-26.6.10).

Uduwela et al. ((2018) *ACS Catal.* 8:8902-14) used a semi-rational mutagenesis approach and DNA shuffling to find PaS variants with altered substrate specificity or increased activity. Initially, based on a multiple sequence alignment of nearly 150 distinct sulfatase primary sequences, potential key residues were identified and characterized: R155, F328, K330, F331, F463 (Uduwela et al. (2018) *ACS Catal.* 8:8902-14). Mutagenesis of key residues R155 and K330 resulted in variants that had improved hydrolysis rates on testosterone sulfate (TS), but the authors state that mutagenesis of F328, F331, and F463 did not yield any beneficial mutants (Uduwela et al. (2018) *ACS Catal.* 8:8902-14). In addition, potential key residues were mutated in PaS in a combinatorial approach to observe any synergistic effects multiple mutations may have on activity or substrate specificity. Other key residues investigated were M72, E74, I156, L157, K158, T160, L325, and F331. Mutating residues M72 and E74 resulted in inactive PaS variants. However, it was found that mutations at R155(P/ T), I156(L/V), L157(A/V), K158(V/I/E), T160(S/P), L325 (V/F), K330(V), or combinations thereof, yielded PaS variants with increased activity or broader substrate specificity (Uduwela et al. (2018) *ACS Catal.* 8:8902-14).

Described herein are novel PaS enzyme variants generated by site-saturation mutagenesis. These variants have improved enzymatic activity against target substrates, as described herein.

Various aspects of the invention are described in further detail in the following subsections.

I. Variant PaS Enzymes

As used herein, the term "arylsulfatase", also referred to as "*P. aeruginosa* sulfatase", "sulfatase enzyme" or "PaS", refers to an enzyme from *Pseudomonas aeruginosa* that hydrolyzes sulfate ester linkages. A "parental" or "template" sulfatase enzyme refers to the starting enzyme that is modified to create a "variant" sulfatase enzyme. A "variant" sulfatase enzyme refers to a modified form of the enzyme in which one or more modifications, such as amino acid swaps, substitutions, deletions and/or insertions, have been made such that the amino acid sequence of the variant sulfatase enzyme differs from the parental or template amino acid sequence. Thus, the "variant" sulfatase enzyme is derived from the "parental" or "template" sulfatase enzyme through introduction of one or more modifications. The parental or template sulfatase amino acid sequence can be a "wild-type" sulfatase sequence, i.e., a naturally-occurring sulfatase enzyme, including its natural formylglycine residue.

In certain embodiments, the variant sulfatase enzymes are described as having substantial homology to a specified amino acid sequence disclosed herein. The term "substantial homology" indicates that two amino acid sequences, when optimally aligned and compared, are identical, with appropriate insertions or deletions, in at least about 80% of the amino acids, usually at least about 90% to 95%, and more preferably at least about 98% to 99.5% of the nucleotides.

The percent identity between two sequences is a function of the number of identical positions shared by the sequences (i.e., % homology=# of identical positions/total # of positions ×100), taking into account the number of gaps, and the length of each gap, which need to be introduced for optimal alignment of the two sequences. The comparison of sequences and determination of percent identity between two sequences can be accomplished using mathematical algorithm, as described in the non-limiting examples below. Methods and algorithms for determining the % homology between two protein sequences are well established in the art.

For example, the percent identity between two amino acid sequences can be determined using the Needleman and Wunsch ((1970) *J. Mol. Biol.* (48):444-453) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. Furthermore, a protein amino acid sequence can be used as a "query sequence" to perform a search against public databases to, for example, identify related sequences. Such searches can be performed using the XBLAST programs (version 2.0) of Altschul, et al. (1990) *J. Mol. Biol.* 215:403-10. BLAST protein searches can be performed with the XBLAST program, score=50, word-length=3 to obtain amino acid sequences homologous to the protein molecules of the invention. To obtain gapped alignments for comparison purposes, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

Cloning, expression, and purification of PaS enzyme variants is described in Examples 1-2.

Methods of determining the enzymatic activity of PaS enzymes are well-established in the art. For example, enzymatic activity of PaS variants against a variety of substrates can be evaluated as described in the Examples herein.

In one aspect, the disclosure provides variant PaS enzymes in which one or more key residues have been substituted with a different amino acid than is present in the parental (template) enzyme. Typically the parental (template) enzyme is the wildtype PaS enzyme, the amino acid sequence of which is shown in SEQ ID NO: 1. Non-limiting exemplary methods of preparing and screening such variants are described in detail in Example 5. Other suitable methods for preparing single or multiple point mutations within the PaS enzyme are well established in the art.

In embodiments, amino acid substitution(s) is made at one or more positions shown in the amino acid sequence of FIG. 1. These amino acid residues are depicted within the active site of the PaS enzyme in FIG. 2. The preparation variant PaS enzymes having single, double, triple or quadruple point mutations at these residues, and analysis of their enzymatic activities, are described in detail in Examples 6-33.

Accordingly, in one embodiment, the disclosure provides a variant arylsulfatase (PaS) enzyme derived from a parental PaS enzyme, the variant PaS enzyme comprising an amino acid sequence at least 80% homologous to an amino acid sequence shown in SEQ ID NO: 1 and comprising at least one amino acid substitution, as compared to the parental PaS enzyme, at an amino acid position(s) corresponding to A75, A139, R155, I156, K158, T160, I220, A323, L325, F328, K330, F331, A376, F377 and/or M465 of SEQ ID NO: 1, wherein the variant PaS enzyme exhibits an increased level of enzymatic activity for one or more substrates as compared to the parental PaS enzyme. In other embodiments, the variant PaS enzyme further comprises one or more additional substitutions at an amino acid position(s) corresponding to I156, I220 and/or K330 of SEQ ID NO: 1. In certain embodiments, the variant PaS enzyme comprising an amino acid substitution(s) at one or more of the aforementioned position(s) does not comprise the following combination substitutions: R155P/I156V/L325F/K330V substitutions, R155P/L157V/K158I/K330V substitutions, R155P/I156L/L157V/K158V/T160S/K330V substitutions, I156L/K158E/L325F substitutions or R155P/P161A/A323D/L325F/P329R/K330V/W358N substitutions.

In one embodiment, the variant PaS enzyme is at least 90% homologous to an amino acid sequence shown in SEQ ID NO: 1. In another embodiment, the variant PaS enzyme is at least 95% homologous to an amino acid sequence shown in SEQ ID NO: 1. In other embodiments, the variant PaS enzyme is at least 90%, 91%, 92%, 93%, 94%, 95%, 96%, 97%, 98%, 98.5%, 99% or 99.5% homologous to an amino acid sequence shown in SEQ ID NO: 1.

In one embodiment, the variant PaS enzyme comprises an amino acid substitution, as compared to the parental PaS enzyme, at an amino acid position corresponding to A139 of SEQ ID NO: 1. In specific embodiments, this variant PaS enzyme comprises an amino acid sequence selected from the group consisting of the amino acid sequences shown in SEQ ID NOs: 2-6 (corresponding to substitutions A139C, A139I, A139L, A139S and A139V, respectively).

In one embodiment, the variant PaS enzyme comprises an amino acid substitution, as compared to the parental PaS enzyme, at an amino acid position corresponding to R155 of SEQ ID NO: 1. In specific embodiments, this variant PaS enzyme comprises an amino acid sequence selected from the group consisting of the amino acid sequences shown in SEQ ID NOs: 7-12 (corresponding to substitutions R155D, R155E, R155G, R155P, R155Q and R155V, respectively). In an embodiment, the variant PaS enzyme consists of an R155P substitution (as compared to SEQ ID NO: 1), such as shown in SEQ ID NO: 10.

In one embodiment, the variant PaS enzyme comprises an amino acid substitution, as compared to the parental PaS enzyme, at an amino acid position corresponding to L325 of SEQ ID NO: 1. In specific embodiments, this variant PaS enzyme comprises an amino acid sequence selected from the group consisting of the amino acid sequences shown in SEQ ID NOs: 13-15 (corresponding to substitutions L325F, L325W and L325Y, respectively). In an embodiment, the variant PaS enzyme consists of an L325F substitution (as compared to SEQ ID NO: 1), such as shown in SEQ ID NO: 13.

In another embodiment, the variant PaS enzyme comprises an amino acid substitution, as compared to the parental PaS enzyme, at an amino acid position corresponding to F328 of SEQ ID NO: 1. In specific embodiments, this variant PaS enzyme comprises an amino acid sequence selected from the group consisting of the amino acid sequences shown in SEQ ID NOs: 16-18 (corresponding to substitutions F328C, F328S and F328W, respectively).

In one embodiment, the variant PaS enzyme comprises an amino acid substitution, as compared to the parental PaS enzyme, at an amino acid position corresponding to K330 of SEQ ID NO: 1. In specific embodiments, this variant PaS enzyme comprises an amino acid sequence shown in SEQ ID NO: 19 (corresponding to substitution K330T).

In another embodiment, the variant PaS enzyme comprises an amino acid substitution, as compared to the parental PaS enzyme, at an amino acid position corresponding to A376 of SEQ ID NO: 1. In specific embodiments, this variant PaS enzyme comprises an amino acid sequence selected from the group consisting of the amino acid sequences shown in SEQ ID NOs: 20-25 (corresponding to substitutions A376E, A376H, A376I, A376S, A376T and A376V, respectively).

In another embodiment, the variant PaS enzyme comprises an amino acid substitution, as compared to the parental PaS enzyme, at an amino acid position corresponding to F377 of SEQ ID NO: 1. In specific embodiments, this variant PaS enzyme comprises an amino acid sequence selected from the group consisting of the amino acid sequences shown in SEQ ID NOs: 26-28 (corresponding to substitutions F377C, F377V and F377W, respectively).

In another embodiment, the variant PaS enzyme comprises an amino acid substitution, as compared to the parental PaS enzyme, at an amino acid position corresponding to M465 of SEQ ID NO: 1. In specific embodiments, this variant PaS enzyme comprises an amino acid sequence selected from the group consisting of the amino acid sequences shown in SEQ ID NOs: 29-31 (corresponding to substitutions M465Q, M465S and M465T, respectively).

In another embodiment, the variant PaS enzyme comprises amino acid substitutions, as compared to the parental PaS enzyme, at amino acid positions corresponding to A139 and R155 of SEQ ID NO: 1. In specific embodiments, the variant comprises an amino acid sequence selected from the group consisting of the amino acid sequences shown in SEQ ID NOs: 32-40 (corresponding to substitutions A139V/R155C, A139V/R155D, A139V/R155E, A139V/R155G, A139V/R155K, A139V/R155L, A139V/R155S, A139V/R155V and A139V/R155W, respectively).

In another embodiment, the variant PaS enzyme comprises amino acid substitutions, as compared to the parental PaS enzyme, at amino acid positions corresponding to R155 and I220 of SEQ ID NO: 1. In specific embodiments, the variant comprises an amino acid sequence shown in SEQ ID NOs: 41 (corresponding to substitutions R155E/I220M).

In another embodiment, the variant PaS enzyme comprises amino acid substitutions, as compared to the parental PaS enzyme, at amino acid positions corresponding to A139 and I156 of SEQ ID NO: 1. In specific embodiments, the variant comprises an amino acid sequence selected from the group consisting of the amino acid sequences shown in SEQ ID NOs: 42-47 (corresponding to substitutions A139V/I156A, A139V/I156D, A139V/I156E, A139V/I156G, A139V/I156T, and A139V/I156W, respectively).

In another embodiment, the variant PaS enzyme comprises amino acid substitutions, as compared to the parental PaS enzyme, at amino acid positions corresponding to A139 and I220 of SEQ ID NO: 1. In specific embodiments, the variant comprises an amino acid sequence selected from the group consisting of the amino acid sequences shown in SEQ ID NO: 48 (corresponding to substitutions A139V/I220M).

In another embodiment, the variant PaS enzyme comprises amino acid substitutions, as compared to the parental PaS enzyme, at amino acid positions corresponding to A139 and L325 of SEQ ID NO: 1. In specific embodiments, the variant comprises an amino acid sequence selected from the group consisting of the amino acid sequences shown in SEQ ID NOs: 49-58 (corresponding to substitutions A139V/L325C, A139V/L325H, A139V/L325G, A139V/L325K, A139V/L325P, A139V/L325T, A139V/L325V, A139V/L325Y, A139V/L325W and 139V/L325F, respectively). In an embodiment, the variant PaS enzyme consists of amino acid substitutions A139V/L325F (as compared to SEQ ID NO: 1), such as shown in SEQ ID NO: 58.

In another embodiment, the variant PaS enzyme comprises amino acid substitutions, as compared to the parental PaS enzyme, at amino acid positions corresponding to L325 and I220 of SEQ ID NO: 1. In specific embodiments, the variant comprises an amino acid sequence selected from the group consisting of the amino acid sequences shown in SEQ ID NO: 59 (corresponding to substitutions L325Y/I220M).

In another embodiment, the variant PaS enzyme comprises amino acid substitutions, as compared to the parental PaS enzyme, at amino acid positions corresponding to A139 and F328 of SEQ ID NO: 1. In specific embodiments, the variant comprises an amino acid sequence selected from the group consisting of the amino acid sequences shown in SEQ ID NOs: 60-63 (corresponding to substitutions A139V/F328A, A139V/F328C, A139V/F328L and A139V/F328W, respectively).

In another embodiment, the variant PaS enzyme comprises amino acid substitutions, as compared to the parental PaS enzyme, at amino acid positions corresponding to A139 and K330 of SEQ ID NO: 1. In specific embodiments, the variant comprises an amino acid sequence selected from the group consisting of the amino acid sequences shown in SEQ ID NOs: 64-68 (corresponding to substitutions A139V/K330D, A139V/K330S, A139V/K330T, A139V/K330V and A139V/K330Y, respectively).

In another embodiment, the variant PaS enzyme comprises amino acid substitutions, as compared to the parental PaS enzyme, at amino acid positions corresponding to A139 and M465 of SEQ ID NO: 1. In specific embodiments, the variant comprises an amino acid sequence selected from the group consisting of the amino acid sequences shown in SEQ ID NOs: 69-75 (corresponding to substitutions A139V/M465F, A139V/M465I, A139V/M465Q, A139V/M465S, A139V/M465E, A139V/M465P and A139V/M465V, respectively).

In another embodiment, the variant PaS enzyme comprises amino acid substitutions, as compared to the parental PaS enzyme, at amino acid positions corresponding to A139, L325 and R155 of SEQ ID NO: 1. In specific embodiments, the variant comprises an amino acid sequence selected from the group consisting of the amino acid sequences shown in SEQ ID NOs: 76-84 (corresponding to substitutions A139V/L325W/R155F, A139V/L325W/R155E, A139V/L325W/R155D, A139V/L325W/R155C, A139V/L325W/R155K, A139V/L325W/R155V, A139V/L325W/R155S, A139V/L325W/R155L and A139V/L325W/R155G, respectively).

In another embodiment, the variant PaS enzyme comprises amino acid substitutions, as compared to the parental PaS enzyme, at amino acid positions corresponding to A139, L325 and K158 of SEQ ID NO: 1. In specific embodiments, the variant comprises an amino acid sequence selected from the group consisting of the amino acid sequences shown in SEQ ID NOs: 85-88 (corresponding to substitutions A139V/L325W/K158D, A139V/L325W/K158N, A139V/L325W/K158W and A139V/L325W/K158I, respectively).

In another embodiment, the variant PaS enzyme comprises amino acid substitutions, as compared to the parental PaS enzyme, at amino acid positions corresponding to A139, L325 and F328 of SEQ ID NO: 1. In specific embodiments, the variant comprises an amino acid sequence selected from the group consisting of the amino acid sequences shown in SEQ ID NOs: 89-93 (corresponding to substitutions A139V/L325W/F328W, A139V/L325W/F328V, A139V/L325W/F328G, A139V/L325W/F328C and A139V/L325W/F328A, respectively).

In another embodiment, the variant PaS enzyme comprises amino acid substitutions, as compared to the parental PaS enzyme, at amino acid positions corresponding to A139, L325 and M465 of SEQ ID NO: 1. In specific embodiments, the variant comprises an amino acid sequence selected from the group consisting of the amino acid sequences shown in SEQ ID NOs: 94-103 (corresponding to substitutions A139V/L325W/M465A, A139V/L325W/M465Y, A139V/L325W/M465T, A139V/L325W/M465Q, A139V/L325W/M465N, A139V/L325W/M465L, A139V/L325W/M465I, A139V/L325W/M465W, A139V/L325W/M465C and A139V/L325W/M465F, respectively).

In another embodiment, the variant PaS enzyme comprises amino acid substitutions, as compared to the parental PaS enzyme, at amino acid positions corresponding to A139, R155, L325 and K158 of SEQ ID NO: 1. In specific embodiments, the variant comprises an amino acid sequence selected from the group consisting of the amino acid sequences shown in SEQ ID NOs: 104-109 (corresponding to substitutions A139V/R155E/L325W/K158V, A139V/R155E/L325W/K158R, A139V/R155E/L325W/K158N, A139V/R155E/L325W/K158M, A139V/R155E/L325W/K158I and A139V/R155E/L325W/K158D, respectively).

In another embodiment, the variant PaS enzyme comprises amino acid substitutions, as compared to the parental PaS enzyme, at amino acid positions corresponding to A139, R155, L325 and A323 of SEQ ID NO: 1. In specific embodiments, the variant comprises an amino acid sequence selected from the group consisting of the amino acid sequences shown in SEQ ID NOs: 110-117 (corresponding to substitutions A139V/R155E/L325W/A323Y, A139V/R155E/L325W/A323V, A139V/R155E/L325W/A323T, A139V/R155E/L325W/A323M, A139V/R155E/L325W/A323L, A139V/R155E/L325W/A323I, A139V/R155E/L325W/A323F and A139V/R155E/L325W/A323C, respectively).

In another embodiment, the variant PaS enzyme comprises amino acid substitutions, as compared to the parental PaS enzyme, at amino acid positions corresponding to A139, R155, L325 and F328 of SEQ ID NO: 1. In specific embodiments, the variant comprises an amino acid sequence selected from the group consisting of the amino acid sequences shown in SEQ ID NOs: 118-120 (corresponding to substitutions A139V/R155E/L325W/F328G, A139V/R155E/L325W/F328C and A139V/R155E/L325W/F328V, respectively).

In another embodiment, the variant PaS enzyme comprises amino acid substitutions, as compared to the parental PaS enzyme, at amino acid positions corresponding to A139, R155, L325 and M465 of SEQ ID NO: 1. In specific embodiments, the variant comprises an amino acid sequence selected from the group consisting of the amino acid sequences shown in SEQ ID NOs: 121-126 (corresponding to substitutions A139V/R155E/L325W/M465W, A139V/R155E/L325W/M465V, A139V/R155E/L325W/M465S, A139V/R155E/L325W/M465Q, A139V/R155E/L325W/M465I and A139V/R155E/L325W/M465E, respectively).

In another embodiment, the variant PaS enzyme comprises amino acid substitutions, as compared to the parental PaS enzyme, at amino acid positions corresponding to A139, R155, L325 and A75 of SEQ ID NO: 1. In specific embodiments, the variant comprises an amino acid sequence selected from the group consisting of the amino acid sequences shown in SEQ ID NOs: 127-131 (corresponding to substitutions A139V/R155E/L325W/A75R, A139V/R155E/L325W/A75Q, A139V/R155E/L325W/A75H, A139V/R155E/L325W/A75G and A139V/R155E/L325W/A75F, respectively).

In another embodiment, the variant PaS enzyme comprises amino acid substitutions, as compared to the parental PaS enzyme, at amino acid positions corresponding to A139, R155, L325 and T160 of SEQ ID NO: 1. In specific embodiments, the variant comprises an amino acid sequence selected from the group consisting of the amino acid sequences shown in SEQ ID NO: 132 (corresponding to substitutions A139V/R155E/T160S/L325W).

In another embodiment, the variant PaS enzyme comprises amino acid substitutions, as compared to the parental PaS enzyme, at amino acid positions corresponding to A139, R155, T160, L325 and A75 of SEQ ID NO: 1. In specific embodiments, the variant comprises an amino acid sequence selected from the group consisting of the amino acid sequences shown in SEQ ID NO: 133 (corresponding to substitutions A75G/A139V/R155E/T160S/L325W).

II. Preparation of Variant PaS Enzymes

The PaS enzymes of the invention can be prepared using standard recombinant DNA techniques. Exemplary methods for preparing amino acid-substituted variants are described in the Examples, although other methods known in the art for protein mutagenesis by standard recombinant DNA techniques are also suitable. Once a nucleic acid fragment encoding the desired variant PaS enzyme has been obtained, the fragment can be inserted into a suitable expression vector, transformed into a suitable host cell and the variant protein expressed recombinantly by culturing of the host cell, e.g., as described in Example 1. Suitable DNA constructs, expression vectors and host cells are well established in the art.

Accordingly, in another aspect, the disclosure provides a DNA construct encoding a variant PaS enzyme of the disclosure, including plasmid constructs. In another aspect, the disclosure provides an expression vector comprising the DNA construct encoding the variant PaS enzyme, including plasmid expression vectors and viral expression vectors. In another aspect, the disclosure provides a host cell comprising an expression vector encoding the chimeric or other variant PaS enzyme, including prokaryotic (e.g., bacterial) and eukaryotic (e.g., yeast) host cells. In yet another aspect, the disclosure provides a method of expressing (i.e., producing) the variant PaS enzymes by culturing the host cells such that the enzyme is expressed. Suitable culture conditions for host cells are well established in the art.

Following recombinant expression of the variant PaS enzyme, the protein can be purified using standard protein purification techniques, such as those described in Example 2. For example, standard affinity chromatography methods, such as immunoaffinity chromatography using an anti-PaS antibody or metal ion affinity chromatography using nickel, cobalt or copper resin, can be used. Furthermore, dispersive pipette extraction technology, such as IMCStips™, can be used for enzyme purification (e.g., as described in Example 2). Recombinant variant enzyme typically exhibits a significantly higher degree of purity than commercially available extracts from abalone, snail or humans. Thus, the recombinant variant enzymes of the disclosure advantageously lack contaminating proteins found in commercially available crude extract preparations, which contaminating proteins could interfere with enzyme activity or efficiency.

III. Formulations

The variant PaS enzymes of the disclosure can be included in formulations that contain additional substances and/or that are formulated in a particular way. For example, the formulations of the disclosure can be either liquid (aqueous) or lyophilized (freeze-dried). Liquid formulations typically allow for maintenance of enzymatic activity even after cycles of freezing/thawing. Lyophilized formulations typically maintain enzymatic activity over a wide temperature range, including high temperatures. Typically, a formulation comprises the enzyme composition and at least one excipient. Non-limiting examples of excipients that can be included in a formulation include water, salts, buffers, sugars and amino acids.

Aqueous and lyophilized formulations can be prepared using methods well established in the art. Typically, an aqueous formulation is prepared by combining the enzymes and the excipient(s) at the desired concentrations. A lyophilized formulation can be made by freeze-drying the aqueous formulation using techniques well established in the art.

In certain embodiments, one or more sugars are used in the formulation. In one embodiment, the sugar is a polyol. In certain embodiments, the sugar(s) used in the formulation is selected from the group consisting of sucrose, sorbitol, xylitol, glycerol, 2-hydroxypropyl-β-cyclodextrin and α-cyclodextrin. In a preferred embodiment, the sugar is sucrose.

In certain embodiments, the sugar is present in the formulation at a concentration of at least 10 mM, or at least 25 mM or at least 50 mM or at least 100 mM. In other embodiments, the sugar is present in the formulation at a concentration of 10-1000 mM, or 25-500 mM or 50 mM-250 mM or 50 mM-500 mM or 50 mM-1000 mM. In other embodiments, the sugar is present in the formulation at a concentration of 50 mM or 75 mM or 100 mM or 200 mM or 250 mM or 300 mM or 400 mM or 500 mM or 600 mM or 700 mM or 750 mM or 800 mM or 900 mM or 1000 mM.

In certain embodiments, one or more amino acids (e.g., beta-alanine, L-histidine) is present in the formulation at a concentration of at least 25 mM or at least 50 mM. In other embodiments, the amino acid(s) is present in the formulation at a concentration of 25-500 mM or 50 mM-250 mM or 50 mM-500 mM. In other embodiments, the amino acid(s) is present in the formulation at a concentration of 25 mM or 30 mM or 40 mM or 50 mM or 75 mM or 100 mM or 200 mM or 250 mM or 300 mM or 400 mM or 500 mM.

In certain embodiments, the variant PaS enzyme is present in the formulation at a concentration of at least 0.1 mg/mL. In certain embodiments, the variant PaS enzyme is present in the formulation at a concentration of at least 1 mg/mL or at least 2.5 mg/mL or at least 5 mg/mL or at least 10 mg/mL. In other embodiments, the variant PaS enzyme is present in the formulation at a concentration of 1-10 mg/mL or 1-5 mg/mL or 2.5-10 mg/mL or 2.5-5 mg/mL.

In other embodiments, the variant PaS enzyme is present in the formulation at a concentration of 1 mg/mL or 2 mg/mL or 3 mg/mL or 4 mg/mL or 5 mg/mL or 6 mg/mL or 7 mg/mL or 8 mg/mL or 9 mg/mL or 10 mg/mL.

In certain embodiments, the variant PaS enzyme in the formulation has an enzymatic activity of at least 5,000 Units/mL or 5,000 Units/mg, more preferably at least 10,000 Units/mL or 10,000 Units/mg, even more preferably at least 25,000 Units/mL or 25,000 Units/mg and even more preferably 50,000 Units/mL or 50,000 Units/mg. The specific activity of the enzyme in the preparation, in Units/mL or Units/mg, can be determined using a standardized sulfate ester linkage hydrolysis assay using p-nitrocatechol sulfate as the substrate. The standardization of the specific activity of PaS has been well established in the art. Exemplary standardized assays that can be used to determine the specific activity (in Units/mL or Units/mg) of an enzyme preparation are described in further detail in the examples. The skilled artisan will appreciate that other protocols for the enzyme assay are also suitable (e.g., such as those described by Sigma Aldrich Chemical Co.).

In one embodiment, the formulation is free of detergents, such as surfactants (e.g., Tween compounds and the like). Since the presence of detergents in a PaS formulation can interfere with mass spectrometry (MS) analysis, the lack of detergent(s) in the formulation of the invention imparts the advantage that the formulation can be used directly in analysis of biological samples to be assayed by mass spectrometry (MS).

In one embodiment, the formulation is free of polymers (e.g., synthetic polymers and the like). Since the presence of polymers in a PaS formulation can interfere with MS analysis, the lack of polymer(s) in the formulation of the invention imparts the advantage that the formulation can be used directly in analysis of biological samples to be assayed by MS.

Packaged formulations, comprising a formulation of the disclosure and a container, are also encompassed. Non-limiting examples of suitable containers for use in a packed formulation include, bottles, tubes, vials, ampules and the like. Preferably, the container is glass or plastic, although other suitable materials are known in the art. Non-limiting examples of suitable instruction media include labels, pamphlets, inserts, and digital media.

IV. Methods of Use

The variant PaS enzymes of the invention exhibit enhanced properties in their ability to hydrolyze sulfate ester linkages as compared to the parental enzyme from which they are derived. Accordingly, the variant enzymes can be used in methods for hydrolysis of sulfate ester substrates. The variant enzymes can be used, for example, for clinical purposes, for forensic purposes, for industrial manufacturing purposes or for agricultural purposes. These methods are particularly useful for analyzing bodily samples for the presence of drugs through detection of the sulfate ester detoxification products of the drugs, e.g., for clinical or forensic purposes.

Thus, in another aspect the invention pertains to a method of hydrolyzing a substrate comprising a sulfate ester linkage, the method comprising contacting the substrate with a variant arylsulfatase enzyme of the disclosure under conditions such that hydrolysis of the sulfate ester linkage occurs. Any of the variant enzymes of the invention, including those having a single amino acid substitution or those having double amino acid substitutions, can be used in the method.

In one embodiment, the substrate comprises a steroid sulfate ester. Non-limiting examples of suitable steroid sulfate ester substrates include cortisol 21-sulfate (CS), 17α-estradiol (αES), 17β-estradiol (βES), boldenone sulfate (BS), dehydroepiandrosterone 3-sulfate (DHEAS), testosterone sulfate (TS), epiandrosterone sulfate (EAS), androsterone sulfate (AS), epitestosterone sulfate (ETS), etiocholanolone sulfate (ECS) and derivatives or combinations thereof.

In one embodiment, the substrate comprises an opioid sulfate ester. Non-limiting examples of suitable opioid sulfate ester substrates include morphine-3-sulfate (M3S), morphine-6-sulfate (M6S), hydromorphone-3-sulfate (H3S), oxymorphone-3-sulfate (O3S), codeine-6-sulfate (C6S), tapentadol O-sulfate (TAPS) and derivatives or combinations thereof.

In certain embodiments of the method of hydrolyzing a substrate, one or more particular substrates are used in combination with a particular variant PaS enzyme that exhibits enhanced enzymatic activity against that particular substrate as compared to the parental PaS enzyme from which the variant is derived. For example, in one embodiment, the disclosure pertains to a method of hydrolyzing boldenone sulfate (BS), the method comprising contacting BS with a variant PaS enzyme comprising an amino acid substitution, as compared to the parental PaS enzyme, at an amino acid position corresponding to A139 of SEQ ID NO: 1 (e.g., an A139V substitution), such that hydrolysis of BS occurs. In one embodiment of this method, the variant PaS enzyme comprises the amino acid sequence shown in SEQ ID NO: 6 (PaS comprising an A139V mutation). In another embodiment of this method, the variant PaS enzyme comprises the amino acid sequence shown in SEQ ID NO: 13 (PaS comprising L325F mutation). In another embodiment of this method, the variant PaS enzyme consists of an L325F amino acid substitution (SEQ ID NO: 13). In another embodiment of this method, the variant PaS enzyme comprises the amino acid sequence shown in SEQ ID NO: 14 (PaS comprising L325W mutation). In another embodiment of this method, the variant PaS enzyme comprises the amino acid sequence shown in SEQ ID NO: 15 (PaS comprising L325Y mutation). In another embodiment of this method, the variant PaS enzyme comprises the amino acid sequence shown in SEQ ID NO: 34 (PaS comprising A139V/R155E mutations). In another embodiment of this method, the variant PaS enzyme comprises the amino acid sequence shown in SEQ ID NO: 56 (PaS comprising A139V/L325Y mutations). In another embodiment of this method, the variant PaS enzyme comprises the amino acid sequence shown in SEQ ID NO: 57 (PaS comprising A139V/L325W mutations). In another embodiment of this method, the variant PaS enzyme comprises the amino acid sequence shown in SEQ ID NO: 58 (PaS comprising A139V/L325F mutations). In another embodiment of this method, the variant PaS enzyme consists of A139V/L325F amino acid substitutions (SEQ ID NO: 58). In another embodiment of this method, the variant PaS enzyme consists of A139V/R155E/L325W amino acid substitutions (SEQ ID NO: 77). In another embodiment of this method, the variant PaS enzyme consists of A75G/A139V/R155E/L325W amino acid substitutions (SEQ ID NO: 130). In another embodiment of this method, the variant PaS enzyme consists of A139V/R155E/T160S/L325W amino acid substitutions (SEQ ID NO: 132). In another embodiment of this method, the variant PaS enzyme consists of A75G/A139V/R155E/T160S/L325W amino acid substitutions (SEQ ID NO: 133).

In another embodiment, the disclosure pertains to a method of hydrolyzing 17α-estradiol (αES), the method comprising contacting αES with a variant PaS enzyme comprising an amino acid substitution, as compared to the parental PaS enzyme, at an amino acid position corresponding to M465 of SEQ ID NO: 1 (e.g., an M465Q substitution), such that hydrolysis of αES occurs. In one embodiment of this method, the variant PaS enzyme comprises the amino acid sequence shown in SEQ ID NO: 29 (PaS comprising an M465Q mutation).

In another embodiment, the disclosure pertains to a method of hydrolyzing cortisol 21-sulfate (CS), the method comprising contacting CS with a variant PaS enzyme comprising an amino acid substitution, as compared to the parental PaS enzyme, at an amino acid position corresponding to A139 of SEQ ID NO: 1 (e.g., an A139V substitution), such that hydrolysis of CS occurs. In one embodiment of this method, the variant PaS enzyme comprises the amino acid sequence shown in SEQ ID NO: 6 (PaS comprising an A139V mutation). In another embodiment of this method, the variant PaS enzyme comprises the amino acid sequence shown in SEQ ID NO: 13 (PaS comprising L325F mutation). In another embodiment of this method, the variant PaS enzyme consists of an L325F amino acid substitution (SEQ ID NO: 13). In another embodiment of this method, the variant PaS enzyme comprises the amino acid sequence shown in SEQ ID NO: 14 (PaS comprising L325W mutation). In another embodiment of this method, the variant PaS enzyme comprises the amino acid sequence shown in SEQ ID NO: 15 (PaS comprising L325Y mutation). In another embodiment of this method, the variant PaS enzyme comprises the amino acid sequence shown in SEQ ID NO: 57 (PaS comprising A139V/L325W mutations). In another embodiment of this method, the variant PaS enzyme comprises the amino acid sequence shown in SEQ ID NO: 58 (PaS comprising A139V/L325F mutations). In another embodiment of this method, the variant PaS enzyme consists of A139V/L325F amino acid substitutions (SEQ ID NO: 58). In another embodiment of this method, the variant PaS enzyme consists of A139V/R155E/L325W amino acid substitutions (SEQ ID NO: 77).

In another embodiment, the disclosure pertains to a method of hydrolyzing dehydroepiandrosterone 3-sulfate (DHEAS), the method comprising contacting DHEAS with a variant PaS enzyme comprising an amino acid substitution, as compared to the parental PaS enzyme, at an amino acid position corresponding to A139 of SEQ ID NO: 1 (e.g., an A139V substitution), such that hydrolysis of DHEAS occurs. In one embodiment of this method, the variant PaS enzyme comprises the amino acid sequence shown in SEQ ID NO: 6 (PaS comprising an A139V mutation). In another embodiment of this method, the variant PaS enzyme comprises the amino acid sequence shown in SEQ ID NO: 77 (PaS comprising A139V/R155E/L325W mutations). In another embodiment of this method, the variant PaS enzyme comprises the amino acid sequence shown in SEQ ID NO: 114 (PaS comprising A139V/R155E/A323L/L325W mutations). In one embodiment, the range of substrates is in a sample of blood, urine, tissue or meconium obtained from a subject. The methods of the invention can be used on a variety of different bodily samples. Non-limiting examples of suitable bodily samples include blood, urine, tissue or meconium obtained from a subject. Bodily samples can be obtained, stored and prepared for analysis using standard methods well established in the art.

Following hydrolysis by the enzyme, the cleavage products in the sample can be analyzed by standard methodologies, such as high-performance liquid chromatography (HPLC), gas chromatography (GC) and/or mass spectrometry (MS; Stevenson et al. (2015) *Drug Test. Anal.* 7:903-11; Lindner et al. (2017) *J. Pharm. Biomed. Anal.* 142:66-73; Esquivel et al. (2018) *Drug Test Anal.* 10:1734-43; Iannone et al. (2020) *J. Chrom. B* 1155:122280).

The present invention is further illustrated by the following examples, which should not be construed as further limiting. The contents of Sequence Listing, figures and all references, patents and published patent applications cited throughout this application are expressly incorporated herein by reference.

EXAMPLES

Example 1: Gene Synthesis, Cloning, and Protein Expression

The gene for the PaS enzyme was synthesized, placed in a plasmid expression vector, and expressed *E. coli* using standard recombinant DNA techniques established in the art. The DNA sequence coding for a protein sequence can be reconstructed from the protein sequence by standard methods well known in the art. For example, the amino acid sequence for arylsulfatase enzyme from *Pseudomonas aeruginosa* is shown in SEQ ID NO: 1, and can be used to design appropriate DNA sequences coding for the enzymes.

These DNA sequences can be codon optimized for the organism in which they are to be expressed, and linked to appropriate regulatory sequences that enable transcription and translation of the gene and enzyme product. The sequence may include protein sequences known to those skilled in the art that facilitate purification to near homogeneity (Hochuli et al. (1988) *Nature Biotech.* 6:1321-1325). A non-limiting example is the $His_6$-tag, six histidine residues in a row, usually attached to either the N-terminal or C-terminal of an enzyme, which enables specific purification on chromatography resins containing divalent metal cations, such as nickel, cobalt, copper, or zinc.

Typically, the enzyme-encoding DNA sequence is synthesized with consideration for the codon bias of the expression host, an approach also well established in the art (Maloy et al. (1996) *Cold Spring Harbor Lab. Press*; Gouy and Gautier (1982) *Nucleic Acids Res.* 10:22). Using such methods, the gene for PaS enzyme was synthesized with a codon bias compatible for expression in *Escherichia coli* host cells. Using standard molecular biology techniques, the genes were assembled in plasmid vectors under the control of an inducible promoter and expressed in a bacterial strain supportive of the construct. Enzymes were expressed intracellularly, the cells were lysed by a combination of physical and chemical means, and the lysates clarified by centrifugation. The lysates were then adjusted with buffer compatible with subsequent purification steps.

Example 2: Protein Purification of Sulfatase Variants

Figure 3:
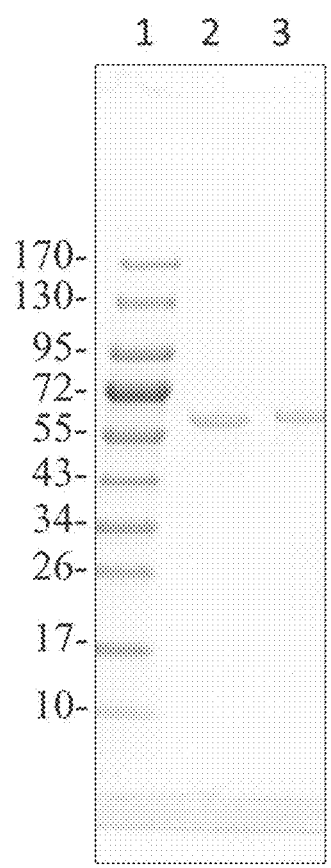
FIG. 3 is a photograph of a 4-20% SDS-PAGE showing purified Pseudomonas aeruginosa arylsulfatase (PaS). Lane 1 is the molecular weight marker (numbers shown in kilodaltons), lane 2 is PaS purified by using Fast Protein Liquid Chromatography (FPLC), and lane 3 is PaS purified by using IMCStips™ tip technologies.

Following recombinant expression, the PaS enzyme and variants described in the Examples were purified by standard immobilized metal affinity chromatography (IMAC) techniques known to those skilled in the art, either on an AKTA™ Pure FPLC or with IMCStips™ tip technologies. Protein elution was monitored by absorbance at 280 nm, protein purity was evaluated by SDS-PAGE (Laemmli (1970) *Nature* 227:680-685), and protein concentration in pure fractions was determined by Bradford protein assay (Bradford (1976) *Anal. Biochem.* 72:248-254) or by the absorbance at 280 nm using the predicted molar extinction coefficient based on the amino acid sequence (Gasteiger et al. (2005) *Prot. Protocols Handbook* 571-607). The SDS-PAGE shown in FIG. 3 revealed purified protein bands of the expected molecular weight, demonstrating effective purification of the recombinant enzymes. Typically a 4-20% gradient SDS-PAGE was used to determine protein purity and about 1.0 µg of protein was used. Protein purity was assessed by using ImageQuantTL 8.1 Software.

Figure 4:
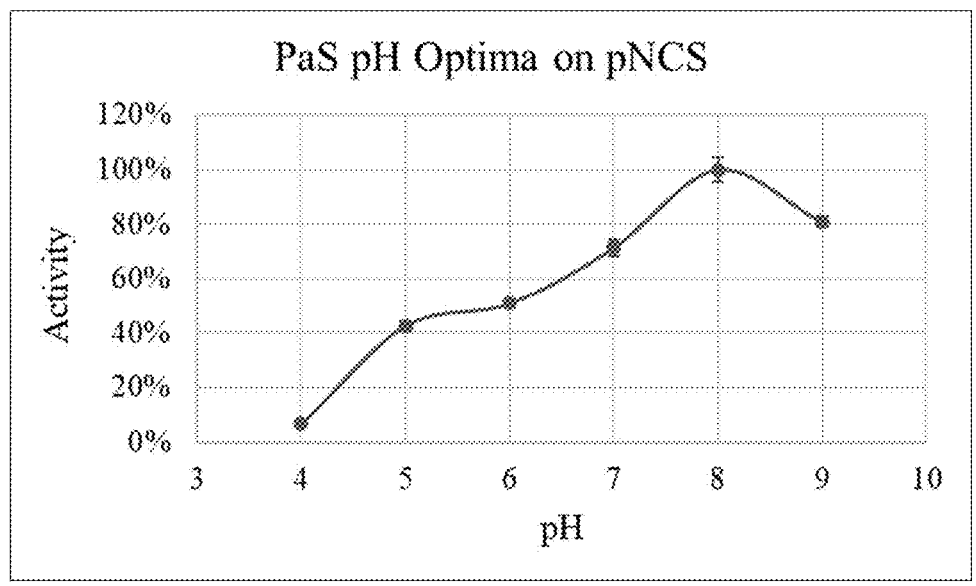
FIG. 4 is a scatterplot showing the pH optima of PaS on p-nitrocatechol sulfate (pNCS) substrate.

Example 3: pH Optima and Enzymatic Activity Measurements Using Various Substrates Activity of recombinant PaS and PaS variants were measured using the substrate p-nitrocatechol sulfate (pNCS), a standard substrate for monitoring and reporting PaS activity (Lee-Vaupel and Conzelmann (1987) *Clinica Chimica Acta* 164:171-180). The pH profile for PaS was determined using a buffer system described in the art (Ellis and Morrison (1982) *Methods Enzymol.* 87:405-426), with p-nitrocatechol sulfate as the substrate. The buffer pH range tested was from pH 4.0-9.0, and the data are shown in FIG. 4. For set up, 25 µL of enzyme and 25 µL of 1.0 mM pNCS were mixed in a 96-well microtiter plate at room temperature, and the reactions were stopped by addition of 150 µL 1.0 M sodium hydroxide. All PaS variants were tested with 1.0 mM pNCS in 50 mM Tris-HCl buffer, pH 8.0.

Additionally, activity of recombinant PaS and PaS variants were measured using the substrate 4-methylumbelliferyl sulfate ester (4MUS). Enzymes were tested with 1.0 mM 4MUS in 50 mM Tris-HCl pH 8.0, 5% ethanol. For set up, 25 µL of enzyme and 25 µL of 1.0 mM 4MUS were mixed in a 96-well microtiter plate at room temperature, and the reactions were stopped by addition of 150 µL 1.0 M sodium hydroxide. Product of 4MUS was measured by excitation wavelength at 360 nm and emission wavelength at 449 nm. All PaS variants were tested with 1.0 mM 4MUS in 50 mM Tris-HCl buffer, pH 8.0 and 5% ethanol.

Example 4: High Pressure Liquid Chromatography, Liquid Chromatography-Mass Spec and Steroid Sulfates In this example, high pressure liquid chromatography (HPLC) and Liquid Chromatography-Mass Spec (LC-MS) was used to measure the activity of PaS and PaS variants on various sulfate ester substrates. Each recombinant arylsulfatase was used to hydrolyze up to four steroid sulfates frequently tested in urine drug-testing applications. The substrates included cortisol 21-sulfate (CS), 17α-estradiol sulfate (αES), boldenone sulfate (BS) and dehydroepiandrosterone 3-sulfate (DHEAS).

For CS, αES, and BS hydrolysis reactions, 5.0 µL of PaS or PaS variant was incubated with 5.0 µL of steroid sulfate at either room temperature or 37° C., depending on the steroid sulfate. The hydrolysis buffer used was 5.0 mM Tris-HCl, pH 8.0. Reactions were stopped by the addition of 50 µL HPLC running buffer containing 41% methanol, 11% acetonitrile, 10 mM potassium phosphate pH 7.6, and 0.1% formic acid.

HPLC was performed on a Thermo-Scientific™ Vanquish™ UHPLC system using a Thermo Scientific™ Accucore™ biphenyl reversed phase 80 Å column (2.1×50 mm, 2.6 µm). The column was heated to 35° C. and used with a flow rate of 0.5 mL/min. Mobile phase used was HPLC running buffer 41% methanol, 11% acetonitrile, 10 mM potassium phosphate, pH 7.6. Each injection of hydrolysis reaction was 25 µL. The system was equilibrated in HPLC running buffer for 5-10 minutes prior to use. The absorbance was measured at 250 nm for CS and BS, and 280 nm for αES.

Data were plotted as significance (negative logarithm base 10 of p-value) versus change in activity (logarithm base 2 change in activity relative to template). A horizontal dashed line at the logarithm base 10 of 0.05 is used to distinguish data is that has a significant change, i.e. the p-value<0.05; any data plotted above this line are considered significant.

For DHEAS, LC-MS was used to measure the activity of PaS and PaS variants. Enzyme concentrations were normalized to 0.08 mg/mL in 10 mM Tris-HCl, pH 8.0. Unhydrolyzed controls, DHEAS and DHEA, were diluted as molar equivalents to 10% methanol (MeOH) at 0.10 and 0.73 mg/mL, respectively. Reactions contained 15 µL of enzyme mixed with 15 µL of DHEAS and 60 µL of 10 mM Tris-HCl, 10% MeOH, pH 8.0. Reactions were incubated at 37° C. for various times, depending on the variants being tested. Samples were quenched with 470 µL running buffer containing internal standard (41% MeOH, 11% acetonitrile, 0.5% DHEA-D5, 0.1% formic acid). Protein was removed from samples using a Phenomenex β-Gone PLUS plate by centrifuging at 500×g for 1 minute.

LC-MS was performed on a Thermo-Scientific™ Vanquish™ UHPLC system using a Thermo-Scientific™ Accucore™ Biphenyl Reversed Phase column (2.1×50 mm, 2.6 μm). The column was heated to 40° C. with a gradient elution with a flow rate of 0.6 mL/min. Mobile phase A consisted of 0.1% formic acid in ultrapure water and mobile phase B consisted of 100% MeOH. The system was equilibrated in 60% A and 40% B. The liquid chromatography (LC) system was connected to a Thermo-Scientific™ Endura™ Triple Quadrupole mass spectrometer with an electrospray ionization source, operated in positive mode for DHEA and DHEA-D5 and negative mode for DHEAS.

Data were plotted as significance (negative logarithm base 10 of p-value) versus change in activity (logarithm base 2 change in activity relative to template). A horizontal dashed line at the logarithm base 10 of 0.05 is used to distinguish data is that has a significant change, i.e. the p-value<0.05; any data plotted above this line are considered significant.

Example 5: Mutagenesis of Key Residues in Sulfatase

Figure 2:
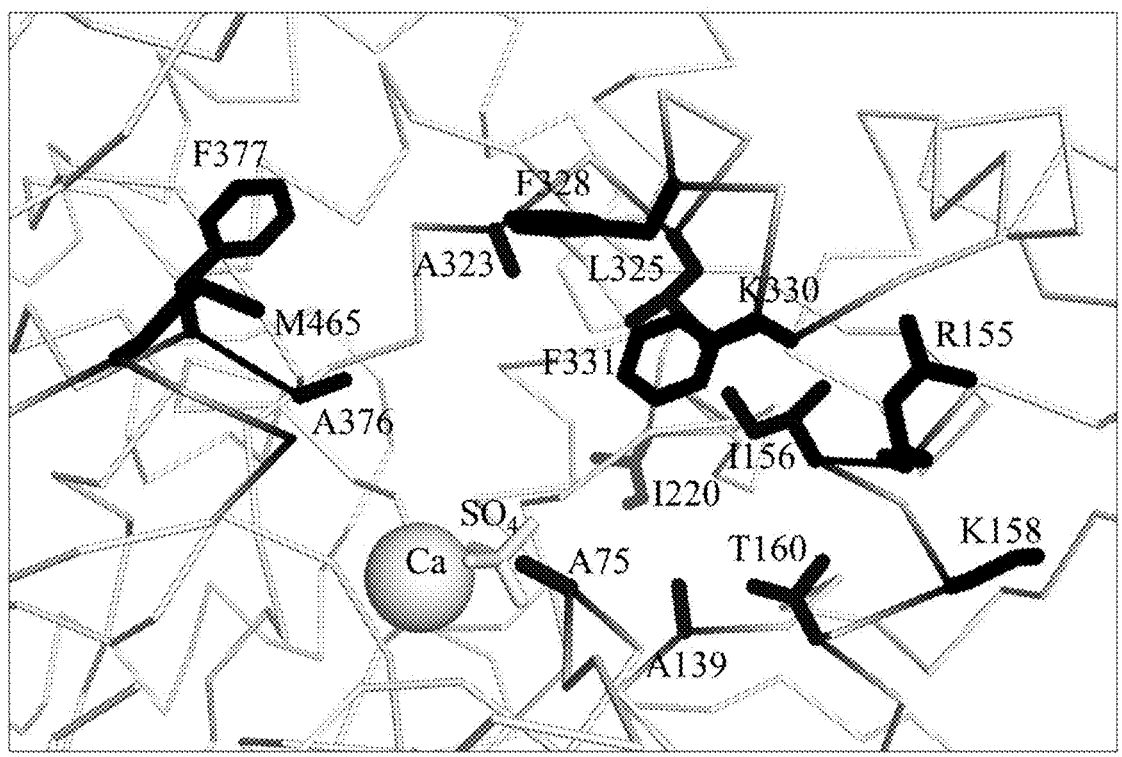
FIG. 2 shows a depiction of the active site of the arylsulfatase structure from Pseudomonas aeruginosa with key residues highlighted and labeled (protein data bank code: 1HDH).

In this example, key residues within the PaS enzyme sequence were selected for site-saturation mutagenesis (SSM) (FIG. 1). This is a method whereby all possible amino acid substitutions are made at a single residue site using degenerate oligonucleotides. Oligonucleotides were designed so that only one codon was used for each possible amino acid (Pines et al. (2014) ACS Synth. Bio. 4:604-614). Variants were produced by performing SSM or site-directed mutagenesis (SDM) on the following key residues or combinations thereof: A75, A139, R155, I156, K158, T160, I220, A323, L325, F328, K330, F331, A376, F377 and M465. These key residue positions for mutagenesis are highlighted in FIG. 1. The position of these residues in the PaS crystal structure are shown in FIG. 2.

Over 90 clones from each site-saturation mutagenesis library of each key residue were screened for activity to ensure that every possible amino acid was tested at each site. At this level of coverage, statistical calculations predict a >99% chance that each amino acid would be screened at least once. Furthermore, 10 random clones were sequenced for each round of SSM to ensure there was no codon bias during the mutagenesis reactions, i.e. that one codon did not occur significantly more than other codons.

Active clones were initially selected by plating them on LB-agar plates containing 5-bromo-4-chloro-3-indoxyl sulfate (X-Sulf) where active arylsulfatase clones produce a blue pigment in the colonies (van Loo et al. (2019) ACS Synth. Biol. 8:2690-700). Active clones from X-Sulf screening were selected and characterized by an in vivo assay using the fluorescent substrate 4-methylumbelliferyl sulfate ester (4MUS). This assay was performed by growing the clones for about 16 hours at 37° C. in a 96-well plate where each well contains the appropriate anti-biotic and 150 μL of LB with shaking at 300 RPM. Next, 150 μL of media containing isopropyl β-d-1-thiogalactopyranoside (0.2 mM), glucose (1.2%), and glycerol (0.8%) was added to the 96-well plate and the cells incubated for 3-4 hours at 37° C. and 300 RPM. After expression induction, the optical density ($OD_{600}$) of the cells was determined by measuring the absorbance at 600 nm. The activity assay was performed by mixing 25 μL of cells with 25 μL of substrate, incubating the reactions at room temperature for 5-10 minutes, then stopping the reactions with the addition of 150 μL 1.0 M sodium hydroxide. The stock concentration of 4MUS was 1.0 mM in 10% EtOH and 100 mM Tris-HCl, pH 8.0. The product of 4MUS was measured by excitation at 360 nm and emission at 449 nm. Activity was calculated as arbitrary fluorescent units (AFU) per minute per OD. The 10 most active variants were selected for plasmid isolation and DNA sequencing.

In addition to selection by in vivo 4MUS screening, PaS variants discovered during the codon bias check that were non-redundant with those determined from the in vivo assay were also characterized. Furthermore, certain mutations warranted further investigation by rational design, such that if the mutation resulted in increased activity or altered substrate specificity, the key residue may have also been mutated into a similar residue that shares characteristics (i.e. hydrophobic, aliphatic, or charged) of the mutated residue.

Example 6: Point Mutation at Residue Position A139

Figure 5:
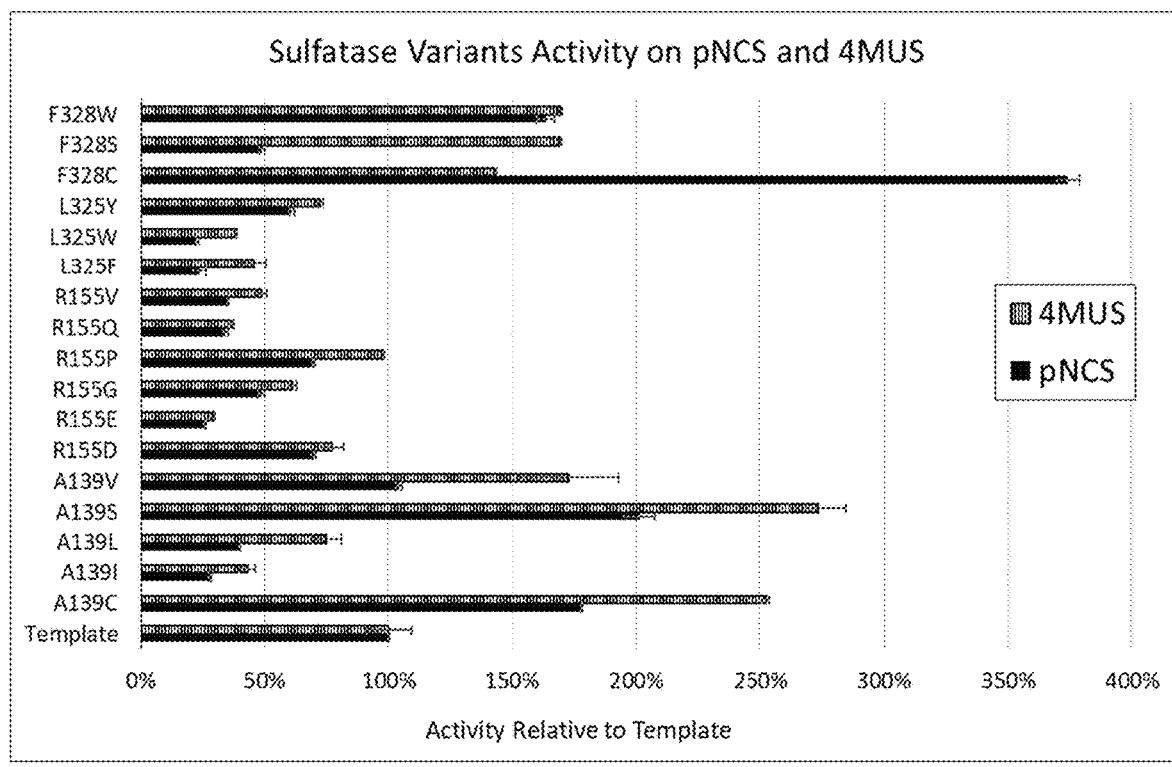
FIG. 5 is a bar graph depicting sulfatase variants A139X, R155X, L325X and F328X enzyme activities on pNCS (p-nitrocatechol sulfate) and 4-methylumbelliferyl sulfate (4MUS) substrates.

In this example, the amino acid residue A139 highlighted in FIG. 1 was mutated and the enzymatic activity of the variants tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 5. The results for steroid sulfatase hydrolysis are shown in FIGS. 10-12 and 24. In FIGS. 10-12 and 24, variants indicated in the upper right quadrant of the graph exhibited increased activity as compared to template (p-value<0.05).

In summary, the results from FIGS. 10-12 and 24 demonstrate that the following PaS single point variants exhibited enhanced enzymatic activity against at least one, and often multiple, substrates as compared to the template from which the variant was derived: A139C, A139I, A139L, A139S, A139V, the amino acid sequences of which are shown in SEQ ID NOs: 2-6, respectively.

Figure 10:
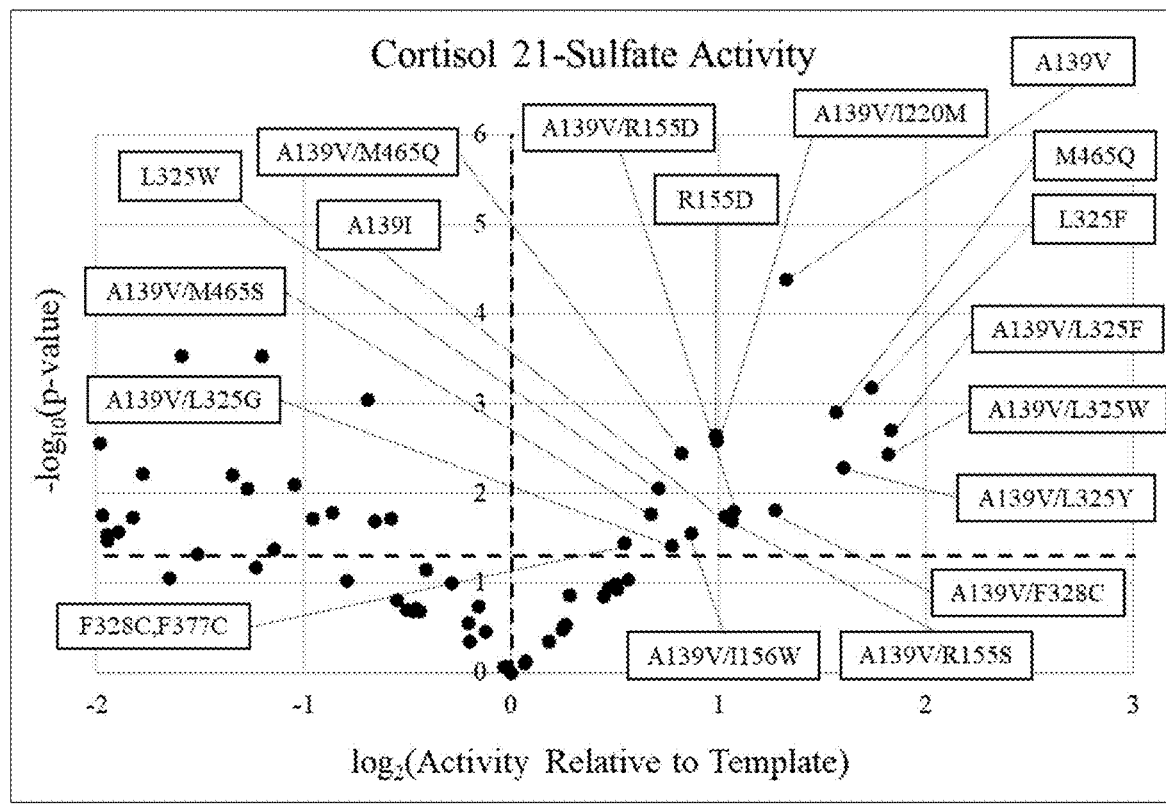
FIG. 10 is a graph showing the significant enzymatic activity of sulfatase variants A139X, R155X, L325X, F328X, K330T, A376X, F377X, M465X, A139V/R155X, A139V/I156X, A139V/L325X, A139V/F328X, A139V/K330X, A139V/M465X, L325Y/I220M, R155E/I220M and A139V/I220M on cortisol 21-sulfate (CS).
Figure 12:
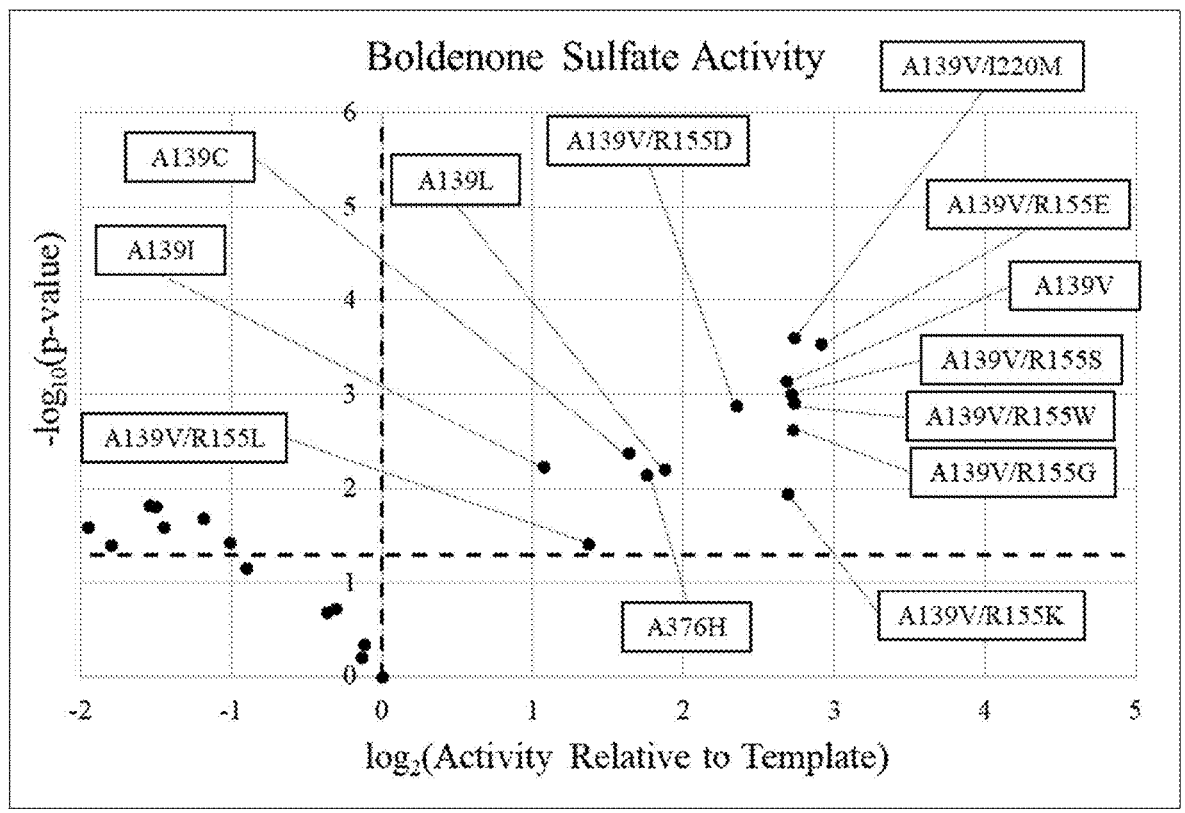
FIG. 12 is a graph showing the significant enzymatic activity of sulfatase variants A139X, F328X, A376X, F377X, M465X, A139V/R155X, A139V/I220M on boldenone sulfate (BS).

Moreover, the data shown in FIG. 10, FIG. 12 and FIG. 24 demonstrates that the A139V variant showed exceptionally high enzymatic activity against the cortisol 21-sulfate (CS), boldenone sulfate (BS) and dehydroepiandrosterone 3-sulfate (DHEAS) substrates as compared to the parental PaS enzyme.

Example 7: Point Mutation at Residue Position R155

Figure 11:
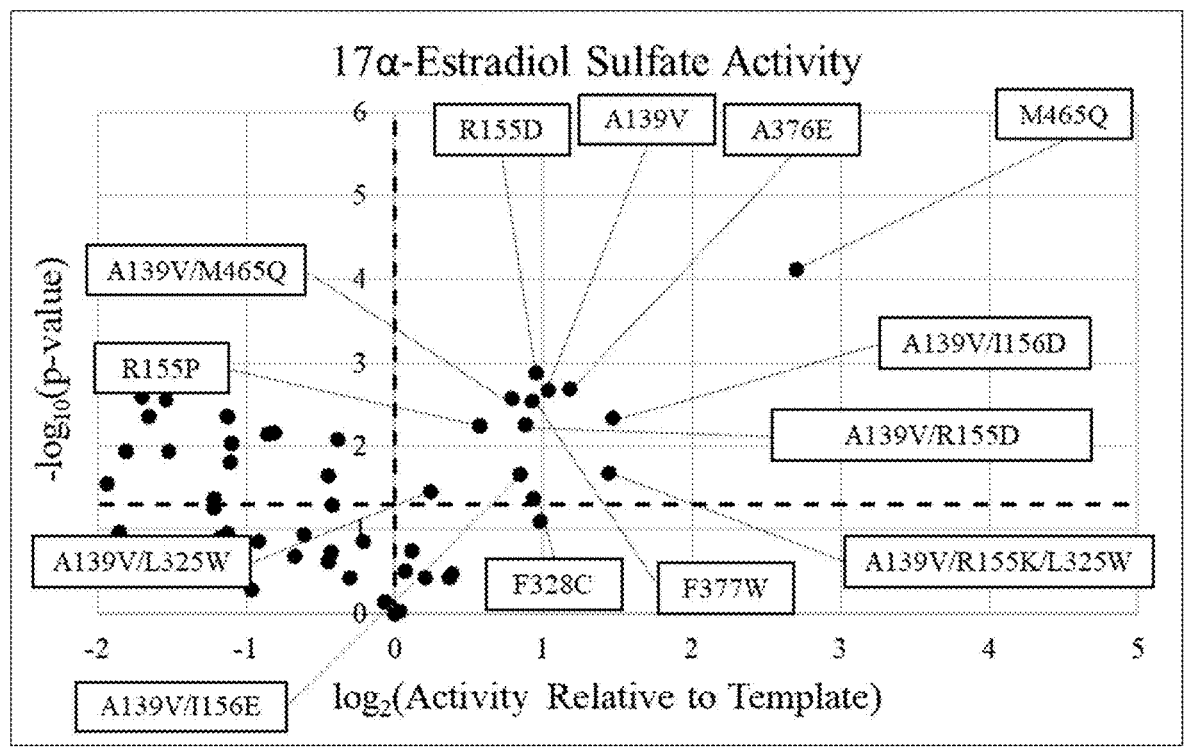
FIG. 11 is a graph showing the significant enzymatic activity of sulfatase variants A139X, R155X, L325X, F328X, K330T, A376X, F377X, M465X, A139V/R155X, A139V/I156X, A139V/L325X, A139V/F328X, A139V/K330X, A139V/M465X, L325Y/I220M, R155E/I220M and A139V/I220M on 17α-estradiol sulfate (αES).
Figure 14:
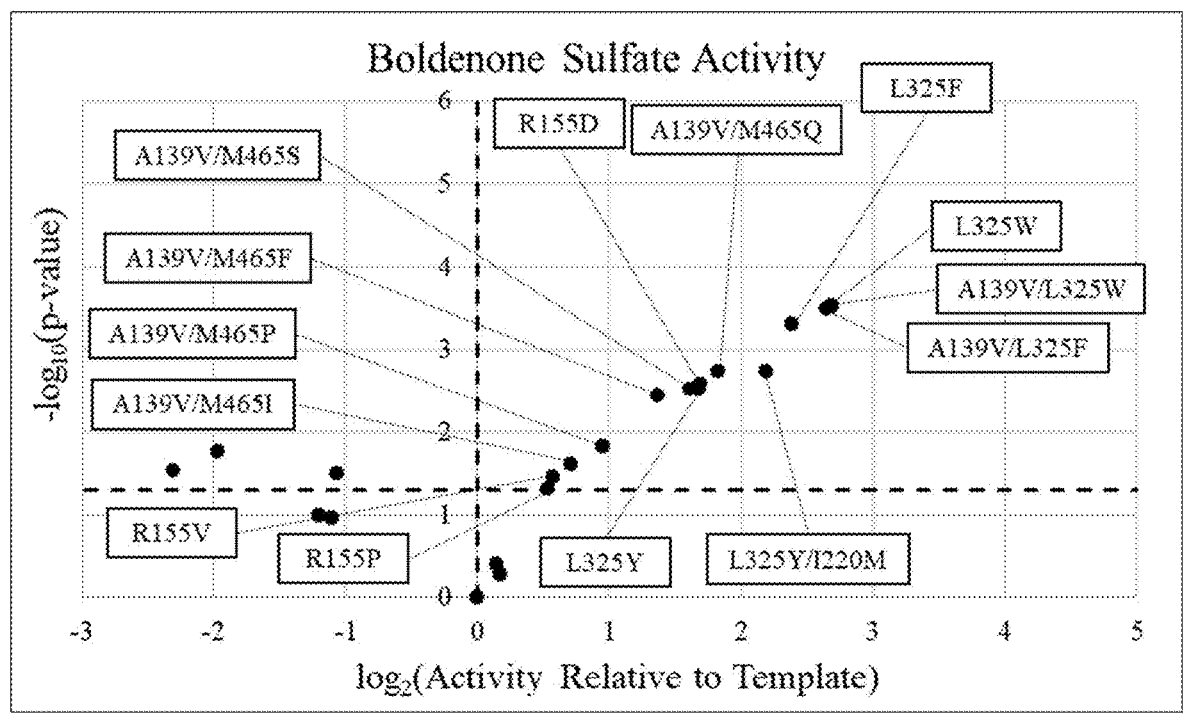
FIG. 14 is a graph showing the significant enzymatic activity of sulfatase variants A139V/M465X, K330T, L325X, L325Y/I220M, R155X, R155/I220M, A139V/L325F, A139V/L325W and A139V/M465X on boldenone sulfate (BS).

In this example, the amino acid residue R155 highlighted in FIG. 1 was mutated and the enzymatic activity of the variants tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 5. The results for steroid sulfatase hydrolysis are shown in FIGS. 10, 11 and 14. In FIGS. 10, 11 and 14, variants indicated in the upper right quadrant of the graph exhibited increased activity as compared to template (p-value<0.05).

In summary, the results from FIGS. 10, 11 and 14 demonstrate that the following PaS single point variants exhibited enhanced enzymatic activity against at least one, and often multiple, substrates as compared to the template from which the variant was derived: R155D, R155E, R155G, R155P, R155Q, R155V, the amino acid sequences of which are shown in SEQ ID NOs: 7-12, respectively.

Example 8: Point Mutation at Residue Position L325

In this example, the amino acid residue L325 highlighted in FIG. 1 was mutated and the enzymatic activity of the variants tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 5. The results for steroid sulfatase hydrolysis are shown in FIGS. 10, 11,14 and 24. In FIGS. 10, 11, 14 and 24, variants indicated in the upper right quadrant of the graph exhibited increased activity as compared to template (p-value<0.05).

In summary, the results from FIGS. 10, 11, 14 and 24 demonstrate that the following PaS single point variants exhibited enhanced enzymatic activity against at least one, and often multiple, substrates as compared to the template from which the variant was derived: L325F, L325W, L325Y, the amino acid sequences of which are shown in SEQ ID NOs: 13-15, respectively.

Moreover, the data shown in FIG. 10, FIG. 14 and FIG. 24 demonstrates that the L325F and L325W variants showed exceptionally high enzymatic activity against the cortisol 21-sulfate (CS), boldenone sulfate (BS) and dehydroepiandrosterone 3-sulfate (DHEAS) substrates as compared to the parental PaS enzyme. In addition, the data shown in FIG. 14 and FIG. 24 demonstrate that the L325Y and L325F variants showed exceptionally high enzymatic activity against the boldenone sulfate (BS) and dehydroepiandrosterone 3-sulfate (DHEAS) substrates, respectively, as compared to the parental PaS enzyme.

Example 9: Point Mutation at Residue Position F328

In this example, the amino acid residue F328 highlighted in FIG. 1 was mutated and the enzymatic activity of the variants tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 5. The results for steroid sulfatase hydrolysis are shown in FIGS. 10-12 and 24. In FIGS. 10-12 and 24, variants indicated in the upper right quadrant of the graph exhibited increased activity as compared to template (p-value<0.05).

In summary, the results from FIGS. 10-12 and 24 demonstrate that the following PaS single point variants exhibited enhanced enzymatic activity against at least one, and often multiple, substrates as compared to the template from which the variant was derived: F328C, F328S, F328W, the amino acid sequences of which are shown in SEQ ID NOs: 16-18, respectively.

Example 10: Point Mutation at Residue Position K330

Figure 6:
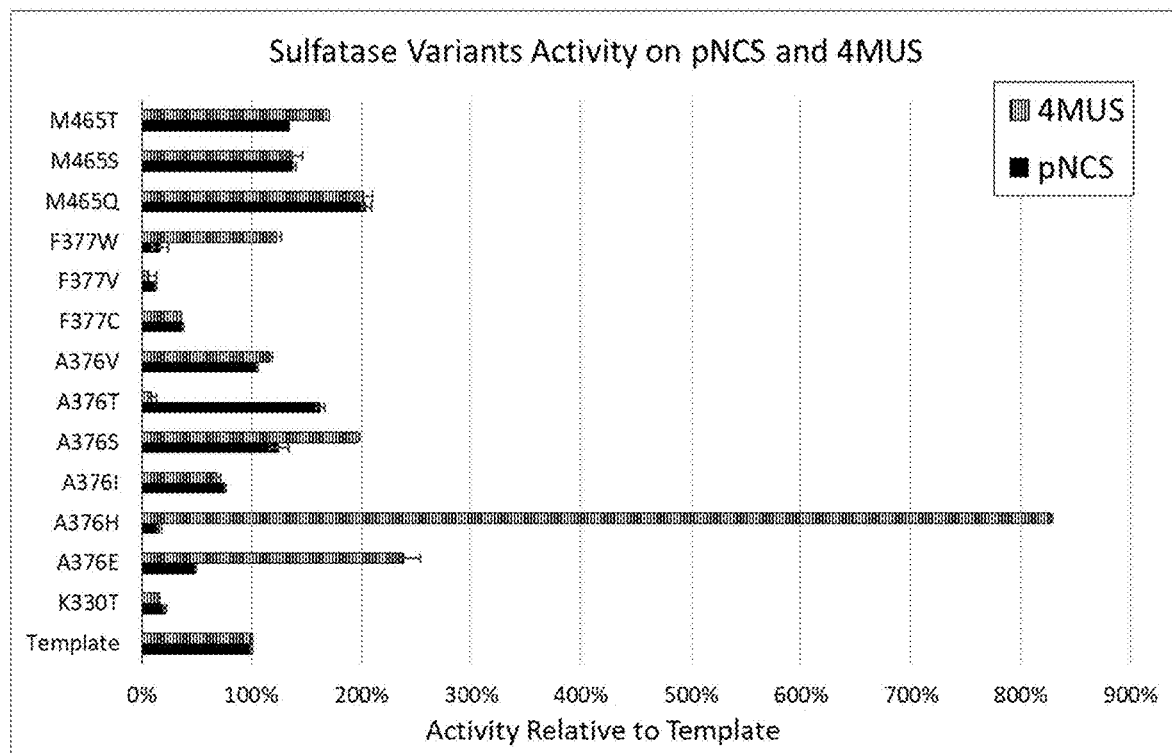
FIG. 6 is a bar graph depicting sulfatase variants K330T, A376X, F377X and M465X enzyme activities on pNCS (p-nitrocatechol sulfate) and 4-methylumbelliferyl sulfate (4MUS) substrates.

In this example, the amino acid residue K330 highlighted in FIG. 1 was mutated and the enzymatic activity of the variants tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 6. The results for steroid sulfatase hydrolysis are shown in FIGS. 10, 11 and 14. In FIGS. 10, 11 and 14, variants indicated in the upper right quadrant of the graph exhibited increased activity as compared to template (p-value<0.05).

In summary, the results from FIGS. 10, 11 and 14 demonstrate that the following PaS single point variant exhibited enhanced enzymatic activity against at least one, and often multiple, substrates as compared to the template from which the variant was derived: K330T, the amino acid sequence of which is shown in SEQ ID NO: 19, respectively.

Example 11: Point Mutation at Residue Position A376

In this example, the amino acid residue A376 highlighted in FIG. 1 was mutated and the enzymatic activity of the variants tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 5. The results for steroid sulfatase hydrolysis are shown in FIGS. 10-12 and 24. In FIGS. 10-12 and 24, variants indicated in the upper right quadrant of the graph exhibited increased activity as compared to template (p-value<0.05).

In summary, the results from FIGS. 10-12 and 24 demonstrate that the following PaS single point variants exhibited enhanced enzymatic activity against at least one, and often multiple, substrates as compared to the template from which the variant was derived: A376E, A376H, A376I, A376S, A376T, A376V, the amino acid sequences of which are shown in SEQ ID NOs: 20-25, respectively.

Example 12: Point Mutation at Residue Position F377

In this example, the amino acid residue F377 highlighted in FIG. 1 was mutated and the enzymatic activity of the variants tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 5. The results for steroid sulfatase hydrolysis are shown in FIG. 10-12. In FIG. 10-12, variants indicated in the upper right quadrant of the graph exhibited increased activity as compared to template (p-value<0.05).

In summary, the results from FIG. 10-12 demonstrate that the following PaS single point variants exhibited enhanced enzymatic activity against at least one, and often multiple, substrates as compared to the template from which the variant was derived: F377C, F377V, F377W, the amino acid sequences of which are shown in SEQ ID NOs: 26-28, respectively.

Example 13: Point Mutation at Residue Position M465

In this example, the amino acid residue M465 highlighted in FIG. 1 was mutated and the enzymatic activity of the variants tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 5. The results for steroid sulfatase hydrolysis are shown in FIGS. 10-12 and 24. In FIGS. 10-12 and 24, variants indicated in the upper right quadrant of the graph exhibited increased activity as compared to template (p-value<0.05).

In summary, the results from FIGS. 10-12 and 24 demonstrate that the following PaS single point variants exhibited enhanced enzymatic activity against at least one, and often multiple, substrates as compared to the template from which the variant was derived: M465Q, M465S, M465T, the amino acid sequences of which are shown in SEQ ID NOs: 29-31, respectively.

Moreover, the data shown in FIG. 11 and FIG. 24 demonstrates that the M465Q variant showed exceptionally high enzymatic activity against the 17α-estradiol sulfate (αES) and dehydroepiandrosterone 3-sulfate (DHEAS) substrates as compared to the parental PaS enzyme.

Example 14: Double Point Mutation Variant A139/R155

Figure 7:
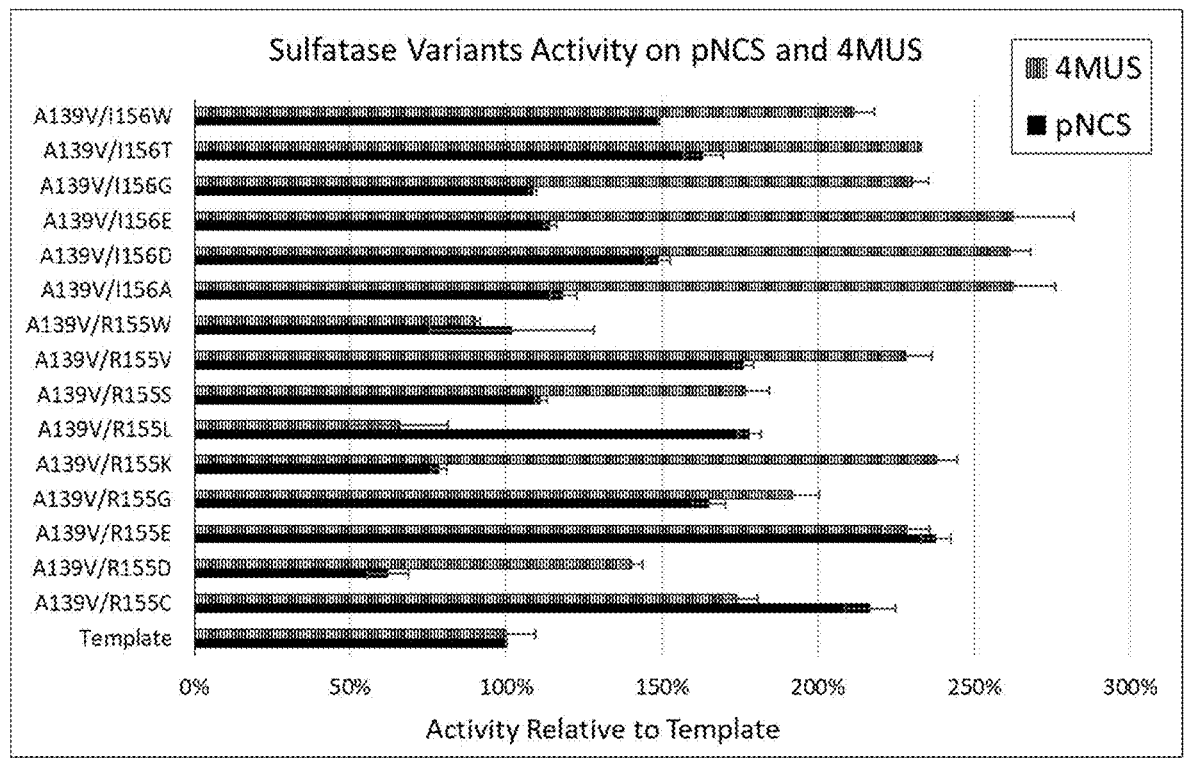
FIG. 7 is a bar graph depicting sulfatase variants A139V/R155X and A139V/I156X enzyme activities on pNCS and 4MUS substrates.

In this example, two point mutations were made at various combinations of amino acid residues shown in FIG. 1, and the enzymatic activity of the double point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 7. The results for the A139/R155 variants on a panel of steroid sulfate substrates are shown in FIG. 10-12. In FIG. 10-12, variants indicated in the upper right quadrant of the graph exhibited increased activity as compared to template.

In summary, the results from FIG. 10-12 demonstrate that the following PaS A139/R155 double point variants exhibited enhanced enzymatic activity against at least one, and often multiple, substrates as compared to the template from which the variant was derived: A139V/R155C, A139V/R155D, A139V/R155E, A139V/R155G, A139V/R155K, A139V/R155L, A139V/R155S, A139V/R155V, A139V/R155W, the amino acid sequences of which are shown in SEQ ID NOs: 32-40.

Moreover, the data shown in FIG. 12 demonstrates that the A139V/R155E variant showed exceptionally high enzymatic activity against the boldenone sulfate (BS) substrate as compared to the parental PaS enzyme.

Example 15: Double Point Mutation Variant A139/I156

Figure 13:
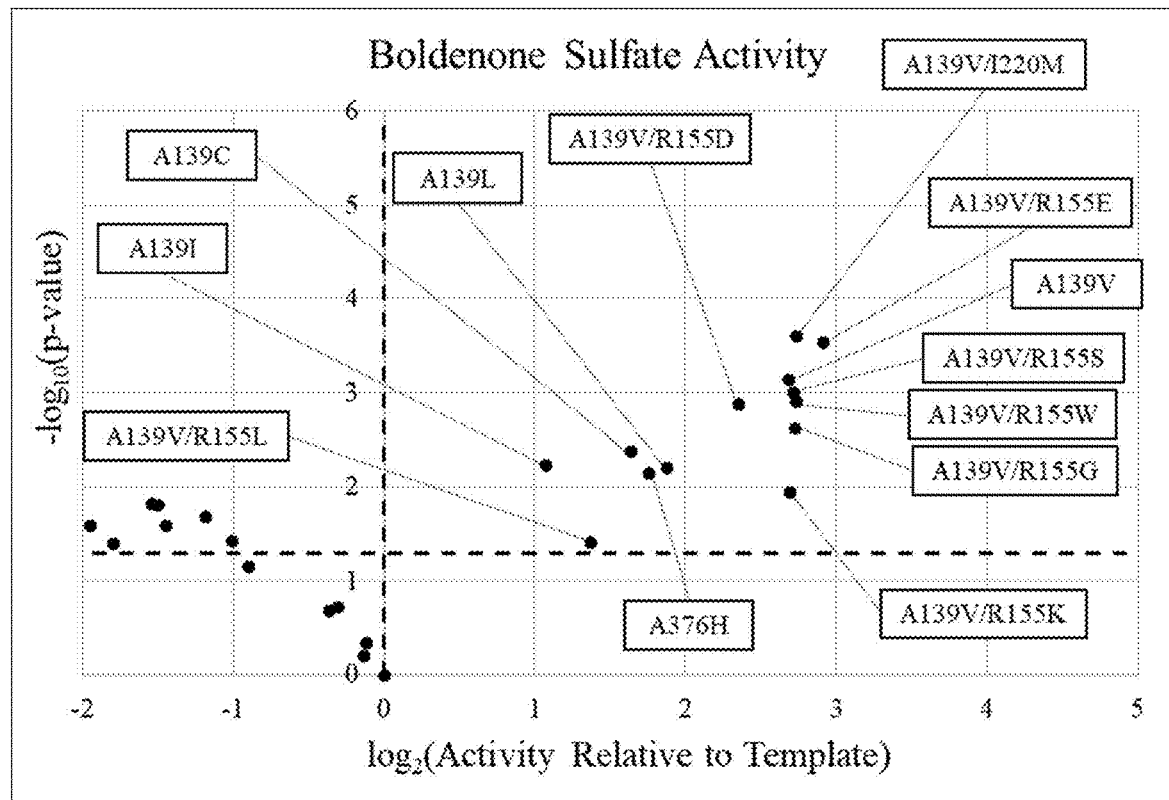
FIG. 13 is a graph showing the significant enzymatic activity of sulfatase variants A139V/I156X, A139V/L325X, A139V/F328X, and A139V/K330X on boldenone sulfate.

In this example, two point mutations were made at various combinations of amino acid residues shown in FIG. 1, and the enzymatic activity of the double point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 7. The results for the A139/I156 variants on a panel of steroid sulfate substrates are shown in FIGS. 10, 11 and 13. In FIGS. 10, 11 and 13, variants indicated in the upper right quadrant of the graph exhibited increased activity as compared to template.

In summary, the results from FIGS. 10, 11 and 13 demonstrate that the following PaS A139/I156 double point variants exhibited enhanced enzymatic activity against at least one, and often multiple, substrates as compared to the template from which the variant was derived: A139V/I156A, A139V/I156D, A139V/I156E, A139V/I156G, A139V/I156T, A139V/I156W, the amino acid sequences of which are shown in SEQ ID NOs: 42-47.

Example 16: Double Point Mutation Variant A139/L325

Figure 8:
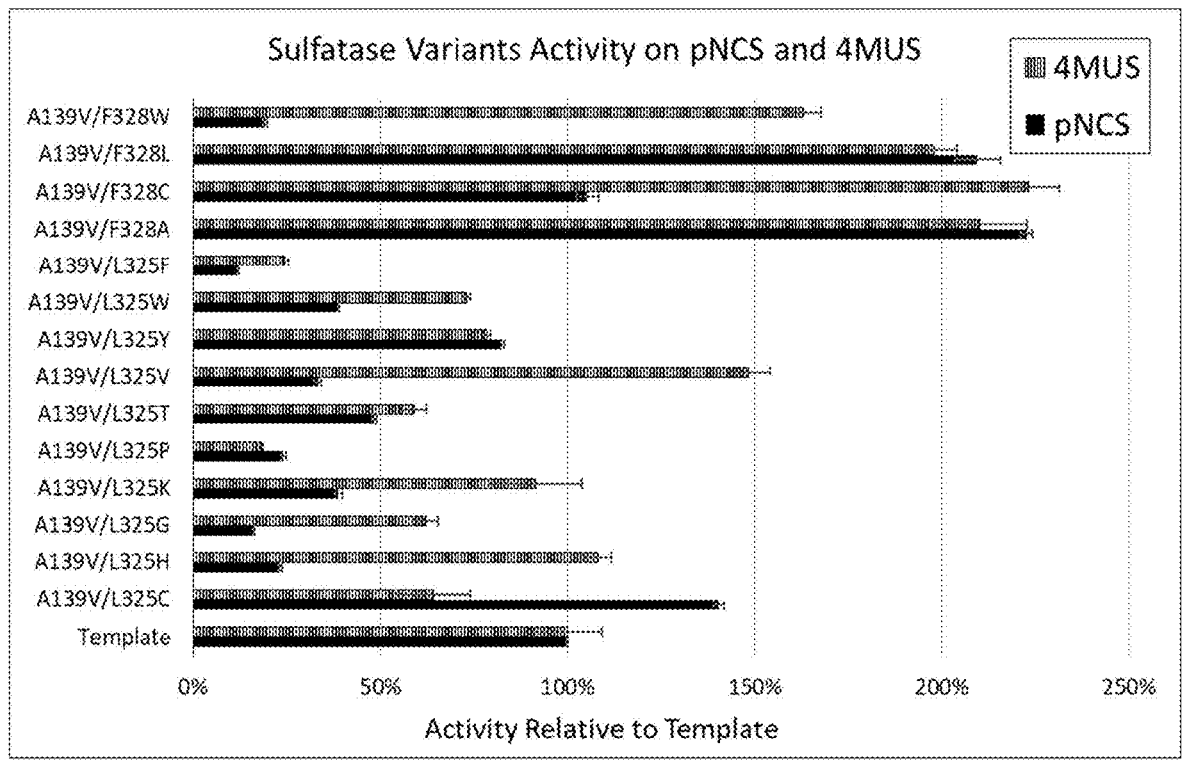
FIG. 8 is a bar graph depicting sulfatase variants A139V/L325X and A139V/F328X enzyme activities on pNCS and 4MUS substrates.

In this example, two point mutations were made at various combinations of amino acid residues shown in FIG. 1, and the enzymatic activity of the double point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 8. The results for the A139/L325 variants on a panel of steroid sulfate substrates are shown in FIGS. 10, 11, 13 and 14. In FIGS. 10, 11, 13 and 14, variants indicated in the upper right quadrant of the graph exhibited increased activity as compared to template.

In summary, the results from FIGS. 10, 11, 13 and 14 demonstrate that the following PaS A139/L325 double point variants exhibited enhanced enzymatic activity against at least one, and often multiple, substrates as compared to the template from which the variant was derived: A139V/L325C, A139V/L325H, A139V/L325G, A139V/L325K, A139V/L325P, A139V/L325T, A139V/L325V, A139V/L325Y, A139V/L325W, A139V/L325F, the amino acid sequences of which are shown in SEQ ID NOs: 49-58.

Moreover, the data shown in FIG. 10 demonstrates that the A139V/L325W and A139V/L325F variants showed exceptionally high enzymatic activity against the cortisol sulfate (CS) substrate as compared to the parental PaS enzyme. In addition, the data shown in FIGS. 13 and 14 demonstrates that A139V/L325F, A139V/L325W and A139V/L325Y variants showed exceptionally high enzymatic activity against the boldenone sulfate (BS) substrate as compared to the parental PaS enzyme.

Example 17: Double Point Mutation Variant A139/F328

In this example, two point mutations were made at various combinations of amino acid residues shown in FIG. 1, and the enzymatic activity of the double point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 8. The results for the A139/F328 variants on a panel of steroid sulfate substrates are shown in FIGS. 10, 11 and 13. In FIGS. 10, 11 and 13, variants indicated in the upper right quadrant of the graph exhibited increased activity as compared to template.

In summary, the results from FIGS. 10, 11 and 13 demonstrate that the following PaS A139/F328 double point variants exhibited enhanced enzymatic activity against at least one, and often multiple, substrates as compared to the template from which the variant was derived: A139V/F328A, A139V/F328C, A139V/F328L, A139V/F328W, the amino acid sequences of which are shown in SEQ ID NOs: 60-63.

Example 18: Double Point Mutation Variant A139/K330

Figure 9:
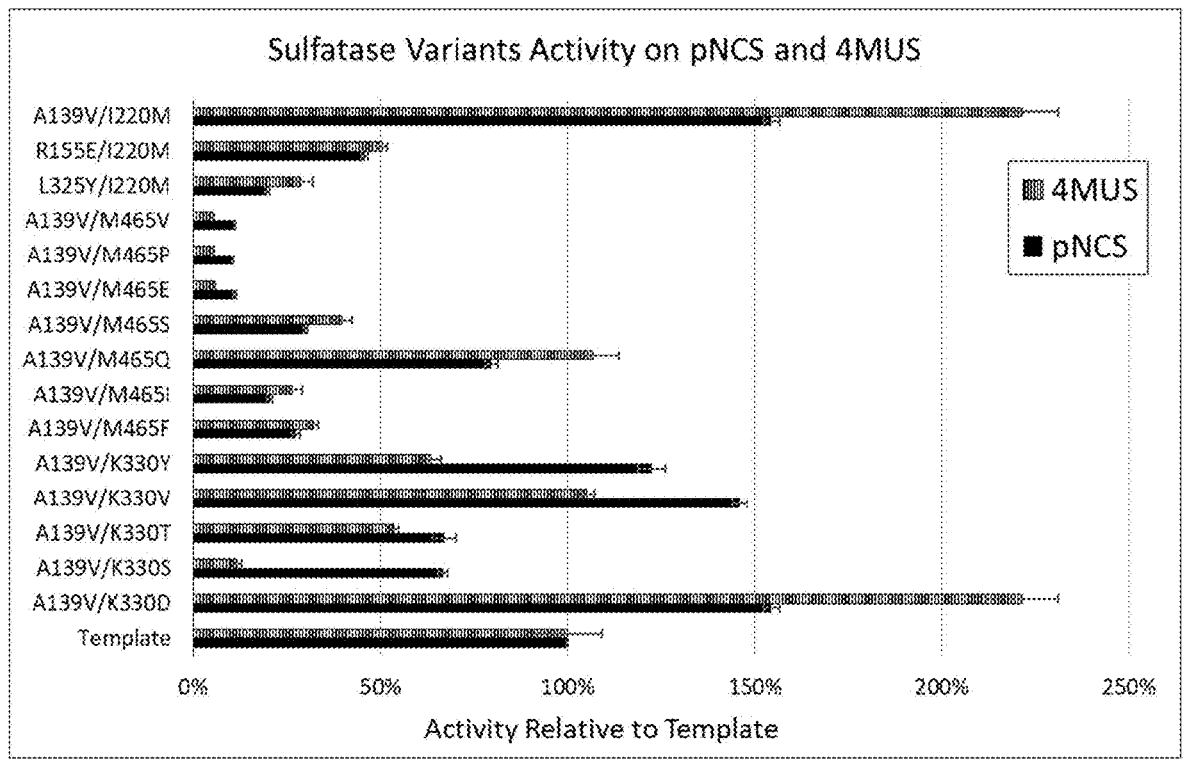
FIG. 9 is a bar graph depicting sulfatase variants A139V/K330X, A139V/M465X, L325Y/I220M, R155E/I220M and A139V/I220M enzyme activities on pNCS and 4MUS substrates.

In this example, two point mutations were made at various combinations of amino acid residues shown in FIG. 1, and the enzymatic activity of the double point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 9. The results for the A139/K330 variants on a panel of steroid sulfate substrates are shown in FIGS. 10, 11 and 13. In FIGS. 10, 11 and 13, variants indicated in the upper right quadrant of the graph exhibited increased activity as compared to template.

In summary, the results from FIGS. 10, 11 and 13 demonstrate that the following PaS A139/K330 double point variants exhibited enhanced enzymatic activity against at least one, and often multiple, substrates as compared to the template from which the variant was derived: A139V/K330D, A139V/K330S, A139V/K330T, A139V/K330V, A139V/K330Y, the amino acid sequences of which are shown in SEQ ID NOs: 64-68.

Example 19: Double Point Mutation Variant A139/M465

In this example, two point mutations were made at various combinations of amino acid residues shown in FIG. 1, and the enzymatic activity of the double point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 9. The results for the A139/M465 variants on a panel of steroid sulfate substrates are shown in FIGS. 10, 11 and 14. In FIGS. 10, 11 and 14, variants indicated in the upper right quadrant of the graph exhibited increased activity as compared to template.

In summary, the results from FIGS. 10, 11 and 14 demonstrate that the following PaS A139/M465 double point variants exhibited enhanced enzymatic activity against at least one, and often multiple, substrates as compared to the template from which the variant was derived: A139V/M465F, A139V/M465I, A139V/M465Q, A139V/M465S, A139V/M465E, A139V/M465P, A139V/M465V, the amino acid sequences of which are shown in SEQ ID NOs: 69-75.

Example 20: Double Point Mutation Variant A139/I220

In this example, two point mutations were made at various combinations of amino acid residues shown in FIG. 1, and the enzymatic activity of the double point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 9. The results for the A139/I220 variant on a panel of steroid sulfate substrates are shown in FIG. 10-12. In FIG. 10-12, variants indicated in the upper right quadrant of the graph exhibited increased activity as compared to template.

In summary, the results from FIG. 10-12 demonstrate that the following PaS A139/I220 double point variant exhibited enhanced enzymatic activity against at least one, and often multiple, substrates as compared to the template from which the variant was derived: A139V/I220M, the amino acid sequence of which is shown in SEQ ID NO: 48.

Example 21: Double Point Mutation Variant R155/I220

In this example, two point mutations were made at various combinations of amino acid residues shown in FIG. 1, and the enzymatic activity of the double point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 9. The results for the R155/I220 variant on a panel of steroid sulfate substrates are shown in FIGS. 10, 11 and 14. In FIGS. 10, 11 and 14, variants indicated in the upper right quadrant of the graph exhibited increased activity as compared to template.

In summary, the results from FIGS. 10, 11 and 14 demonstrate that the following PaS R155/I220 double point variant exhibited enhanced enzymatic activity against at least one, and often multiple, substrates as compared to the template from which the variant was derived: R155E/I220M, the amino acid sequence of which is shown in SEQ ID NO: 41.

Example 22: Double Point Mutation Variant L325/I220

In this example, two point mutations were made at various combinations of amino acid residues shown in FIG. 1, and the enzymatic activity of the double point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) at pH 8.0. The results using these variants, as compared to template, with the pNCS and 4MUS substrates are shown in FIG. 9. The results for the L325/I220 variant on a panel of steroid sulfate substrates are shown in FIGS. 10, 11 and 14. In FIGS. 10, 11 and 14, variants indicated in the upper right quadrant of the graph exhibited increased activity as compared to template.

In summary, the results from FIGS. 10, 11 and 14 demonstrate that the following PaS L325/I220 double point variant exhibited enhanced enzymatic activity against at least one, and often multiple, substrates as compared to the template from which the variant was derived: L325Y/I220M, the amino acid sequence of which is shown in SEQ ID NO: 59.

Example 23: Triple Point Mutation Variant A139/R155/L325

Figure 15:
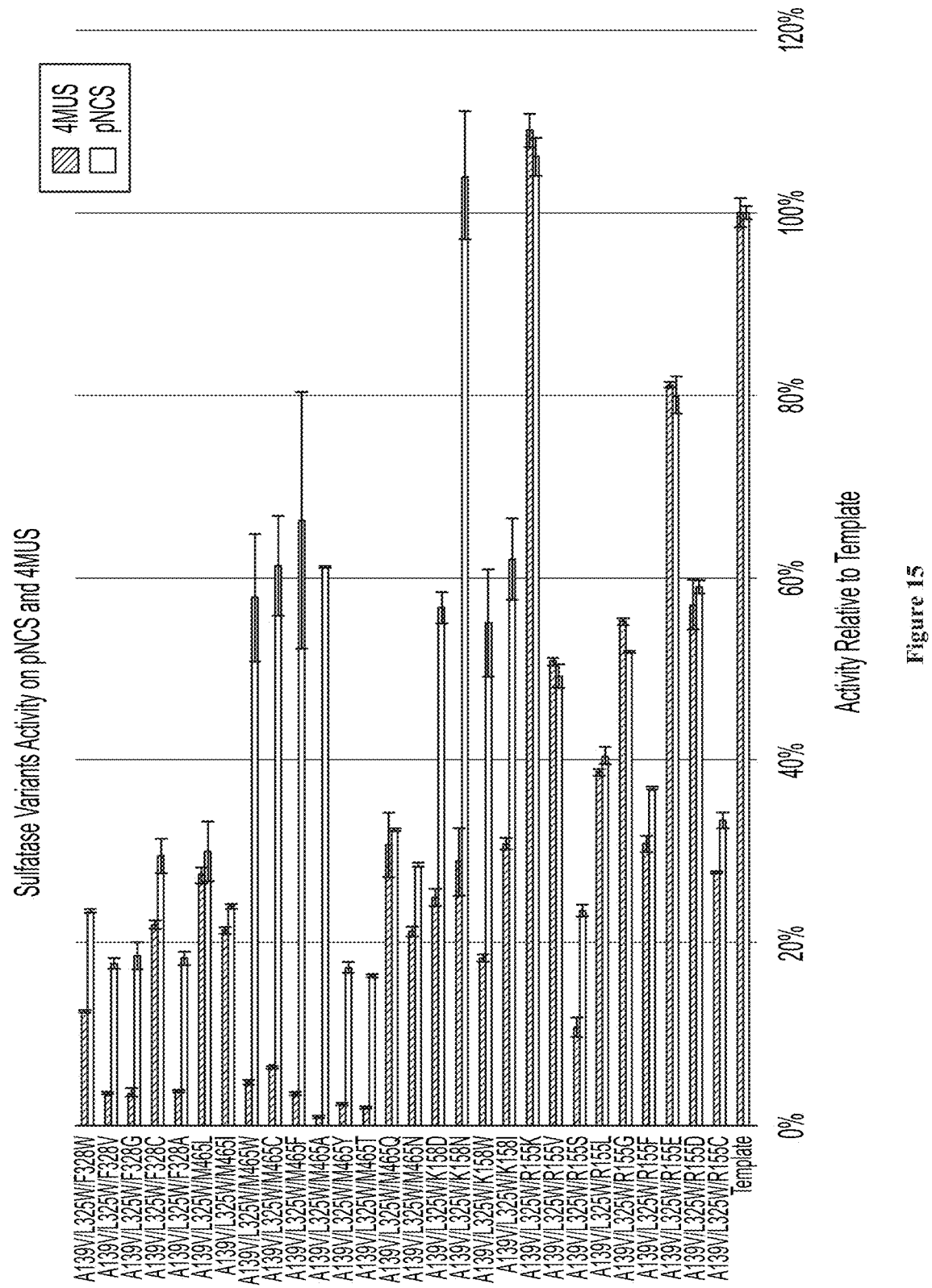
FIG. 15 is a bar graph depicting sulfatase variants A139V/L325W/R155X, A139V/L325W/K158X, A139V/L325W/M465X and A139V/L325W/F328X enzyme activities on pNCS (p-nitrocatechol sulfate) and 4-methylumbelliferyl sulfate (4MUS) substrates.
Figure 18:
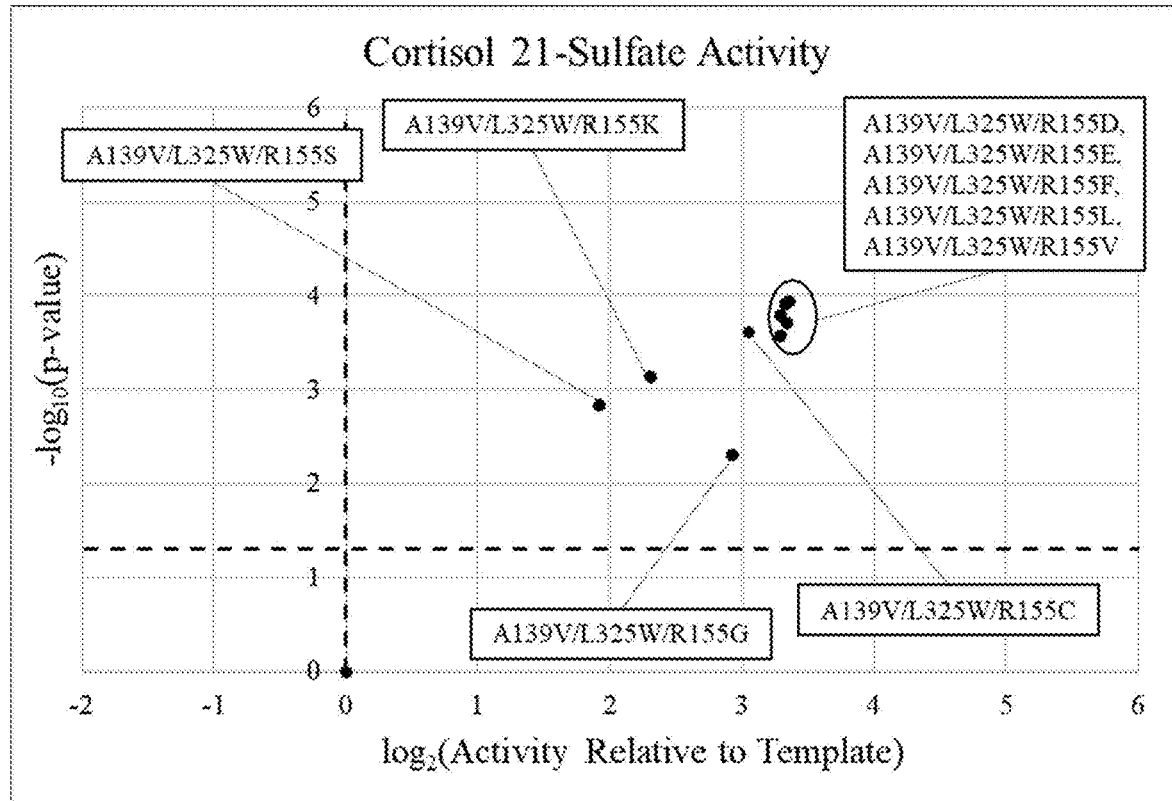
FIG. 18 is a graph showing the significant enzymatic activity of sulfatase variants A139V/L325W/R155X on cortisol 21-sulfate (CS).

In this example, three point mutations were made at various combinations of amino acid residues shown in FIG. 1, and the enzymatic activity of the triple point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 15. The results for the A139/R155/L325 variants on a panel of steroid sulfate substrates are shown in FIGS. 18 and 20. In FIGS. 18 and 20, variants indicated in the upper right quadrant of the graph exhibited increased activity as compared to template (or otherwise stated).

In summary, the results from FIGS. 18 and 20 demonstrate that the following PaS A139/R155/L325 triple point variants exhibited enhanced enzymatic activity against at least one, and often multiple, substrates as compared to the template from which the variant was derived: A139V/L325W/R155F, A139V/L325W/R155E, A139V/L325W/R155D, A139V/L325W/R155C, A139V/L325W/R155K, A139V/L325W/R155V, A139V/L325W/R155S, A139V/L325W/R155L and A139V/L325W/R155G, the amino acid sequence of which are shown in SEQ ID NOs: 76-84.

Example 24: Triple Point Mutation Variant A139/K158/L325

In this example, three point mutations were made at various combinations of amino acid residues shown in FIG. 1, and the enzymatic activity of the triple point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 15. The results for the A139/K158/L325 variants on a panel of steroid sulfate substrates are shown in FIG. 20. In FIG. 20, variants indicated in the upper right quadrant of the graph exhibited increased activity as compared to template (or otherwise stated).

In summary, the results from FIG. 20 demonstrate that the following PaS A139/K158/L325 triple point variants exhibited enhanced enzymatic activity against at least one, and often multiple, substrates as compared to the template from which the variant was derived: A139V/L325W/K158D, A139V/L325W/K158N, A139V/L325W/K158W and A139V/L325W/K158I, the amino acid sequence of which are shown in SEQ ID NOs: 85-88.

Example 25: Triple Point Mutation Variant A139/L325/F328

Figure 19:
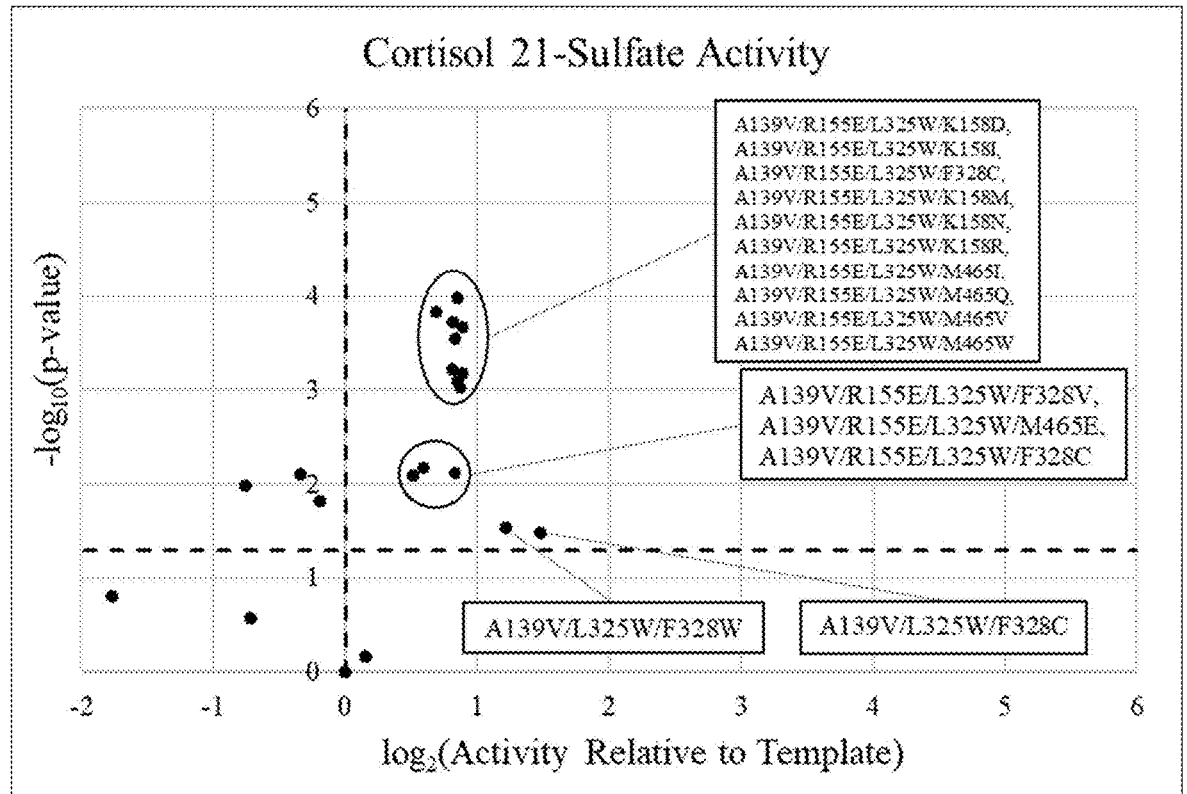
FIG. 19 is a graph showing the significant enzymatic activity of sulfatase variants A139V/R155E/L325W/

In this example, three point mutations were made at various combinations of amino acid residues shown in FIG. 1, and the enzymatic activity of the triple point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 15. The results for the A139/L325/F328 variants on a panel of steroid sulfate substrates are shown in FIGS. 19 and 21. In FIGS. 19 and 21, variants indicated in the upper right quadrant of the graph exhibited increased activity as compared to template (or otherwise stated).

In summary, the results from FIGS. 19 and 21 demonstrate that the following PaS A139/L325/F328 triple point variants exhibited enhanced enzymatic activity against at least one, and often multiple, substrates as compared to the template from which the variant was derived: A139V/L325W/F328W, A139V/L325W/F328V, A139V/L325W/F328G, A139V/L325W/F328C and A139V/L325W/F328A, the amino acid sequence of which are shown in SEQ ID NOs: 89-93.

Example 26: Triple Point Mutation Variant A139/L325/M465

In this example, three point mutations were made at various combinations of amino acid residues shown in FIG. 1, and the enzymatic activity of the triple point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 15. The results for the A139/L325/M465 variants on a panel of steroid sulfate substrates are shown in FIG. 21. In FIG. 21, variants indicated in the upper right quadrant of the graph exhibited increased activity as compared to template (or otherwise stated).

In summary, the results from FIG. 21 demonstrate that the following PaS A139/L325/M465 triple point variants exhibited enhanced enzymatic activity against at least one, and often multiple, substrates as compared to the template from which the variant was derived: A139V/L325W/M465A, A139V/L325W/M465Y, A139V/L325W/M465T, A139V/L325W/M465Q, A139V/L325W/M465N, A139V/L325W/M465L, A139V/L325W/M465I, A139V/L325W/M465W, A139V/L325W/M465C and A139V/L325W/M465F, the amino acid sequence of which are shown in SEQ ID NOs: 94-103.

Example 27: Quadruple Point Mutation Variant A139/R155/K158/L325

Figure 16:
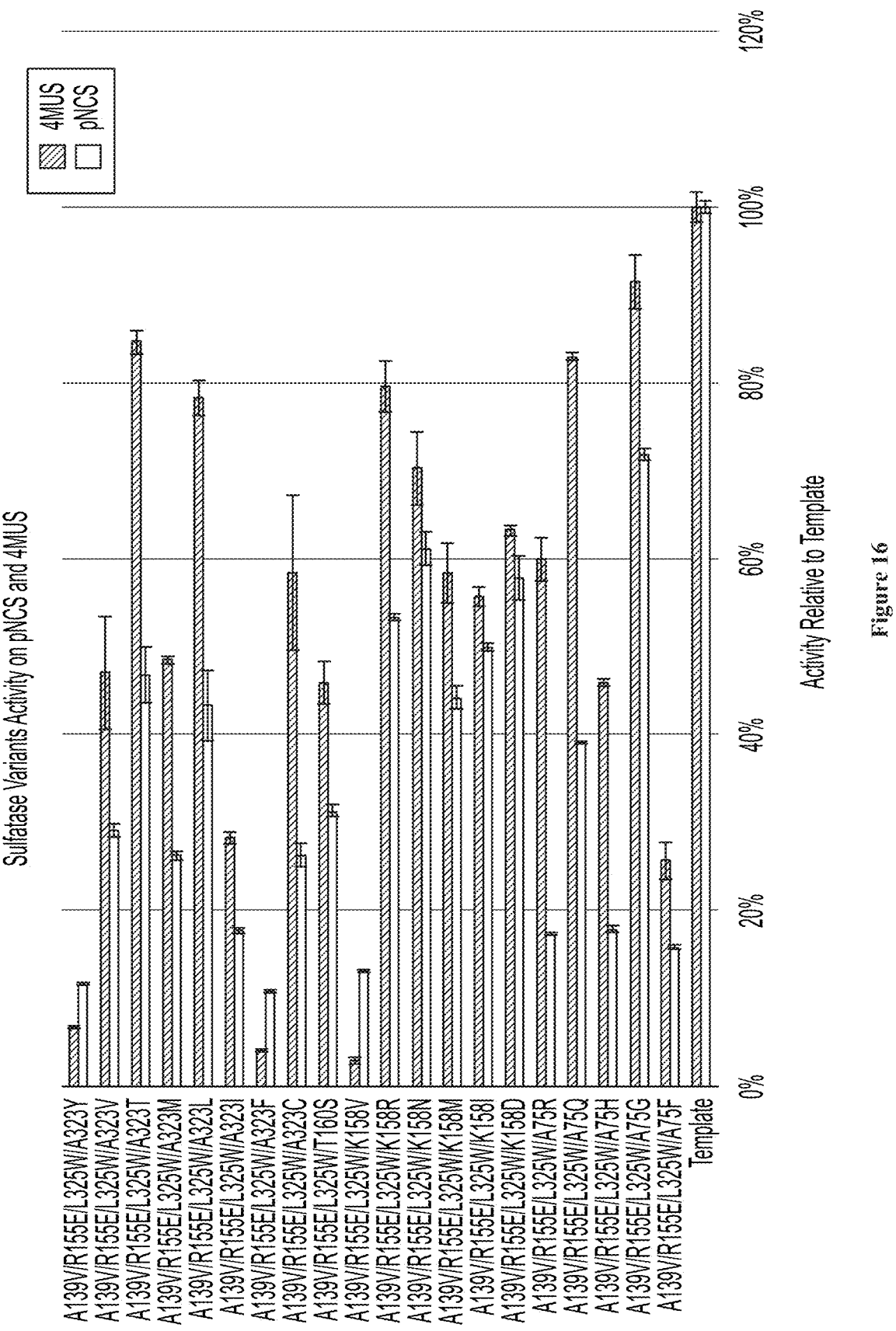
FIG. 16 is a bar graph depicting sulfatase variants A139V/R155E/L325W/A75X, A139V/R155E/L325W/K158X, A139V/R155E/L325X/T160S and A139V/R155E/L325X/A323X enzyme activities on pNCS (p-nitrocatechol sulfate) and 4-methylumbelliferyl sulfate (4MUS) substrates.

In this example, four point mutations were made at various combinations of amino acid residues shown in FIG. 1, and the enzymatic activity of the four point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 16. The results for the A139/R155/K158/L325 variants on a panel of steroid sulfate substrates are shown in FIGS. 19 and 22. In FIGS. 19 and 22, variants indicated in the upper right quadrant of the graph exhibited increased activity as compared to template (or otherwise stated).

In summary, the results from FIGS. 19 and 22 demonstrate that the following PaS A139/R155/K158/L325 quadruple point variants exhibited enhanced enzymatic activity against at least one, and often multiple, substrates as compared to the template from which the variant was derived: A139V/R155E/L325W/K158V, A139V/R155E/L325W/K158R, A139V/R155E/L325W/K158N, A139V/R155E/L325W/K158M, A139V/R155E/L325W/K158I and A139V/R155E/L325W/K158D, the amino acid sequence of which are shown in SEQ ID NOs: 104-109.

Example 28: Quadruple Point Mutation Variant A139/R155/A323/L325

In this example, four point mutations were made at various combinations of amino acid residues shown in FIG. 1, and the enzymatic activity of the four point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 16. The results for the A139/R155/A323/L325 variants on a panel of steroid sulfate substrates are shown in FIG. 25. In FIG. 25, variants indicated in the upper right quadrant of the graph exhibited increased activity as compared to template (or otherwise stated).

In summary, the results from FIG. 25 demonstrate that the following PaS A139/R155/A323/L325 quadruple point variants exhibited enhanced enzymatic activity against at least one, and often multiple, substrates as compared to the template from which the variant was derived: A139V/R155E/L325W/A323Y, A139V/R155E/L325W/A323V, A139V/R155E/L325W/A323T, A139V/R155E/L325W/A323M, A139V/R155E/L325W/A323L, A139V/R155E/L325W/A323I, A139V/R155E/L325W/A323F and A139V/R155E/L325W/A323C, the amino acid sequence of which are shown in SEQ ID NOs: 110-117.

Example 29: Quadruple Point Mutation Variant A139/R155/L325/F328

Figure 17:
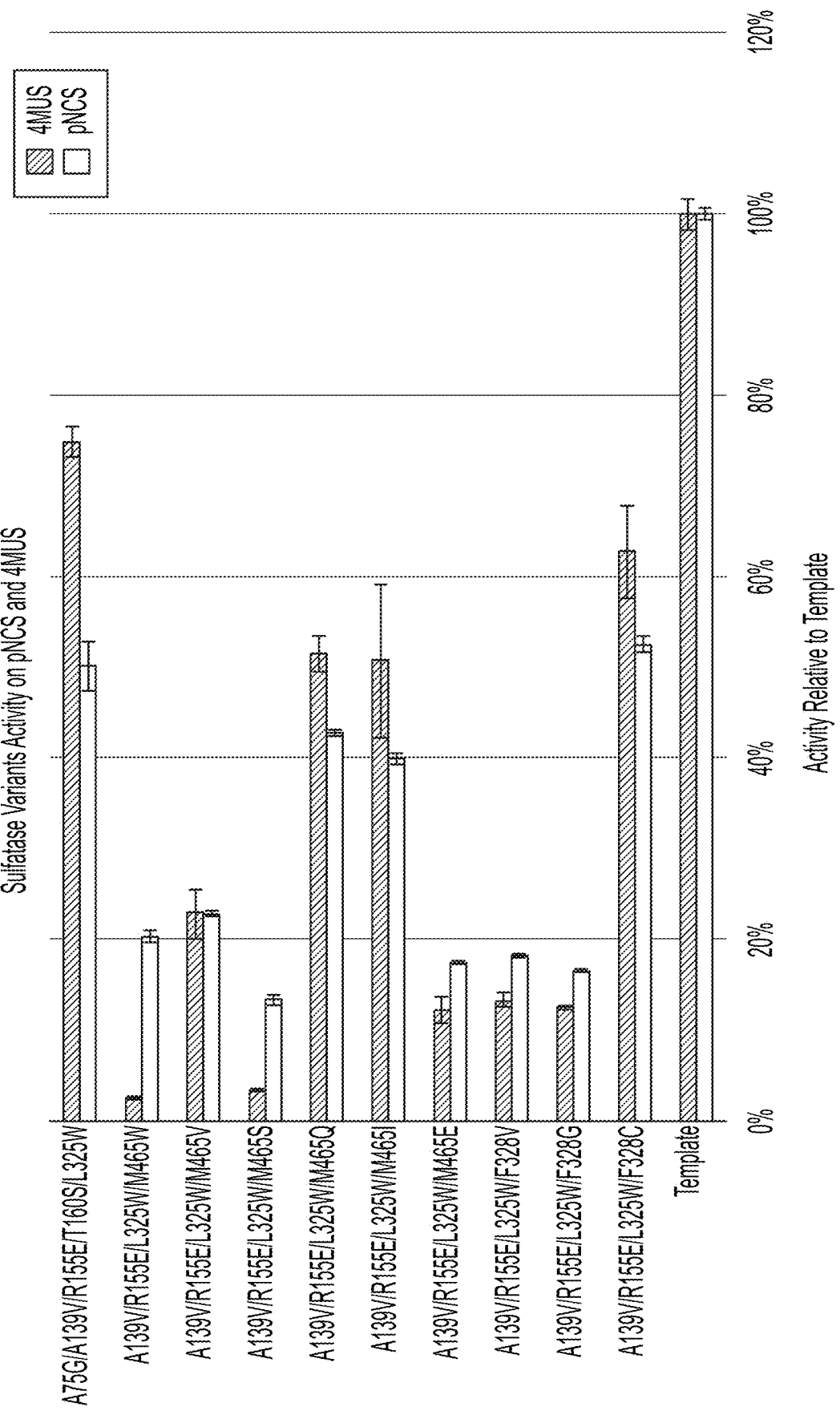
FIG. 17 is a bar graph depicting sulfatase variants A139V/R155E/L325W/F328X, A139V/R155E/L325W/M465X and A75G/A139V/R155E/T160S/L325W enzyme activities on pNCS (p-nitrocatechol sulfate) and 4-methylumbelliferyl sulfate (4MUS) substrates.

In this example, four point mutations were made at various combinations of amino acid residues shown in FIG. 1, and the enzymatic activity of the four point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 17. The results for the A139/R155/L325/F328 variants on a panel of steroid sulfate substrates are shown in FIGS. 19 and 22. In FIGS. 19 and 22, variants indicated in the upper right quadrant of the graph exhibited increased activity as compared to template (or otherwise stated).

In summary, the results from FIGS. 19 and 22 demonstrate that the following PaS A139/R155/L325/F328 quadruple point variants exhibited enhanced enzymatic activity against at least one, and often multiple, substrates as compared to the template from which the variant was derived: A139V/R155E/L325W/F328G, A139V/R155E/L325W/F328C and A139V/R155E/L325W/F328V, the amino acid sequence of which are shown in SEQ ID NOs: 118-120.

Example 30: Quadruple Point Mutation Variant A139/R155/L325/M465

In this example, four point mutations were made at various combinations of amino acid residues shown in FIG. 1, and the enzymatic activity of the four point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 17. The results for the A139/R155/L325/M465 variants on a panel of steroid sulfate substrates are shown in FIGS. 19 and 22. In FIGS. 19 and 22, variants indicated in the upper right quadrant of the graph exhibited increased activity as compared to template (or otherwise stated).

In summary, the results from FIGS. 19 and 22 demonstrate that the following PaS A139/R155/L325/M465 quadruple point variants exhibited enhanced enzymatic activity against at least one, and often multiple, substrates as compared to the template from which the variant was derived: A139V/R155E/L325W/M465W, A139V/R155E/L325W/M465V, A139V/R155E/L325W/M465S, A139V/R155E/L325W/M465Q, A139V/R155E/L325W/M465I and A139V/R155E/L325W/M465E, the amino acid sequence of which are shown in SEQ ID NOs: 121-126.

Example 31: Quadruple Point Mutation Variant A75/A139/R155/L325

In this example, four point mutations were made at various combinations of amino acid residues shown in FIG. 1, and the enzymatic activity of the four point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 16. The results for the A75/A139/R155/L325 variants on a panel of steroid sulfate substrates are shown in FIG. 23. In FIG. 23, variants indicated in the upper right quadrant of the graph exhibited increased activity as compared to template (or otherwise stated).

In summary, the results from FIG. 23 demonstrate that the following PaS A75/A139/R155/L325 quadruple point variants exhibited enhanced enzymatic activity against at least one, and often multiple, substrates as compared to the template from which the variant was derived: A139V/R155E/L325W/A75R, A139V/R155E/L325W/A75Q, A139V/R155E/L325W/A75H, A139V/R155E/L325W/A75G and A139V/R155E/L325W/A75F, the amino acid sequence of which are shown in SEQ ID NOs: 127-131.

Example 32: Quadruple Point Mutation Variant A139/R155/T160/L325

In this example, four point mutations were made at various combinations of amino acid residues shown in FIG.

1, and the enzymatic activity of the four point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 16. The results for the A139/R155/T160/L325 variants on a panel of steroid sulfate substrates are shown in FIG. 23. In FIG. 23, variants indicated in the upper right quadrant of the graph exhibited increased activity as compared to template (or otherwise stated).

In summary, the results from FIG. 23 demonstrate that the following PaS A139/R155/T160/L325 quadruple point variant exhibited enhanced enzymatic activity against at least one, and often multiple, substrates as compared to the template from which the variant was derived: A139V/R155E/T160S/L325W, the amino acid sequence of which is shown in SEQ ID NO: 132.

Example 33: Quintuple Point Mutation Variant A75/A139/R155/T160/L325

In this example, five point mutations were made at various combinations of amino acid residues shown in FIG. 1, and the enzymatic activity of the five point variants was tested on a panel of steroid sulfate substrates. Site-directed mutagenesis was performed as described in Example 5. The enzymatic activity of the variants was compared to the parental enzyme (i.e., unmutated enzyme, also referred to herein as the template) unless otherwise stated at pH 8.0. The results using these variants, as compared to template, with the pNCS and 4MUS substrates are shown in FIG. 17. The results for the A75/A139/R155/T160/L325 variants on a panel of steroid sulfate substrates are shown in FIG. 23. In FIG. 23, variants indicated in the upper right quadrant of the graph exhibited increased activity as compared to template (or otherwise stated). In summary, the results from FIG. 23 demonstrate that the following PaS A75/A139/R155/T160/L325 quintuple point variant exhibited enhanced enzymatic activity against at least one, and often multiple, substrates as compared to the template from which the variant was derived: A75G/A139V/R155E/T160S/L325W, the amino acid sequence of which is shown in SEQ ID NO: 133.

EQUIVALENTS

Those skilled in the art will recognize, or be able to ascertain using no more than routine experimentation, many equivalents of the specific embodiments of the invention described herein. Such equivalents are intended to be encompassed by the following claims.

SUMMARY OF SEQUENCE LISTING

| SEQ ID NO: | DESCRIPTION |
|---|---|
| 1 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaS: *Pseudomonas aeruginosa* sulfatase) |
| 2 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGCANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139C) |
| 3 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGIANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139I) |
| 4 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGLANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER |

| SEQ ID NO: | DESCRIPTION |
|---|---|
| | MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGMRAIRQGDWKAVYLPAPVGPATWQLYDLARDPGEIHDLADSQPGKLAELI EHWKRYVSETGVVEGASPFLVR (PaSA139L) |
| 5 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGSANHYGFEPPYDESTPRILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGMRAIRQGDWKAVYLPAPVGPATWQLYDLARDPGEIHDLADSQPGKLAELI EHWKRYVSETGVVEGASPFLVR (PaSA139S) |
| 6 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPRILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGMRAIRQGDWKAVYLPAPVGPATWQLYDLARDPGEIHDLADSQPGKLAELI EHWKRYVSETGVVEGASPFLVR (PaSA139V) |
| 7 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGAANHYGFEPPYDESTPDILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALLEAFPKFGPDLLGFLDRHYD NSLENIGRANSYVWYGPRWAQAATAPSRLYKAFTTQGGIRVPALVRYPRLSRQGAISH AFATVMDVTPTLLDLAGVRHPGKRWRGREIAEPRGRSWLGWLSGETEAAHDENTV TGWELFGMRAIRQGDWKAVYLPAPVGPATWQLYDLARDPGEIHDLADSQPGKLAEL IEHWKRYVSETGVVEGASPFLVR (PaSR155D) |
| 8 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGAANHYGFEPPYDESTPEILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGMRAIRQGDWKAVYLPAPVGPATWQLYDLARDPGEIHDLADSQPGKLAELI EHWKRYVSETGVVEGASPFLVR (PaSR155E) |
| 9 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGAANHYGFEPPYDESTPGILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALLEAFPKFGPDLLGFLDRHYD NSLENIGRANSYVWYGPRWAQAATAPSRLYKAFTTQGGIRVPALVRYPRLSRQGAISH AFATVMDVTPTLLDLAGVRHPGKRWRGREIAEPRGRSWLGWLSGETEAAHDENTV TGWELFGMRAIRQGDWKAVYLPAPVGPATWQLYDLARDPGEIHDLADSQPGKLAEL IEHWKRYVSETGVVEGASPFLVR (PaSR155G) |
| 10 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGAANHYGFEPPYDESTPPILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN |

| SEQ ID NO: | DESCRIPTION |
|---|---|
| | SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSR155P) |
| 11 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTQILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALLEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSR155Q) |
| 12 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPVILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSR155V) |
| 13 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALFEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSL325F) |
| 14 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSL325W) |
| 15 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALYEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSL325Y) |
| 16 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEACPKFGPDLLGFLDRHYDN<br>SLENIGRANSYVWYGPRWAQAATAPSRLYKAFTTQGGIRVPALVRYPRLSRQGAISHA |

| SEQ ID NO: | DESCRIPTION |
|---|---|
| | FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSF328C) |
| 17 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEASPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSF328S) |
| 18 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAWPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSF328W) |
| 19 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAWPTFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSK330T) |
| 20 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKEFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA376E) |
| 21 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKHFTTQGGIRVPALVRYPRLSRQGAISH<br>AFATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAEL<br>IEHWKRYVSETGVVEGASPFLVR<br>(PaSA376H) |
| 22 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKIFTTQGGIRVPALVRYPRLSRQGAISHA<br>FATVMDVTPTLLDLAGVRHPGKRWRGREIAEPRGRSWLGWLSGETEAAHDENTVT |

SUMMARY OF SEQUENCE LISTING

| SEQ ID NO: | DESCRIPTION |
|---|---|
| | GWELFGMRAIRQGDWKAVYLPAPVGPATWQLYDLARDPGEIHDLADSQPGKLAELI<br>EHWKRYVSETGVVEGASPFLVR<br>(PaSA3761) |
| 23 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKSFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA376S) |
| 24 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKTFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA376T) |
| 25 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKVFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA376V) |
| 26 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKVCTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSF377C) |
| 27 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKVTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSF377V) |
| 28 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN |

SUMMARY OF SEQUENCE LISTING

| SEQ ID NO: | DESCRIPTION |
|---|---|
| | SLENIGRANSYVWYGPRWAQAATAPSRLYKVWTTQGGIRVPALVRYPRLSRQGAISH AFATVMDVTPTLLDLAGVRHPGKRWRGREIAEPRGRSWLGWLSGETEAAHDENTV TGWELFGMRAIRQGDWKAVYLPAPVGPATWQLYDLARDPGEIHDLADSQPGKLAEL IEHWKRYVSETGVVEGASPFLVR (PaSF377W) |
| 29 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGAANHYGFEPPYDESTPRILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGQRAIRQGDWKAVYLPAPVGPATWQLYDLARDPGEIHDLADSQPGKLAELIE HWKRYVSETGVVEGASPFLVR (PaSM465Q) |
| 30 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGAANHYGFEPPYDESTPRILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGSRAIRQGDWKAVYLPAPVGPATWQLYDLARDPGEIHDLADSQPGKLAELIE HWKRYVSETGVVEGASPFLVR (PaSM465S) |
| 31 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGAANHYGFEPPYDESTPRILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGTRAIRQGDWKAVYLPAPVGPATWQLYDLARDPGEIHDLADSQPGKLAELIE HWKRYVSETGVVEGASPFLVR (PaSM465T) |
| 32 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPCILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGMRAIRQGDWKAVYLPAPVGPATWQLYDLARDPGEIHDLADSQPGKLAELI EHWKRYVSETGVVEGASPFLVR (PaSA139V/R155C) |
| 33 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPDILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALLEAFPKFGPDLLGFLDRHYD NSLENIGRANSYVWYGPRWAQAATAPSRLYKAFTTQGGIRVPALVRYPRLSRQGAISH AFATVMDVTPTLLDLAGVRHPGKRWRGREIAEPRGRSWLGWLSGETEAAHDENTV TGWELFGMRAIRQGDWKAVYLPAPVGPATWQLYDLARDPGEIHDLADSQPGKLAEL IEHWKRYVSETGVVEGASPFLVR (PaSA139V/R155D) |
| 34 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPEILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA |

SUMMARY OF SEQUENCE LISTING

| SEQ ID NO: | DESCRIPTION |
|---|---|
| | FATVMDVTPTLLDLAGVRHPGKRWRGREIAEPRGRSWLGWLSGETEAAHDENTVT GWELFGMRAIRQGDWKAVYLPAPVGPATWQLYDLARDPGEIHDLADSQPGKLAELI EHWKRYVSETGVVEGASPFLVR (PaSA139V/R155E) |
| 35 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPGILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALLEAFPKFGPDLLGFLDRHYD NSLENIGRANSYVWYGPRWAQAATAPSRLYKAFTTQGGIRVPALVRYPRLSRQGAISH AFATVMDVTPTLLDLAGVRHPGKRWRGREIAEPRGRSWLGWLSGETEAAHDENTV TGWELFGMRAIRQGDWKAVYLPAPVGPATWQLYDLARDPGEIHDLADSQPGKLAEL IEHWKRYVSETGVVEGASPFLVR (PaSA139V/R155G) |
| 36 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPKILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALLEAFPKFGPDLLGFLDRHYD NSLENIGRANSYVWYGPRWAQAATAPSRLYKAFTTQGGIRVPALVRYPRLSRQGAISH AFATVMDVTPTLLDLAGVRHPGKRWRGREIAEPRGRSWLGWLSGETEAAHDENTV TGWELFGMRAIRQGDWKAVYLPAPVGPATWQLYDLARDPGEIHDLADSQPGKLAEL IEHWKRYVSETGVVEGASPFLVR (PaSA139V/R155K) |
| 37 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPLILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGMRAIRQGDWKAVYLPAPVGPATWQLYDLARDPGEIHDLADSQPGKLAELI EHWKRYVSETGVVEGASPFLVR (PaSA139V/R155L) |
| 38 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPSILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGMRAIRQGDWKAVYLPAPVGPATWQLYDLARDPGEIHDLADSQPGKLAELI EHWKRYVSETGVVEGASPFLVR (PaSA139V/R155S) |
| 39 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPVILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALLEAFPKFGPDLLGFLDRHYD NSLENIGRANSYVWYGPRWAQAATAPSRLYKAFTTQGGIRVPALVRYPRLSRQGAISH AFATVMDVTPTLLDLAGVRHPGKRWRGREIAEPRGRSWLGWLSGETEAAHDENTV TGWELFGMRAIRQGDWKAVYLPAPVGPATWQLYDLARDPGEIHDLADSQPGKLAEL IEHWKRYVSETGVVEGASPFLVR (PaSA139V/R155V) |
| 40 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPWILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALLEAFPKFGPDLLGFLDRHYD NSLENIGRANSYVWYGPRWAQAATAPSRLYKAFTTQGGIRVPALVRYPRLSRQGAISH AFATVMDVTPTLLDLAGVRHPGKRWRGREIAEPRGRSWLGWLSGETEAAHDENTV |

SUMMARY OF SEQUENCE LISTING

| SEQ ID NO: | DESCRIPTION |
|---|---|
| | TGWELFGMRAIRQGDWKAVYLPAPVGPATWQLYDLARDPGEIHDLADSQPGKLAEL<br>IEHWKRYVSETGVVEGASPFLVR<br>(PaSA139V/R155W) |
| 41 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPEILKGTPALYVEDERYLDTLP<br>EGFYSSDAFGDKLLQYLKERDQSRPFFAYLPFSAPHWPLQAPREMVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALLEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSR155E/I220M) |
| 42 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRALKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALLEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/I156A) |
| 43 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRDLKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALLEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/I156D) |
| 44 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRELKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALLEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/I156E) |
| 45 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRGLKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALLEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/I156G) |
| 46 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRTLKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALLEAFPKFGPDLLGFLDRHYD |

| SEQ ID NO: | DESCRIPTION |
|---|---|
| | NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/I156T) |
| 47 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRWLKGTPALYVEDERYLDT<br>LPEGFYSSDAFGDKLLQYLKERDQSRPFFAYLPFSAPHWPLQAPREIVEKYRGRYDAG<br>PEALRQERLARLKELGLVEADVEAHPVLALTREWEALEDEERAKSARAMEVYAAMV<br>ERMDWNIGRVVDYLRRQGELDNTFVLFMSDNGAEGALLEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/I156W) |
| 48 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPEILKGTPALYVEDERYLDTLP<br>EGFYSSDAFGDKLLQYLKERDQSRPFFAYLPFSAPHWPLQAPREMVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALLEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/I220M) |
| 49 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALCEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/L325C) |
| 50 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALHEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/L325H) |
| 51 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALGEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/L325G) |
| 52 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALKEAFPKFGPDLLGFLDRHYDN<br>SLENIGRANSYVWYGPRWAQAATAPSRLYKAFTTQGGIRVPALVRYPRLSRQGAISHA |

| SEQ ID NO: | DESCRIPTION |
|---|---|
| | FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/L325K) |
| 53 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALPEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/L325P) |
| 54 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALTEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/L325T) |
| 55 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALVEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/L325V) |
| 56 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALYEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/L325Y) |
| 57 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/L325W) |
| 58 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALEEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT |

| SEQ ID NO: | DESCRIPTION |
|---|---|
| | GWELFGMRAIRQGDWKAVYLPAPVGPATWQLYDLARDPGEIHDLADSQPGKLAELI<br>EHWKRYVSETGVVEGASPFLVR<br>(PaSA139V/L325F) |
| 59 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGAANHYGFEPPYDESTPRILKGTPALYVEDERYLDTLP<br>EGFYSSDAFGDKLLQYLKERDQSRPFFAYLPFSAPHWPLQAPREMVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALYEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSL325Y/I220M) |
| 60 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAAPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/F328A) |
| 61 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEACPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/F328C) |
| 62 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEALPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/F328L) |
| 63 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAWPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/F328W) |
| 64 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPDFGPDLLGFLDRHYDN |

| SEQ ID NO: | DESCRIPTION |
|---|---|
| | SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/K330D) |
| 65 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPSFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/K330S) |
| 66 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPTFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/K330T) |
| 67 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPVFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/K330V) |
| 68 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPYFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/K330Y) |
| 69 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKAFTTQGGIRVPALVRYPRLSRQGAISHA<br>FATVMDVTPTLLDLAGVRHPGKRWRGREIAEPRGRSWLGWLSGETEAAHDENTVT<br>GWELFGFRAIRQGDWKAVYLPAPVGPATWQLYDLARDPGEIHDLADSQPGKLAELIE<br>HWKRYVSETGVVEGASPFLVR<br>(PaSA139V/M465F) |
| 70 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGFEPPYDESTPRILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALLEAFPKFGPDLLGFLDRHYDN<br>SLENIGRANSYVWYGPRWAQAATAPSRLYKAFTTQGGIRVPALVRYPRLSRQGAISHA |

| SEQ ID NO: | DESCRIPTION |
|---|---|
| | FATVMDVTPTLLDLAGVRHPGKRWRGREIAEPRGRSWLGWLSGETEAAHDENTVT GWELFGIRAIRQGDWKAVYLPAPVGPATWQLYDLARDPGEIHDLADSQPGKLAELIE HWKRYVSETGVVEGASPFLVR (PaSA139V/M465I) |
| 71 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPRILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGQRAIRQGDWKAVYLPAPVGPATWQLYDLARDPGEIHDLADSQPGKLAELIE HWKRYVSETGVVEGASPFLVR (PaSA139V/M465Q) |
| 72 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPRILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGSRAIRQGDWKAVYLPAPVGPATWQLYDLARDPGEIHDLADSQPGKLAELIE HWKRYVSETGVVEGASPFLVR (PaSA139V/M465S) |
| 73 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPRILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGPRAIRQGDWKAVYLPAPVGPATWQLYDLARDPGEIHDLADSQPGKLAELIE HWKRYVSETGVVEGASPFLVR (PaSA139V/M465E) |
| 74 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPRILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGPRAIRQGDWKAVYLPAPVGPATWQLYDLARDPGEIHDLADSQPGKLAELIE HWKRYVSETGVVEGASPFLVR (PaSA139V/M465P) |
| 75 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPRILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALLEAFPKFGPDLLGFLDRHYDN SLENIGRANSYVWYGPRWAQAATAPSRLYKAFTTQGGIRVPALVRYPRLSRQGAISHA FATVMDVTPTLLDLAGVRHPGKRWRGREIAEPRGRSWLGWLSGETEAAHDENTVT GWELFGVRAIRQGDWKAVYLPAPVGPATWQLYDLARDPGEIHDLADSQPGKLAELIE HWKRYVSETGVVEGASPFLVR (PaSA139V/M465V) |
| 76 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGFEPPYDESTPFILKGTPALYVEDERYLDTLP EGFYSSDAFGDKLLQYLKERDQSRPFFAYLPFSAPHWPLQAPREIVEKYRGRYDAGPE ALRQERLARLKELGLVEADVEAHPVLALTREWEALEDEERAKSARAMEVYAAMVER MDWNIGRVVDYLRRQGELDNTFVLFMSDNGAEGALWEAFPKFGPDLLGFLDRHYD NSLENIGRANSYVWYGPRWAQAATAPSRLYKAFTTQGGIRVPALVRYPRLSRQGAISH AFATVMDVTPTLLDLAGVRHPGKRWRGREIAEPRGRSWLGWLSGETEAAHDENTV |

SUMMARY OF SEQUENCE LISTING

| SEQ ID NO: | DESCRIPTION |
|---|---|
| | TGWELFGMRAIRQGDWKAVYLPAPVGPATWQLYDLARDPGEIHDLADSQPGKLAEL<br>IEHWKRYVSETGVVEGASPFLVR<br>(PaSA139V/L325W/R155F) |
| 77 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/L325W/R155E) |
| 78 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPDILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/L325W/R155D) |
| 79 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPCILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/L325W/R155C) |
| 80 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPKILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/L325W/R155K) |
| 81 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPVILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/L325W/R155V) |
| 82 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPSILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL |

| SEQ ID NO: | DESCRIPTION |
|---|---|
| | IEHWKRYVSETGVVEGASPFLVR<br>(PaSA139V/L325W/R155S) |
| 83 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPLILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/L325W/R155L) |
| 84 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPGILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/L325W/R155G) |
| 85 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILDGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/L325W/K158D) |
| 86 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILNGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/L325W/K158N) |
| 87 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILWGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/L325W/K158W) |
| 88 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILIGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD |

SUMMARY OF SEQUENCE LISTING

| SEQ ID NO: | DESCRIPTION |
|---|---|
| | NSLENIGRANSYVWYGPRWAQAATAPSRLYKAFTTQGGIRVPALVRYPRLSRQGAISH AFATVMDVTPTLLDLAGVRHPGKRWRGREIAEPRGRSWLGWLSGETEAAHDENTV TGWELFGMRAIRQGDWKAVYLPAPVGPATWQLYDLARDPGEIHDLADSQPGKLAEL IEHWKRYVSETGVVEGASPFLVR (PaSA139V/L325W/K158F) |
| 89 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGEEPPYDESTPRILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALWEAWPKFGPDLLGFLDRHY DNSLENIGRANSYVWYGPRWAQAATAPSRLYKAFTTQGGIRVPALVRYPRLSRQGAIS HAFATVMDVTPTLLDLAGVRHPGKRWRGREIAEPRGRSWLGWLSGETEAAHDENT VTGWELFGMRAIRQGDWKAVYLPAPVGPATWQLYDLARDPGEIHDLADSQPGKLAE LIEHWKRYVSETGVVEGASPFLVR (PaSA139V/L325W/F328W) |
| 90 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGEEPPYDESTPRILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALWEAVPKFGPDLLGFLDRHY DNSLENIGRANSYVWYGPRWAQAATAPSRLYKAFTTQGGIRVPALVRYPRLSRQGAIS HAFATVMDVTPTLLDLAGVRHPGKRWRGREIAEPRGRSWLGWLSGETEAAHDENT VTGWELFGMRAIRQGDWKAVYLPAPVGPATWQLYDLARDPGEIHDLADSQPGKLAE LIEHWKRYVSETGVVEGASPFLVR (PaSA139V/L325W/F328V) |
| 91 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGEEPPYDESTPRILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALWEAGPKFGPDLLGFLDRHY DNSLENIGRANSYVWYGPRWAQAATAPSRLYKAFTTQGGIRVPALVRYPRLSRQGAIS HAFATVMDVTPTLLDLAGVRHPGKRWRGREIAEPRGRSWLGWLSGETEAAHDENT VTGWELFGMRAIRQGDWKAVYLPAPVGPATWQLYDLARDPGEIHDLADSQPGKLAE LIEHWKRYVSETGVVEGASPFLVR (PaSA139V/L325W/F328G) |
| 92 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGEEPPYDESTPRILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALWEACPKFGPDLLGFLDRHY DNSLENIGRANSYVWYGPRWAQAATAPSRLYKAFTTQGGIRVPALVRYPRLSRQGAIS HAFATVMDVTPTLLDLAGVRHPGKRWRGREIAEPRGRSWLGWLSGETEAAHDENT VTGWELFGMRAIRQGDWKAVYLPAPVGPATWQLYDLARDPGEIHDLADSQPGKLAE LIEHWKRYVSETGVVEGASPFLVR (PaSA139V/L325W/F328C) |
| 93 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGEEPPYDESTPRILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALWEAAPKFGPDLLGFLDRHY DNSLENIGRANSYVWYGPRWAQAATAPSRLYKAFTTQGGIRVPALVRYPRLSRQGAIS HAFATVMDVTPTLLDLAGVRHPGKRWRGREIAEPRGRSWLGWLSGETEAAHDENT VTGWELFGMRAIRQGDWKAVYLPAPVGPATWQLYDLARDPGEIHDLADSQPGKLAE LIEHWKRYVSETGVVEGASPFLVR (PaSA139V/L325W/F328A) |
| 94 | MSKRPNFLVIVADDLGFSDIGAFGGEIATPNLDALAIAGLRLTDFHTASTCSPTRSMLL TGTDHHIAGIGTMAEALTPELEGKPGYEGHLNERVVALPELLREAGYQTLMAGKWHL GLKPEQTPHARGFERSFSLLPGVANHYGEEPPYDESTPRILKGTPALYVEDERYLDTL PEGFYSSDAFGDKLLQYLKERDQSRPFFAYLPFSAPHWPLQAPREIVEKYRGRYDAGP EALRQERLARLKELGLVEADVEAHPVLALTREWEALEDEERAKSARAMEVYAAMVE RMDWNIGRVVDYLRRQGELDNTFVLFMSDNGAEGALWEAFPKFGPDLLGFLDRHY DNSLENIGRANSYVWYGPRWAQAATAPSRLYKAFTTQGGIRVPALVRYPRLSRQGAIS |

SUMMARY OF SEQUENCE LISTING

| SEQ ID NO: | DESCRIPTION |
|---|---|
| | HAFATVMDVTPTLLDLAGVRHPGKRWRGREIAEPRGRSWLGWLSGETEAAHDENT<br>VTGWELFGARAIRQGDWKAVYLPAPVGPATWQLYDLARDPGEIHDLADSQPGKLAE<br>LIEHWKRYVSETGVVEGASPFLVR<br>(PaSA139V/L325W/M465A) |
| 95 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGYRAIRQGDWKAVYLPAPVGPATWQLYDLARDPGEIHDLADSQPGKLAE<br>LIEHWKRYVSETGVVEGASPFLVR<br>(PaSA139V/L325W/M465Y) |
| 96 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGTRAIRQGDWKAVYLPAPVGPATWQLYDLARDPGEIHDLADSQPGKLAE<br>LIEHWKRYVSETGVVEGASPFLVR<br>(PaSA139V/L325W/M465T) |
| 97 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGQRAIRQGDWKAVYLPAPVGPATWQLYDLARDPGEIHDLADSQPGKLAE<br>LIEHWKRYVSETGVVEGASPFLVR<br>(PaSA139V/L325W/M465Q) |
| 98 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGNRAIRQGDWKAVYLPAPVGPATWQLYDLARDPGEIHDLADSQPGKLAE<br>LIEHWKRYVSETGVVEGASPFLVR<br>(PaSA139V/L325W/M465N) |
| 99 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGLRAIRQGDWKAVYLPAPVGPATWQLYDLARDPGEIHDLADSQPGKLAE<br>LIEHWKRYVSETGVVEGASPFLVR<br>(PaSA139V/L325W/M465L) |
| 100 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT |

SUMMARY OF SEQUENCE LISTING

| SEQ ID NO: | DESCRIPTION |
|---|---|
| | VTGWELFGIRAIRQGDWKAVYLPAPVGPATWQLYDLARDPGEIHDLADSQPGKLAEL<br>IEHWKRYVSETGVVEGASPFLVR<br>(PaSA139V/L325W/M465I) |
| 101 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGWRAIRQGDWKAVYLPAPVGPATWQLYDLARDPGEIHDLADSQPGKLA<br>ELIEHWKRYVSETGVVEGASPFLVR<br>(PaSA139V/L325W/M465W) |
| 102 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGCRAIRQGDWKAVYLPAPVGPATWQLYDLARDPGEIHDLADSQPGKLAE<br>LIEHWKRYVSETGVVEGASPFLVR<br>(PaSA139V/L325W/M465C) |
| 103 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPRILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGFRAIRQGDWKAVYLPAPVGPATWQLYDLARDPGEIHDLADSQPGKLAE<br>LIEHWKRYVSETGVVEGASPFLVR<br>(PaSA139V/L325W/M465F) |
| 104 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILVGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/L325W/K158V) |
| 105 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILRGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/R155E/L325W/K158R) |
| 106 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILNGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE |

SUMMARY OF SEQUENCE LISTING

| SEQ ID NO: | DESCRIPTION |
|---|---|
| | RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/R155E/L325W/K158N) |
| 107 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILMGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/R155E/L325W/K158M) |
| 108 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILIGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/L325W/K158I) |
| 109 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILDGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/R155E/L325W/K158D) |
| 110 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGYLWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/L325W/A323Y) |
| 111 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGVLWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/L325W/A323V) |
| 112 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGTLWEAFPKFGPDLLGFLDRHYD |

| SUMMARY OF SEQUENCE LISTING |
|---|

| SEQ ID NO: | DESCRIPTION |
|---|---|
| | NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/L325W/A323T) |
| 113 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGMLWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/L325W/A323M) |
| 114 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGLLWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/L325W/A323L) |
| 115 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGILWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTVT<br>GWELFGMRAIRQGDWKAVYLPAPVGPATWQLYDLARDPGEIHDLADSQPGKLAELI<br>EHWKRYVSETGVVEGASPFLVR<br>(PaSA139V/R155E/L325W/A323I) |
| 116 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGELWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/L325W/A323F) |
| 117 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGCLWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/L325W/A323C) |
| 118 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAGPKFGPDLLGFLDRHYD<br>NSLENIGRANSYVWYGPRWAQAATAPSRLYKAFTTQGGIRVPALVRYPRLSRQGAISH |

| SUMMARY OF SEQUENCE LISTING | |
|---|---|
| SEQ ID NO: | DESCRIPTION |

AFATVMDVTPTLLDLAGVRHPGKRWRGREIAEPRGRSWLGWLSGETEAAHDENTV
      TGWELFGMRAIRQGDWKAVYLPAPVGPATWQLYDLARDPGEIHDLADSQPGKLAEL
      IEHWKRYVSETGVVEGASPFLVR
      (PaSA139V/R155E/L325W/F328G)

119    MSKRPNFLVIVADDLGFSDIGAFGGEIATPNLDALAIAGLRLTDFHTASTCSPTRSMLL
      TGTDHHIAGIGTMAEALTPELEGKPGYEGHLNERVVALPELLREAGYQTLMAGKWHL
      GLKPEQTPHARGFERSFSLLPGVANHYGEEPPYDESTPEILKGTPALYVEDERYLDTLP
      EGFYSSDAFGDKLLQYLKERDQSRPFFAYLPFSAPHWPLQAPREIVEKYRGRYDAGPE
      ALRQERLARLKELGLVEADVEAHPVLALTREWEALEDEERAKSARAMEVYAAMVER
      MDWNIGRVVDYLRRQGELDNTFVLFMSDNGAEGALWEACPKFGPDLLGFLDRHYD
      NSLENIGRANSYVWYGPRWAQAATAPSRLYKAFTTQGGIRVPALVRYPRLSRQGAISH
      AFATVMDVTPTLLDLAGVRHPGKRWRGREIAEPRGRSWLGWLSGETEAAHDENTV
      TGWELFGMRAIRQGDWKAVYLPAPVGPATWQLYDLARDPGEIHDLADSQPGKLAEL
      IEHWKRYVSETGVVEGASPFLVR
      (PaSA139V/R155E/L325W/F328C)

120    MSKRPNFLVIVADDLGFSDIGAFGGEIATPNLDALAIAGLRLTDFHTASTCSPTRSMLL
      TGTDHHIAGIGTMAEALTPELEGKPGYEGHLNERVVALPELLREAGYQTLMAGKWHL
      GLKPEQTPHARGFERSFSLLPGVANHYGEEPPYDESTPEILKGTPALYVEDERYLDTLP
      EGFYSSDAFGDKLLQYLKERDQSRPFFAYLPFSAPHWPLQAPREIVEKYRGRYDAGPE
      ALRQERLARLKELGLVEADVEAHPVLALTREWEALEDEERAKSARAMEVYAAMVER
      MDWNIGRVVDYLRRQGELDNTFVLFMSDNGAEGALWEAVPKFGPDLLGFLDRHYD
      NSLENIGRANSYVWYGPRWAQAATAPSRLYKAFTTQGGIRVPALVRYPRLSRQGAISH
      AFATVMDVTPTLLDLAGVRHPGKRWRGREIAEPRGRSWLGWLSGETEAAHDENTV
      TGWELFGMRAIRQGDWKAVYLPAPVGPATWQLYDLARDPGEIHDLADSQPGKLAEL
      IEHWKRYVSETGVVEGASPFLVR
      (PaSA139V/R155E/L325W/F328V)

121    MSKRPNFLVIVADDLGFSDIGAFGGEIATPNLDALAIAGLRLTDFHTASTCSPTRSMLL
      TGTDHHIAGIGTMAEALTPELEGKPGYEGHLNERVVALPELLREAGYQTLMAGKWHL
      GLKPEQTPHARGFERSFSLLPGVANHYGEEPPYDESTPEILKGTPALYVEDERYLDTLP
      EGFYSSDAFGDKLLQYLKERDQSRPFFAYLPFSAPHWPLQAPREIVEKYRGRYDAGPE
      ALRQERLARLKELGLVEADVEAHPVLALTREWEALEDEERAKSARAMEVYAAMVER
      MDWNIGRVVDYLRRQGELDNTFVLFMSDNGAEGALWEAFPKFGPDLLGFLDRHYD
      NSLENIGRANSYVWYGPRWAQAATAPSRLYKAFTTQGGIRVPALVRYPRLSRQGAISH
      AFATVMDVTPTLLDLAGVRHPGKRWRGREIAEPRGRSWLGWLSGETEAAHDENTV
      TGWELFGWRAIRQGDWKAVYLPAPVGPATWQLYDLARDPGEIHDLADSQPGKLAEL
      IEHWKRYVSETGVVEGASPFLVR
      (PaSA139V/R155E/L325W/M465W)

122    MSKRPNFLVIVADDLGFSDIGAFGGEIATPNLDALAIAGLRLTDFHTASTCSPTRSMLL
      TGTDHHIAGIGTMAEALTPELEGKPGYEGHLNERVVALPELLREAGYQTLMAGKWHL
      GLKPEQTPHARGFERSFSLLPGVANHYGEEPPYDESTPEILKGTPALYVEDERYLDTLP
      EGFYSSDAFGDKLLQYLKERDQSRPFFAYLPFSAPHWPLQAPREIVEKYRGRYDAGPE
      ALRQERLARLKELGLVEADVEAHPVLALTREWEALEDEERAKSARAMEVYAAMVER
      MDWNIGRVVDYLRRQGELDNTFVLFMSDNGAEGALWEAFPKFGPDLLGFLDRHYD
      NSLENIGRANSYVWYGPRWAQAATAPSRLYKAFTTQGGIRVPALVRYPRLSRQGAISH
      AFATVMDVTPTLLDLAGVRHPGKRWRGREIAEPRGRSWLGWLSGETEAAHDENTV
      TGWELFGVRAIRQGDWKAVYLPAPVGPATWQLYDLARDPGEIHDLADSQPGKLAELI
      EHWKRYVSETGVVEGASPFLVR
      (PaSA139V/R155E/L325W/M465V)

123    MSKRPNFLVIVADDLGFSDIGAFGGEIATPNLDALAIAGLRLTDFHTASTCSPTRSMLL
      TGTDHHIAGIGTMAEALTPELEGKPGYEGHLNERVVALPELLREAGYQTLMAGKWHL
      GLKPEQTPHARGFERSFSLLPGVANHYGEEPPYDESTPEILKGTPALYVEDERYLDTLP
      EGFYSSDAFGDKLLQYLKERDQSRPFFAYLPFSAPHWPLQAPREIVEKYRGRYDAGPE
      ALRQERLARLKELGLVEADVEAHPVLALTREWEALEDEERAKSARAMEVYAAMVER
      MDWNIGRVVDYLRRQGELDNTFVLFMSDNGAEGALWEAFPKFGPDLLGFLDRHYD
      NSLENIGRANSYVWYGPRWAQAATAPSRLYKAFTTQGGIRVPALVRYPRLSRQGAISH
      AFATVMDVTPTLLDLAGVRHPGKRWRGREIAEPRGRSWLGWLSGETEAAHDENTV
      TGWELFGSRAIRQGDWKAVYLPAPVGPATWQLYDLARDPGEIHDLADSQPGKLAELI
      EHWKRYVSETGVVEGASPFLVR
      (PaSA139V/R155E/L325W/M465S)

124    MSKRPNFLVIVADDLGFSDIGAFGGEIATPNLDALAIAGLRLTDFHTASTCSPTRSMLL
      TGTDHHIAGIGTMAEALTPELEGKPGYEGHLNERVVALPELLREAGYQTLMAGKWHL
      GLKPEQTPHARGFERSFSLLPGVANHYGEEPPYDESTPEILKGTPALYVEDERYLDTLP
      EGFYSSDAFGDKLLQYLKERDQSRPFFAYLPFSAPHWPLQAPREIVEKYRGRYDAGPE
      ALRQERLARLKELGLVEADVEAHPVLALTREWEALEDEERAKSARAMEVYAAMVER
      MDWNIGRVVDYLRRQGELDNTFVLFMSDNGAEGALWEAFPKFGPDLLGFLDRHYD
      NSLENIGRANSYVWYGPRWAQAATAPSRLYKAFTTQGGIRVPALVRYPRLSRQGAISH
      AFATVMDVTPTLLDLAGVRHPGKRWRGREIAEPRGRSWLGWLSGETEAAHDENTV

SUMMARY OF SEQUENCE LISTING

| SEQ ID NO: | DESCRIPTION |
|---|---|
| | TGWELFGQRAIRQGDWKAVYLPAPVGPATWQLYDLARDPGEIHDLADSQPGKLAELI<br>EHWKRYVSETGVVEGASPFLVR<br>(PaSA139V/R155E/L325W/M465Q) |
| 125 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGIRAIRQGDWKAVYLPAPVGPATWQLYDLARDPGEIHDLADSQPGKLAELI<br>EHWKRYVSETGVVEGASPFLVR<br>(PaSA139V/R155E/L325W/M465F) |
| 126 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTPEILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGERAIRQGDWKAVYLPAPVGPATWQLYDLARDPGEIHDLADSQPGKLAELI<br>EHWKRYVSETGVVEGASPFLVR<br>(PaSA139V/R155E/L325W/M465E) |
| 127 | MSKRPNFLVIVADDLGFSDIGAFGGEIATPNLDALAIAGLRLTDFHTASTCSPTRSMLL<br>TGTDHHIAGIGTMAERLTPELEGKPGYEGHLNERVVALPELLREAGYQTLMAGKWH<br>LGLKPEQTPHARGFERSFSLLPGVANHYGEEPPYDESTPEILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/R155E/L325W/A75R) |
| 128 | MSKRPNFLVIVADDLGFSDIGAFGGEIATPNLDALAIAGLRLTDFHTASTCSPTRSMLL<br>TGTDHHIAGIGTMAEQLTPELEGKPGYEGHLNERVVALPELLREAGYQTLMAGKWH<br>LGLKPEQTPHARGFERSFSLLPGVANHYGEEPPYDESTPEILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/R155E/L325W/A75Q) |
| 129 | MSKRPNFLVIVADDLGFSDIGAFGGEIATPNLDALAIAGLRLTDFHTASTCSPTRSMLL<br>TGTDHHIAGIGTMAEHLTPELEGKPGYEGHLNERVVALPELLREAGYQTLMAGKWH<br>LGLKPEQTPHARGFERSFSLLPGVANHYGEEPPYDESTPEILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/R155E/L325W/A75H) |
| 130 | MSKRPNFLVIVADDLGFSDIGAFGGEIATPNLDALAIAGLRLTDFHTASTCSPTRSMLL<br>TGTDHHIAGIGTMAEGLTPELEGKPGYEGHLNERVVALPELLREAGYQTLMAGKWH<br>LGLKPEQTPHARGFERSFSLLPGVANHYGEEPPYDESTPEILKGTPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE |

SUMMARY OF SEQUENCE LISTING

| SEQ ID NO: | DESCRIPTION |
|---|---|
| | LIEHWKRYVSETGVVEGASPFLVR<br>(PaSA139V/R155E/L325W/A75G) |
| 131 | MSKRPNFLVIVADDLGFSDIGAFGGEIATPNLDALAIAGLRLTDFHTASTCSPTRSMLL<br>TGTDHHIAGIGTMAEFLTPELEGKPGYEGHLNERVVALPELLREAGYQTLMAGKWHL<br>GLKPEQTPHARGFERSFSLLPGVANHYGEEPPYDESTP<u>E</u>ILKGTPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/L325W/A75F) |
| 132 | MSKRPNFLVIVADDLGFSDIGAFGGEIATPNLDALAIAGLRLTDFHTASTCSPTRSMLL<br>TGTDHHIAGIGTMAEALTPELEGKPGYEGHLNERVVALPELLREAGYQTLMAGKWHL<br>GLKPEQTPHARGFERSFSLLPGVANHYGEEPPYDESTP<u>E</u>ILKGSPALYVEDERYLDTLP<br>EGFYSSDAFGDKLLQYLKERDQSRPFFAYLPFSAPHWPLQAPREIVEKYRGRYDAGPE<br>ALRQERLARLKELGLVEADVEAHPVLALTREWEALEDEERAKSARAMEVYAAMVER<br>MDWNIGRVVDYLRRQGELDNTFVLFMSDNGAEGALWEAFPKFGPDLLGFLDRHYD<br>NSLENIGRANSYVWYGPRWAQAATAPSRLYKAFTTQGGIRVPALVRYPRLSRQGAISH<br>AFATVMDVTPTLLDLAGVRHPGKRWRGREIAEPRGRSWLGWLSGETEAAHDENTV<br>TGWELFGMRAIRQGDWKAVYLPAPVGPATWQLYDLARDPGEIHDLADSQPGKLAEL<br>IEHWKRYVSETGVVEGASPFLVR<br>(PaSA139V/R155E/T160S/L325W) |
| 133 | MSKRPNFLVIVADDLGFSDIGAFGGEIATPNLDALAIAGLRLTDFHTASTCSPTRSMLL<br>TGTDHHIAGIGTMAEGLTPELEGKPGYEGHLNERVVALPELLREAGYQTLMAGKWH<br>LGLKPEQTPHARGFERSFSLLPGVANHYGEEPPYDESTP<u>E</u>ILKGSPALYVEDERYLDTL<br>PEGFYSSDAFGDKLLQYLKERDQSRPFFAYLPFSAPHWPLQAPREIVEKYRGRYDAGP<br>EALRQERLARLKELGLVEADVEAHPVLALTREWEALEDEERAKSARAMEVYAAMVE<br>RMDWNIGRVVDYLRRQGELDNTFVLFMSDNGAEGALWEAFPKFGPDLLGFLDRHY<br>DNSLENIGRANSYVWYGPRWAQAATAPSRLYKAFTTQGGIRVPALVRYPRLSRQGAIS<br>HAFATVMDVTPTLLDLAGVRHPGKRWRGREIAEPRGRSWLGWLSGETEAAHDENT<br>VTGWELFGMRAIRQGDWKAVYLPAPVGPATWQLYDLARDPGEIHDLADSQPGKLAE<br>LIEHWKRYVSETGVVEGASPFLVR<br>(PaSA139V/R155E/T160S/L325W/A75G) |

The invention claimed is:

1. A variant *Pseudomonas aeruginosa* sulfatase (PaS) enzyme comprising an amino acid substitution at an amino acid position corresponding to A139, of a parental PaS enzyme comprising the amino acid sequence shown in SEQ ID NO: 1.

2. The variant PaS enzyme of claim 1, which comprises an amino acid substitution selected from the group consisting of A139C, A139I, A139L, A139S and A139V.

3. The variant PaS enzyme of claim 1, which comprises an amino acid substitution at amino acid position A139 and at least one additional amino acid substitution at a position (s) selected from the group consisting of A75, R155, I156, K158, T160, I220, A323, L325, F328, K330 and M465.

4. The variant PaS enzyme of claim 3, which comprises at least two amino acid substitutions at amino acid positions selected from the group consisting of A139/F328; A139/R155; A139/I156; A139/I220; A139/L325; A139/K330; A139/M465; A139/I220/R155; and A139/I220/L325.

5. The variant PaS enzyme of claim 3, which comprises at least three amino acid substitutions at amino acid positions selected from the group consisting of A139/R155/L325; A139/K158/L325; A139/L325/F328; and A139/L325/M465.

6. The variant PaS enzyme of claim 3, which comprises at least four amino acid substitutions at amino acid positions selected from the group consisting of A139/R155/K158/L325; A139/R155/A323/L325; A139/R155/L325/F328; A139/R155/L325/M465; A75/A139/R155/L325; and A139/R155/T160/L325.

7. The variant PaS enzyme of claim 1, which comprises the amino acid sequence shown in SEQ ID NO: 6.

8. A variant *Pseudomonas aeruginosa* sulfatase (PaS) enzyme comprising an amino acid substitution as compared to a parental PaS enzyme comprising the amino acid sequence shown in SEQ ID NO: 1, wherein the amino acid substitution is selected from the group consisting of A139C, A139I, A139L, A139S and A139V.

9. A formulation comprising the variant PaS enzyme of claim 1 and at least one excipient.

* * * * *

SEQUENCE LISTING

```
Sequence total quantity: 133
SEQ ID NO: 1              moltype = AA  length = 536
FEATURE                   Location/Qualifiers
REGION                    1..536
                          note = misc_feature - PaS: Pseudomonas aeruginosa sulfatase
source                    1..536
                          mol_type = protein
                          organism = Pseudomonas aeruginosa
SEQUENCE: 1
MSKRPNFLVI VADDLGFSDI GAFGGEIATP NLDALAIAGL RLTDFHTAST CSPTRSMLLT  60
GTDHHIAGIG TMAEALTPEL EGKPGYEGHL NERVVALPEL LREAGYQTLM AGKWHLGLKP  120
EQTPHARGFE RSFSLLPGAA NHYGFEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 2              moltype = AA  length = 536
FEATURE                   Location/Qualifiers
REGION                    1..536
                          note = Synthetic: PaSA139C
source                    1..536
                          mol_type = protein
                          organism = synthetic construct
SEQUENCE: 2
MSKRPNFLVI VADDLGFSDI GAFGGEIATP NLDALAIAGL RLTDFHTAST CSPTRSMLLT  60
```

```
GTDHHIAGIG TMAEALTPEL EGKPGYEGHL NERVVALPEL LREAGYQTLM AGKWHLGLKP    120
EQTPHARGFE RSFSLLPGCA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR       536

SEQ ID NO: 3                moltype = AA   length = 536
FEATURE                     Location/Qualifiers
REGION                      1..536
                            note = Synthetic: PaSA139I
source                      1..536
                            mol_type = protein
                            organism = synthetic construct
SEQUENCE: 3
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGIA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR       536

SEQ ID NO: 4                moltype = AA   length = 536
FEATURE                     Location/Qualifiers
REGION                      1..536
                            note = Synthetic: PaSA139L
source                      1..536
                            mol_type = protein
                            organism = synthetic construct
SEQUENCE: 4
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGLA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR       536

SEQ ID NO: 5                moltype = AA   length = 536
FEATURE                     Location/Qualifiers
REGION                      1..536
                            note = Synthetic: PaSA139S
source                      1..536
                            mol_type = protein
                            organism = synthetic construct
SEQUENCE: 5
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGSA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR       536

SEQ ID NO: 6                moltype = AA   length = 536
FEATURE                     Location/Qualifiers
REGION                      1..536
                            note = Synthetic: PaSA139V
source                      1..536
                            mol_type = protein
                            organism = synthetic construct
SEQUENCE: 6
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
```

```
PVGPATWQLY DLARDPGEIH DLADSQPGKL AELIEHWKRY VSETGVVEGA SPFLVR         536

SEQ ID NO: 7              moltype = AA  length = 536
FEATURE                   Location/Qualifiers
REGION                    1..536
                          note = Synthetic: PaSR155D
source                    1..536
                          mol_type = protein
                          organism = synthetic construct
SEQUENCE: 7
MSKRPNFLVI VADDLGFSDI GAFGGEIATP NLDALAIAGL RLTDFHTAST CSPTRSMLLT      60
GTDHHIAGIG TMAEALTPEL EGKPGYEGHL NERVVALPEL LREAGYQTLM AGKWHLGLKP     120
EQTPHARGFE RSFSLLPGAA NHYGFEPPYD ESTPDILKGT PALYVEDERY LDTLPEGFYS     180
SDAFGDKLLQ YLKERDQSRP FFAYLPFSAP HWPLQAPREI VEKYRGRYDA GPEALRQERL     240
ARLKELGLVE ADVEAHPVLA LTREWEALED EERAKSARAM EVYAAMVERM DWNIGRVVDY     300
LRRQGELDNT FVLFMSDNGA EGALLEAFPK FGPDLLGFLD RHYDNSLENI GRANSYVWYG     360
PRWAQAATAP SRLYKAFTTQ GGIRVPALVR YPRLSRQGAI SHAFATVMDV TPTLLDLAGV     420
RHPGKRWRGR EIAEPRGRSW LGWLSGETEA AHDENTVTGW ELFGMRAIRQ GDWKAVYLPA     480
PVGPATWQLY DLARDPGEIH DLADSQPGKL AELIEHWKRY VSETGVVEGA SPFLVR         536

SEQ ID NO: 8              moltype = AA  length = 536
FEATURE                   Location/Qualifiers
REGION                    1..536
                          note = Synthetic: PaSR155E
source                    1..536
                          mol_type = protein
                          organism = synthetic construct
SEQUENCE: 8
MSKRPNFLVI VADDLGFSDI GAFGGEIATP NLDALAIAGL RLTDFHTAST CSPTRSMLLT      60
GTDHHIAGIG TMAEALTPEL EGKPGYEGHL NERVVALPEL LREAGYQTLM AGKWHLGLKP     120
EQTPHARGFE RSFSLLPGAA NHYGFEPPYD ESTPEILKGT PALYVEDERY LDTLPEGFYS     180
SDAFGDKLLQ YLKERDQSRP FFAYLPFSAP HWPLQAPREI VEKYRGRYDA GPEALRQERL     240
ARLKELGLVE ADVEAHPVLA LTREWEALED EERAKSARAM EVYAAMVERM DWNIGRVVDY     300
LRRQGELDNT FVLFMSDNGA EGALLEAFPK FGPDLLGFLD RHYDNSLENI GRANSYVWYG     360
PRWAQAATAP SRLYKAFTTQ GGIRVPALVR YPRLSRQGAI SHAFATVMDV TPTLLDLAGV     420
RHPGKRWRGR EIAEPRGRSW LGWLSGETEA AHDENTVTGW ELFGMRAIRQ GDWKAVYLPA     480
PVGPATWQLY DLARDPGEIH DLADSQPGKL AELIEHWKRY VSETGVVEGA SPFLVR         536

SEQ ID NO: 9              moltype = AA  length = 536
FEATURE                   Location/Qualifiers
REGION                    1..536
                          note = Synthetic: PaSR155G
source                    1..536
                          mol_type = protein
                          organism = synthetic construct
SEQUENCE: 9
MSKRPNFLVI VADDLGFSDI GAFGGEIATP NLDALAIAGL RLTDFHTAST CSPTRSMLLT      60
GTDHHIAGIG TMAEALTPEL EGKPGYEGHL NERVVALPEL LREAGYQTLM AGKWHLGLKP     120
EQTPHARGFE RSFSLLPGAA NHYGFEPPYD ESTPGILKGT PALYVEDERY LDTLPEGFYS     180
SDAFGDKLLQ YLKERDQSRP FFAYLPFSAP HWPLQAPREI VEKYRGRYDA GPEALRQERL     240
ARLKELGLVE ADVEAHPVLA LTREWEALED EERAKSARAM EVYAAMVERM DWNIGRVVDY     300
LRRQGELDNT FVLFMSDNGA EGALLEAFPK FGPDLLGFLD RHYDNSLENI GRANSYVWYG     360
PRWAQAATAP SRLYKAFTTQ GGIRVPALVR YPRLSRQGAI SHAFATVMDV TPTLLDLAGV     420
RHPGKRWRGR EIAEPRGRSW LGWLSGETEA AHDENTVTGW ELFGMRAIRQ GDWKAVYLPA     480
PVGPATWQLY DLARDPGEIH DLADSQPGKL AELIEHWKRY VSETGVVEGA SPFLVR         536

SEQ ID NO: 10             moltype = AA  length = 536
FEATURE                   Location/Qualifiers
REGION                    1..536
                          note = Synthetic: PaSR155P
source                    1..536
                          mol_type = protein
                          organism = synthetic construct
SEQUENCE: 10
MSKRPNFLVI VADDLGFSDI GAFGGEIATP NLDALAIAGL RLTDFHTAST CSPTRSMLLT      60
GTDHHIAGIG TMAEALTPEL EGKPGYEGHL NERVVALPEL LREAGYQTLM AGKWHLGLKP     120
EQTPHARGFE RSFSLLPGAA NHYGFEPPYD ESTPPILKGT PALYVEDERY LDTLPEGFYS     180
SDAFGDKLLQ YLKERDQSRP FFAYLPFSAP HWPLQAPREI VEKYRGRYDA GPEALRQERL     240
ARLKELGLVE ADVEAHPVLA LTREWEALED EERAKSARAM EVYAAMVERM DWNIGRVVDY     300
LRRQGELDNT FVLFMSDNGA EGALLEAFPK FGPDLLGFLD RHYDNSLENI GRANSYVWYG     360
PRWAQAATAP SRLYKAFTTQ GGIRVPALVR YPRLSRQGAI SHAFATVMDV TPTLLDLAGV     420
RHPGKRWRGR EIAEPRGRSW LGWLSGETEA AHDENTVTGW ELFGMRAIRQ GDWKAVYLPA     480
PVGPATWQLY DLARDPGEIH DLADSQPGKL AELIEHWKRY VSETGVVEGA SPFLVR         536

SEQ ID NO: 11             moltype = AA  length = 536
FEATURE                   Location/Qualifiers
REGION                    1..536
                          note = Synthetic: PaSR155Q
source                    1..536
```

```
                              mol_type = protein
                              organism = synthetic construct
SEQUENCE: 11
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGAA NHYGFEPPYD ESTPQILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 12             moltype = AA  length = 536
FEATURE                   Location/Qualifiers
REGION                    1..536
                          note = Synthetic: PaSR155V
source                    1..536
                          mol_type = protein
                          organism = synthetic construct
SEQUENCE: 12
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGAA NHYGFEPPYD ESTPVILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 13             moltype = AA  length = 536
FEATURE                   Location/Qualifiers
REGION                    1..536
                          note = Synthetic: PaSL325F
source                    1..536
                          mol_type = protein
                          organism = synthetic construct
SEQUENCE: 13
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGAA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALFEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 14             moltype = AA  length = 536
FEATURE                   Location/Qualifiers
REGION                    1..536
                          note = Synthetic: PaSL325W
source                    1..536
                          mol_type = protein
                          organism = synthetic construct
SEQUENCE: 14
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGAA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 15             moltype = AA  length = 536
FEATURE                   Location/Qualifiers
REGION                    1..536
                          note = Synthetic: PaSL325Y
source                    1..536
                          mol_type = protein
                          organism = synthetic construct
SEQUENCE: 15
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGAA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
```

```
ARLKELGLVE ADVEAHPVLA LTREWEALED EERAKSARAM EVYAAMVERM DWNIGRVVDY    300
LRRQGELDNT FVLFMSDNGA EGALYEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 16          moltype = AA   length = 536
FEATURE                Location/Qualifiers
REGION                 1..536
                       note = Synthetic: PaSF328C
source                 1..536
                       mol_type = protein
                       organism = synthetic construct
SEQUENCE: 16
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGAA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEACPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 17          moltype = AA   length = 536
FEATURE                Location/Qualifiers
REGION                 1..536
                       note = Synthetic: PaSF328S
source                 1..536
                       mol_type = protein
                       organism = synthetic construct
SEQUENCE: 17
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGAA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEASPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 18          moltype = AA   length = 536
FEATURE                Location/Qualifiers
REGION                 1..536
                       note = Synthetic: PaSF328W
source                 1..536
                       mol_type = protein
                       organism = synthetic construct
SEQUENCE: 18
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGAA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAWPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 19          moltype = AA   length = 536
FEATURE                Location/Qualifiers
REGION                 1..536
                       note = Synthetic: PaSK330T
source                 1..536
                       mol_type = protein
                       organism = synthetic construct
SEQUENCE: 19
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGAA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAWPT FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 20          moltype = AA   length = 536
```

```
FEATURE                 Location/Qualifiers
REGION                  1..536
                        note = Synthetic: PaSA376E
source                  1..536
                        mol_type = protein
                        organism = synthetic construct
SEQUENCE: 20
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGAA NHYGFEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPK FGPDLLGFLD RHYDNSLENI GRANSYVWYG  360
PRWAQAATAP SRLYKEFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 21           moltype = AA  length = 536
FEATURE                 Location/Qualifiers
REGION                  1..536
                        note = Synthetic: PaSA376H
source                  1..536
                        mol_type = protein
                        organism = synthetic construct
SEQUENCE: 21
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGAA NHYGFEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPK FGPDLLGFLD RHYDNSLENI GRANSYVWYG  360
PRWAQAATAP SRLYKHFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 22           moltype = AA  length = 536
FEATURE                 Location/Qualifiers
REGION                  1..536
                        note = Synthetic: PaSA376I
source                  1..536
                        mol_type = protein
                        organism = synthetic construct
SEQUENCE: 22
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGAA NHYGFEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPK FGPDLLGFLD RHYDNSLENI GRANSYVWYG  360
PRWAQAATAP SRLYKIFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 23           moltype = AA  length = 536
FEATURE                 Location/Qualifiers
REGION                  1..536
                        note = Synthetic: PaSA376S
source                  1..536
                        mol_type = protein
                        organism = synthetic construct
SEQUENCE: 23
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGAA NHYGFEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPK FGPDLLGFLD RHYDNSLENI GRANSYVWYG  360
PRWAQAATAP SRLYKSFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 24           moltype = AA  length = 536
FEATURE                 Location/Qualifiers
REGION                  1..536
                        note = Synthetic: PaSA376T
source                  1..536
                        mol_type = protein
                        organism = synthetic construct
SEQUENCE: 24
```

```
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGAA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKTFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 25           moltype = AA  length = 536
FEATURE                 Location/Qualifiers
REGION                  1..536
                        note = Synthetic: PaSA376V
source                  1..536
                        mol_type = protein
                        organism = synthetic construct
SEQUENCE: 25
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGAA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKVFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 26           moltype = AA  length = 536
FEATURE                 Location/Qualifiers
REGION                  1..536
                        note = Synthetic: PaSF377C
source                  1..536
                        mol_type = protein
                        organism = synthetic construct
SEQUENCE: 26
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGAA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKVCTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 27           moltype = AA  length = 536
FEATURE                 Location/Qualifiers
REGION                  1..536
                        note = Synthetic: PaSF377V
source                  1..536
                        mol_type = protein
                        organism = synthetic construct
SEQUENCE: 27
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGAA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKVVTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 28           moltype = AA  length = 536
FEATURE                 Location/Qualifiers
REGION                  1..536
                        note = Synthetic: PaSF377W
source                  1..536
                        mol_type = protein
                        organism = synthetic construct
SEQUENCE: 28
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGAA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKVWTTQ GGIRVPALVR YPRLSRQGAI SHAFATVMDV TPTLLDLAGV   420
```

```
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 29            moltype = AA  length = 536
FEATURE                  Location/Qualifiers
REGION                   1..536
                         note = Synthetic: PaSM465Q
source                   1..536
                         mol_type = protein
                         organism = synthetic construct
SEQUENCE: 29
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGAA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGQRAIRQ GDWKAVYLPA    480
PVGPATWQLY DLARDPGEIH DLADSQPGKL AELIEHWKRY VSETGVVEGA SPFLVR        536

SEQ ID NO: 30            moltype = AA  length = 536
FEATURE                  Location/Qualifiers
REGION                   1..536
                         note = Synthetic: PaSM465S
source                   1..536
                         mol_type = protein
                         organism = synthetic construct
SEQUENCE: 30
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGAA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGSRAIRQ GDWKAVYLPA    480
PVGPATWQLY DLARDPGEIH DLADSQPGKL AELIEHWKRY VSETGVVEGA SPFLVR        536

SEQ ID NO: 31            moltype = AA  length = 536
FEATURE                  Location/Qualifiers
REGION                   1..536
                         note = Synthetic: PaSM465T
source                   1..536
                         mol_type = protein
                         organism = synthetic construct
SEQUENCE: 31
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGAA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGTRAIRQ GDWKAVYLPA    480
PVGPATWQLY DLARDPGEIH DLADSQPGKL AELIEHWKRY VSETGVVEGA SPFLVR        536

SEQ ID NO: 32            moltype = AA  length = 536
FEATURE                  Location/Qualifiers
REGION                   1..536
                         note = Synthetic: PaSA139V/R155C
source                   1..536
                         mol_type = protein
                         organism = synthetic construct
SEQUENCE: 32
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPCILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 33            moltype = AA  length = 536
FEATURE                  Location/Qualifiers
REGION                   1..536
                         note = Synthetic: PaSA139V/R155D
```

```
source                        1..536
                              mol_type = protein
                              organism = synthetic construct
SEQUENCE: 33
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGFEPPYD ESTPDILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR     536

SEQ ID NO: 34                 moltype = AA   length = 536
FEATURE                       Location/Qualifiers
REGION                        1..536
                              note = Synthetic: PaSA139V/R155E
source                        1..536
                              mol_type = protein
                              organism = synthetic construct
SEQUENCE: 34
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGFEPPYD ESTPEILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR     536

SEQ ID NO: 35                 moltype = AA   length = 536
FEATURE                       Location/Qualifiers
REGION                        1..536
                              note = Synthetic: PaSA139V/R155G
source                        1..536
                              mol_type = protein
                              organism = synthetic construct
SEQUENCE: 35
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGFEPPYD ESTPGILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR     536

SEQ ID NO: 36                 moltype = AA   length = 536
FEATURE                       Location/Qualifiers
REGION                        1..536
                              note = Synthetic: PaSA139V/R155K
source                        1..536
                              mol_type = protein
                              organism = synthetic construct
SEQUENCE: 36
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGFEPPYD ESTPKILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR     536

SEQ ID NO: 37                 moltype = AA   length = 536
FEATURE                       Location/Qualifiers
REGION                        1..536
                              note = Synthetic: PaSA139V/R155L
source                        1..536
                              mol_type = protein
                              organism = synthetic construct
SEQUENCE: 37
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGFEPPYD ESTPLILKGT PALYVEDERY LDTLPEGFYS  180
```

```
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 38            moltype = AA  length = 536
FEATURE                  Location/Qualifiers
REGION                   1..536
                         note = Synthetic: PaSA139V/R155S
source                   1..536
                         mol_type = protein
                         organism = synthetic construct
SEQUENCE: 38
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPSILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 39            moltype = AA  length = 536
FEATURE                  Location/Qualifiers
REGION                   1..536
                         note = Synthetic: PaSA139V/R155V
source                   1..536
                         mol_type = protein
                         organism = synthetic construct
SEQUENCE: 39
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPVILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 40            moltype = AA  length = 536
FEATURE                  Location/Qualifiers
REGION                   1..536
                         note = Synthetic: PaSA139V/R155W
source                   1..536
                         mol_type = protein
                         organism = synthetic construct
SEQUENCE: 40
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPWILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 41            moltype = AA  length = 536
FEATURE                  Location/Qualifiers
REGION                   1..536
                         note = Synthetic: PaSR155E/I220M
source                   1..536
                         mol_type = protein
                         organism = synthetic construct
SEQUENCE: 41
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGAA NHYGFEPPYD ESTPEILKGT PALYVEDERY LDTLPEGFYS    180
SDAFGDKLLQ YLKERDQSRP FFAYLPFSAP HWPLQAPREM VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536
```

```
SEQ ID NO: 42            moltype = AA   length = 536
FEATURE                  Location/Qualifiers
REGION                   1..536
                         note = Synthetic: PaSA139V/I156A
source                   1..536
                         mol_type = protein
                         organism = synthetic construct
SEQUENCE: 42
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRALKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 43            moltype = AA   length = 536
FEATURE                  Location/Qualifiers
REGION                   1..536
                         note = Synthetic: PaSA139V/I156D
source                   1..536
                         mol_type = protein
                         organism = synthetic construct
SEQUENCE: 43
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRDLKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 44            moltype = AA   length = 536
FEATURE                  Location/Qualifiers
REGION                   1..536
                         note = Synthetic: PaSA139V/I156E
source                   1..536
                         mol_type = protein
                         organism = synthetic construct
SEQUENCE: 44
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRELKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 45            moltype = AA   length = 536
FEATURE                  Location/Qualifiers
REGION                   1..536
                         note = Synthetic: PaSA139V/I156G
source                   1..536
                         mol_type = protein
                         organism = synthetic construct
SEQUENCE: 45
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRGLKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 46            moltype = AA   length = 536
FEATURE                  Location/Qualifiers
REGION                   1..536
                         note = Synthetic: PaSA139V/I156T
source                   1..536
                         mol_type = protein
                         organism = synthetic construct
```

```
SEQUENCE: 46
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRTLKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 47          moltype = AA   length = 536
FEATURE                Location/Qualifiers
REGION                 1..536
                       note = Synthetic: PaSA139V/I156W
source                 1..536
                       mol_type = protein
                       organism = synthetic construct
SEQUENCE: 47
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRWLKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 48          moltype = AA   length = 536
FEATURE                Location/Qualifiers
REGION                 1..536
                       note = Synthetic: PaSA139V/I220M
source                 1..536
                       mol_type = protein
                       organism = synthetic construct
SEQUENCE: 48
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPEILKGT PALYVEDERY LDTLPEGFYS   180
SDAFGDKLLQ YLKERDQSRP FFAYLPFSAP HWPLQAPREM VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 49          moltype = AA   length = 536
FEATURE                Location/Qualifiers
REGION                 1..536
                       note = Synthetic: PaSA139V/L325C
source                 1..536
                       mol_type = protein
                       organism = synthetic construct
SEQUENCE: 49
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALCEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 50          moltype = AA   length = 536
FEATURE                Location/Qualifiers
REGION                 1..536
                       note = Synthetic: PaSA139V/L325H
source                 1..536
                       mol_type = protein
                       organism = synthetic construct
SEQUENCE: 50
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALHEAFPK FGPDLLGFLD RHYDNSLENI GRANSYVWYG   360
```

```
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 51            moltype = AA   length = 536
FEATURE                  Location/Qualifiers
REGION                   1..536
                         note = Synthetic: PaSA139V/L325G
source                   1..536
                         mol_type = protein
                         organism = synthetic construct
SEQUENCE: 51
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALGEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 52            moltype = AA   length = 536
FEATURE                  Location/Qualifiers
REGION                   1..536
                         note = Synthetic: PaSA139V/L325K
source                   1..536
                         mol_type = protein
                         organism = synthetic construct
SEQUENCE: 52
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALKEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 53            moltype = AA   length = 536
FEATURE                  Location/Qualifiers
REGION                   1..536
                         note = Synthetic: PaSA139V/L325P
source                   1..536
                         mol_type = protein
                         organism = synthetic construct
SEQUENCE: 53
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALPEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 54            moltype = AA   length = 536
FEATURE                  Location/Qualifiers
REGION                   1..536
                         note = Synthetic: PaSA139V/L325T
source                   1..536
                         mol_type = protein
                         organism = synthetic construct
SEQUENCE: 54
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALTEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 55            moltype = AA   length = 536
FEATURE                  Location/Qualifiers
REGION                   1..536
```

```
                            note        = Synthetic: PaSA139V/L325V
source                      1..536
                            mol_type    = protein
                            organism    = synthetic construct
SEQUENCE: 55
MSKRPNFLVI VADDLGFSDI GAFGGEIATP NLDALAIAGL RLTDFHTAST CSPTRSMLLT  60
GTDHHIAGIG TMAEALTPEL EGKPGYEGHL NERVVALPEL LREAGYQTLM AGKWHLGLKP 120
EQTPHARGFE RSFSLLPGVA NHYGFEPPYD ESTPRILKGT PALYVEDERY LDTLPEGFYS 180
SDAFGDKLLQ YLKERDQSRP FFAYLPFSAP HWPLQAPREI VEKYRGRYDA GPEALRQERL 240
ARLKELGLVE ADVEAHPVLA LTREWEALED EERAKSARAM EVYAAMVERM DWNIGRVVDY 300
LRRQGELDNT FVLFMSDNGA EGALVEAFPK FGPDLLGFLD RHYDNSLENI GRANSYVWYG 360
PRWAQAATAP SRLYKAFTTQ GGIRVPALVR YPRLSRQGAI SHAFATVMDV TPTLLDLAGV 420
RHPGKRWRGR EIAEPRGRSW LGWLSGETEA AHDENTVTGW ELFGMRAIRQ GDWKAVYLPA 480
PVGPATWQLY DLARDPGEIH DLADSQPGKL AELIEHWKRY VSETGVVEGA SPFLVR     536

SEQ ID NO: 56               moltype = AA   length = 536
FEATURE                     Location/Qualifiers
REGION                      1..536
                            note        = Synthetic: PaSA139V/L325Y
source                      1..536
                            mol_type    = protein
                            organism    = synthetic construct
SEQUENCE: 56
MSKRPNFLVI VADDLGFSDI GAFGGEIATP NLDALAIAGL RLTDFHTAST CSPTRSMLLT  60
GTDHHIAGIG TMAEALTPEL EGKPGYEGHL NERVVALPEL LREAGYQTLM AGKWHLGLKP 120
EQTPHARGFE RSFSLLPGVA NHYGFEPPYD ESTPRILKGT PALYVEDERY LDTLPEGFYS 180
SDAFGDKLLQ YLKERDQSRP FFAYLPFSAP HWPLQAPREI VEKYRGRYDA GPEALRQERL 240
ARLKELGLVE ADVEAHPVLA LTREWEALED EERAKSARAM EVYAAMVERM DWNIGRVVDY 300
LRRQGELDNT FVLFMSDNGA EGALYEAFPK FGPDLLGFLD RHYDNSLENI GRANSYVWYG 360
PRWAQAATAP SRLYKAFTTQ GGIRVPALVR YPRLSRQGAI SHAFATVMDV TPTLLDLAGV 420
RHPGKRWRGR EIAEPRGRSW LGWLSGETEA AHDENTVTGW ELFGMRAIRQ GDWKAVYLPA 480
PVGPATWQLY DLARDPGEIH DLADSQPGKL AELIEHWKRY VSETGVVEGA SPFLVR     536

SEQ ID NO: 57               moltype = AA   length = 536
FEATURE                     Location/Qualifiers
REGION                      1..536
                            note        = Synthetic: PaSA139V/L325W
source                      1..536
                            mol_type    = protein
                            organism    = synthetic construct
SEQUENCE: 57
MSKRPNFLVI VADDLGFSDI GAFGGEIATP NLDALAIAGL RLTDFHTAST CSPTRSMLLT  60
GTDHHIAGIG TMAEALTPEL EGKPGYEGHL NERVVALPEL LREAGYQTLM AGKWHLGLKP 120
EQTPHARGFE RSFSLLPGVA NHYGFEPPYD ESTPRILKGT PALYVEDERY LDTLPEGFYS 180
SDAFGDKLLQ YLKERDQSRP FFAYLPFSAP HWPLQAPREI VEKYRGRYDA GPEALRQERL 240
ARLKELGLVE ADVEAHPVLA LTREWEALED EERAKSARAM EVYAAMVERM DWNIGRVVDY 300
LRRQGELDNT FVLFMSDNGA EGALWEAFPK FGPDLLGFLD RHYDNSLENI GRANSYVWYG 360
PRWAQAATAP SRLYKAFTTQ GGIRVPALVR YPRLSRQGAI SHAFATVMDV TPTLLDLAGV 420
RHPGKRWRGR EIAEPRGRSW LGWLSGETEA AHDENTVTGW ELFGMRAIRQ GDWKAVYLPA 480
PVGPATWQLY DLARDPGEIH DLADSQPGKL AELIEHWKRY VSETGVVEGA SPFLVR     536

SEQ ID NO: 58               moltype = AA   length = 536
FEATURE                     Location/Qualifiers
REGION                      1..536
                            note        = Synthetic: PaSA139V/L325F
source                      1..536
                            mol_type    = protein
                            organism    = synthetic construct
SEQUENCE: 58
MSKRPNFLVI VADDLGFSDI GAFGGEIATP NLDALAIAGL RLTDFHTAST CSPTRSMLLT  60
GTDHHIAGIG TMAEALTPEL EGKPGYEGHL NERVVALPEL LREAGYQTLM AGKWHLGLKP 120
EQTPHARGFE RSFSLLPGVA NHYGFEPPYD ESTPRILKGT PALYVEDERY LDTLPEGFYS 180
SDAFGDKLLQ YLKERDQSRP FFAYLPFSAP HWPLQAPREI VEKYRGRYDA GPEALRQERL 240
ARLKELGLVE ADVEAHPVLA LTREWEALED EERAKSARAM EVYAAMVERM DWNIGRVVDY 300
LRRQGELDNT FVLFMSDNGA EGALFEAFPK FGPDLLGFLD RHYDNSLENI GRANSYVWYG 360
PRWAQAATAP SRLYKAFTTQ GGIRVPALVR YPRLSRQGAI SHAFATVMDV TPTLLDLAGV 420
RHPGKRWRGR EIAEPRGRSW LGWLSGETEA AHDENTVTGW ELFGMRAIRQ GDWKAVYLPA 480
PVGPATWQLY DLARDPGEIH DLADSQPGKL AELIEHWKRY VSETGVVEGA SPFLVR     536

SEQ ID NO: 59               moltype = AA   length = 536
FEATURE                     Location/Qualifiers
REGION                      1..536
                            note        = Synthetic: PaSL325Y/I220M
source                      1..536
                            mol_type    = protein
                            organism    = synthetic construct
SEQUENCE: 59
MSKRPNFLVI VADDLGFSDI GAFGGEIATP NLDALAIAGL RLTDFHTAST CSPTRSMLLT  60
GTDHHIAGIG TMAEALTPEL EGKPGYEGHL NERVVALPEL LREAGYQTLM AGKWHLGLKP 120
```

```
EQTPHARGFE RSFSLLPGAA NHYGFEPPYD ESTPRILKGT PALYVEDERY LDTLPEGFYS    180
SDAFGDKLLQ YLKERDQSRP FFAYLPFSAP HWPLQAPREM VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALYEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 60              moltype = AA  length = 536
FEATURE                    Location/Qualifiers
REGION                     1..536
                           note = Synthetic: PaSA139V/F328A
source                     1..536
                           mol_type = protein
                           organism = synthetic construct
SEQUENCE: 60
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAAPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 61              moltype = AA  length = 536
FEATURE                    Location/Qualifiers
REGION                     1..536
                           note = Synthetic: PaSA139V/F328C
source                     1..536
                           mol_type = protein
                           organism = synthetic construct
SEQUENCE: 61
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEACPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 62              moltype = AA  length = 536
FEATURE                    Location/Qualifiers
REGION                     1..536
                           note = Synthetic: PaSA139V/F328L
source                     1..536
                           mol_type = protein
                           organism = synthetic construct
SEQUENCE: 62
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEALPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 63              moltype = AA  length = 536
FEATURE                    Location/Qualifiers
REGION                     1..536
                           note = Synthetic: PaSA139V/F328W
source                     1..536
                           mol_type = protein
                           organism = synthetic construct
SEQUENCE: 63
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAWPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536
```

```
SEQ ID NO: 64           moltype = AA   length = 536
FEATURE                 Location/Qualifiers
REGION                  1..536
                        note = Synthetic: PaSA139V/K330D
source                  1..536
                        mol_type = protein
                        organism = synthetic construct
SEQUENCE: 64
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGFEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPD FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR     536

SEQ ID NO: 65           moltype = AA   length = 536
FEATURE                 Location/Qualifiers
REGION                  1..536
                        note = Synthetic: PaSA139V/K330S
source                  1..536
                        mol_type = protein
                        organism = synthetic construct
SEQUENCE: 65
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGFEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPS FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR     536

SEQ ID NO: 66           moltype = AA   length = 536
FEATURE                 Location/Qualifiers
REGION                  1..536
                        note = Synthetic: PaSA139V/K330T
source                  1..536
                        mol_type = protein
                        organism = synthetic construct
SEQUENCE: 66
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGFEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPT FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR     536

SEQ ID NO: 67           moltype = AA   length = 536
FEATURE                 Location/Qualifiers
REGION                  1..536
                        note = Synthetic: PaSA139V/K330V
source                  1..536
                        mol_type = protein
                        organism = synthetic construct
SEQUENCE: 67
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGFEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALLEAFPV FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR     536

SEQ ID NO: 68           moltype = AA   length = 536
FEATURE                 Location/Qualifiers
REGION                  1..536
                        note = Synthetic: PaSA139V/K330Y
source                  1..536
                        mol_type = protein
```

```
                          organism = synthetic construct
SEQUENCE: 68
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPY FGPDLLGFLD RHYDNSLENI GRANSYVWYG   360
PRWAQAATAP SRLYKAFTTQ GGIRVQPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 69             moltype = AA  length = 536
FEATURE                   Location/Qualifiers
REGION                    1..536
                          note = Synthetic: PaSA139V/M465F
source                    1..536
                          mol_type = protein
                          organism = synthetic construct
SEQUENCE: 69
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGFRAIRQ GDWKAVYLPA   480
PVGPATWQLY DLARDPGEIH DLADSQPGKL AELIEHWKRY VSETGVVEGA SPFLVR       536

SEQ ID NO: 70             moltype = AA  length = 536
FEATURE                   Location/Qualifiers
REGION                    1..536
                          note = Synthetic: PaSA139V/M465I
source                    1..536
                          mol_type = protein
                          organism = synthetic construct
SEQUENCE: 70
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGIRAIRQ GDWKAVYLPA   480
PVGPATWQLY DLARDPGEIH DLADSQPGKL AELIEHWKRY VSETGVVEGA SPFLVR       536

SEQ ID NO: 71             moltype = AA  length = 536
FEATURE                   Location/Qualifiers
REGION                    1..536
                          note = Synthetic: PaSA139V/M465Q
source                    1..536
                          mol_type = protein
                          organism = synthetic construct
SEQUENCE: 71
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALLEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGQRAIRQ GDWKAVYLPA   480
PVGPATWQLY DLARDPGEIH DLADSQPGKL AELIEHWKRY VSETGVVEGA SPFLVR       536

SEQ ID NO: 72             moltype = AA  length = 536
FEATURE                   Location/Qualifiers
REGION                    1..536
                          note = Synthetic: PaSA139V/M465S
source                    1..536
                          mol_type = protein
                          organism = synthetic construct
SEQUENCE: 72
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGFEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
```

```
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGSRAIRQ GDWKAVYLPA    480
PVGPATWQLY DLARDPGEIH DLADSQPGKL AELIEHWKRY VSETGVVEGA SPFLVR        536

SEQ ID NO: 73           moltype = AA  length = 536
FEATURE                 Location/Qualifiers
REGION                  1..536
                        note = Synthetic: PaSA139V/M465E
source                  1..536
                        mol_type = protein
                        organism = synthetic construct
SEQUENCE: 73
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGERAIRQ GDWKAVYLPA    480
PVGPATWQLY DLARDPGEIH DLADSQPGKL AELIEHWKRY VSETGVVEGA SPFLVR        536

SEQ ID NO: 74           moltype = AA  length = 536
FEATURE                 Location/Qualifiers
REGION                  1..536
                        note = Synthetic: PaSA139V/M465P
source                  1..536
                        mol_type = protein
                        organism = synthetic construct
SEQUENCE: 74
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGPRAIRQ GDWKAVYLPA    480
PVGPATWQLY DLARDPGEIH DLADSQPGKL AELIEHWKRY VSETGVVEGA SPFLVR        536

SEQ ID NO: 75           moltype = AA  length = 536
FEATURE                 Location/Qualifiers
REGION                  1..536
                        note = Synthetic: PaSA139V/M465V
source                  1..536
                        mol_type = protein
                        organism = synthetic construct
SEQUENCE: 75
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALLEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGVRAIRQ GDWKAVYLPA    480
PVGPATWQLY DLARDPGEIH DLADSQPGKL AELIEHWKRY VSETGVVEGA SPFLVR        536

SEQ ID NO: 76           moltype = AA  length = 536
FEATURE                 Location/Qualifiers
REGION                  1..536
                        note = Synthetic: PaSA139V/L325W/R155F
source                  1..536
                        mol_type = protein
                        organism = synthetic construct
SEQUENCE: 76
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGFEPPYD ESTPFILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 77           moltype = AA  length = 536
FEATURE                 Location/Qualifiers
```

-continued

```
REGION                      1..536
                            note = Synthetic: PaSA139V/L325W/R155E
source                      1..536
                            mol_type = protein
                            organism = synthetic construct
SEQUENCE: 77
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPEILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 78               moltype = AA  length = 536
FEATURE                     Location/Qualifiers
REGION                      1..536
                            note = Synthetic: PaSA139V/L325W/R155D
source                      1..536
                            mol_type = protein
                            organism = synthetic construct
SEQUENCE: 78
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPDILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 79               moltype = AA  length = 536
FEATURE                     Location/Qualifiers
REGION                      1..536
                            note = Synthetic: PaSA139V/L325W/R155C
source                      1..536
                            mol_type = protein
                            organism = synthetic construct
SEQUENCE: 79
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPCILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 80               moltype = AA  length = 536
FEATURE                     Location/Qualifiers
REGION                      1..536
                            note = Synthetic: PaSA139V/L325W/R155K
source                      1..536
                            mol_type = protein
                            organism = synthetic construct
SEQUENCE: 80
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPKILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 81               moltype = AA  length = 536
FEATURE                     Location/Qualifiers
REGION                      1..536
                            note = Synthetic: PaSA139V/L325W/R155V
source                      1..536
                            mol_type = protein
                            organism = synthetic construct
SEQUENCE: 81
MSKRPNFLVI VADDLGFSDI GAFGGEIATP NLDALAIAGL RLTDFHTAST CSPTRSMLLT   60
```

```
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPVILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 82           moltype = AA  length = 536
FEATURE                 Location/Qualifiers
REGION                  1..536
                        note = Synthetic: PaSA139V/L325W/R155S
source                  1..536
                        mol_type = protein
                        organism = synthetic construct
SEQUENCE: 82
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPSILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 83           moltype = AA  length = 536
FEATURE                 Location/Qualifiers
REGION                  1..536
                        note = Synthetic: PaSA139V/L325W/R155L
source                  1..536
                        mol_type = protein
                        organism = synthetic construct
SEQUENCE: 83
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPLILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 84           moltype = AA  length = 536
FEATURE                 Location/Qualifiers
REGION                  1..536
                        note = Synthetic: PaSA139V/L325W/R155G
source                  1..536
                        mol_type = protein
                        organism = synthetic construct
SEQUENCE: 84
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPGILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 85           moltype = AA  length = 536
FEATURE                 Location/Qualifiers
REGION                  1..536
                        note = Synthetic: PaSA139V/L325W/K158D
source                  1..536
                        mol_type = protein
                        organism = synthetic construct
SEQUENCE: 85
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPRILDGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
```

PVGPATWQLY DLARDPGEIH DLADSQPGKL AELIEHWKRY VSETGVVEGA SPFLVR      536

```
SEQ ID NO: 86          moltype = AA  length = 536
FEATURE                Location/Qualifiers
REGION                 1..536
                       note = Synthetic: PaSA139V/L325W/K158N
source                 1..536
                       mol_type = protein
                       organism = synthetic construct
SEQUENCE: 86
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPRILNGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 87          moltype = AA  length = 536
FEATURE                Location/Qualifiers
REGION                 1..536
                       note = Synthetic: PaSA139V/L325W/K158W
source                 1..536
                       mol_type = protein
                       organism = synthetic construct
SEQUENCE: 87
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPRILWGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 88          moltype = AA  length = 536
FEATURE                Location/Qualifiers
REGION                 1..536
                       note = Synthetic: PaSA139V/L325W/K158I
source                 1..536
                       mol_type = protein
                       organism = synthetic construct
SEQUENCE: 88
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPRILIGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 89          moltype = AA  length = 536
FEATURE                Location/Qualifiers
REGION                 1..536
                       note = Synthetic: PaSA139V/L325W/F328W
source                 1..536
                       mol_type = protein
                       organism = synthetic construct
SEQUENCE: 89
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAWPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR      536

SEQ ID NO: 90          moltype = AA  length = 536
FEATURE                Location/Qualifiers
REGION                 1..536
                       note = Synthetic: PaSA139V/L325W/F328V
source                 1..536
```

```
                        mol_type = protein
                        organism = synthetic construct
SEQUENCE: 90
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAVPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 91          moltype = AA   length = 536
FEATURE                Location/Qualifiers
REGION                 1..536
                       note = Synthetic: PaSA139V/L325W/F328G
source                 1..536
                       mol_type = protein
                       organism = synthetic construct
SEQUENCE: 91
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAGPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 92          moltype = AA   length = 536
FEATURE                Location/Qualifiers
REGION                 1..536
                       note = Synthetic: PaSA139V/L325W/F328C
source                 1..536
                       mol_type = protein
                       organism = synthetic construct
SEQUENCE: 92
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEACPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 93          moltype = AA   length = 536
FEATURE                Location/Qualifiers
REGION                 1..536
                       note = Synthetic: PaSA139V/L325W/F328A
source                 1..536
                       mol_type = protein
                       organism = synthetic construct
SEQUENCE: 93
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAAPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 94          moltype = AA   length = 536
FEATURE                Location/Qualifiers
REGION                 1..536
                       note = Synthetic: PaSA139V/L325W/M465A
source                 1..536
                       mol_type = protein
                       organism = synthetic construct
SEQUENCE: 94
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
```

```
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGARAIRQ GDWKAVYLPA    480
PVGPATWQLY DLARDPGEIH DLADSQPGKL AELIEHWKRY VSETGVVEGA SPFLVR        536

SEQ ID NO: 95           moltype = AA  length = 536
FEATURE                 Location/Qualifiers
REGION                  1..536
                        note = Synthetic: PaSA139V/L325W/M465Y
source                  1..536
                        mol_type = protein
                        organism = synthetic construct
SEQUENCE: 95
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGYRAIRQ GDWKAVYLPA    480
PVGPATWQLY DLARDPGEIH DLADSQPGKL AELIEHWKRY VSETGVVEGA SPFLVR        536

SEQ ID NO: 96           moltype = AA  length = 536
FEATURE                 Location/Qualifiers
REGION                  1..536
                        note = Synthetic: PaSA139V/L325W/M465T
source                  1..536
                        mol_type = protein
                        organism = synthetic construct
SEQUENCE: 96
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGTRAIRQ GDWKAVYLPA    480
PVGPATWQLY DLARDPGEIH DLADSQPGKL AELIEHWKRY VSETGVVEGA SPFLVR        536

SEQ ID NO: 97           moltype = AA  length = 536
FEATURE                 Location/Qualifiers
REGION                  1..536
                        note = Synthetic: PaSA139V/L325W/M465Q
source                  1..536
                        mol_type = protein
                        organism = synthetic construct
SEQUENCE: 97
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGQRAIRQ GDWKAVYLPA    480
PVGPATWQLY DLARDPGEIH DLADSQPGKL AELIEHWKRY VSETGVVEGA SPFLVR        536

SEQ ID NO: 98           moltype = AA  length = 536
FEATURE                 Location/Qualifiers
REGION                  1..536
                        note = Synthetic: PaSA139V/L325W/M465N
source                  1..536
                        mol_type = protein
                        organism = synthetic construct
SEQUENCE: 98
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPRILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGNRAIRQ GDWKAVYLPA    480
PVGPATWQLY DLARDPGEIH DLADSQPGKL AELIEHWKRY VSETGVVEGA SPFLVR        536

SEQ ID NO: 99           moltype = AA  length = 536
```

| FEATURE | Location/Qualifiers |
|---|---|
| REGION | 1..536 |
| | note = Synthetic: PaSA139V/L325W/M465L |
| source | 1..536 |
| | mol_type = protein |
| | organism = synthetic construct |

SEQUENCE: 99
```
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGLRAIRQ GDWKAVYLPA  480
PVGPATWQLY DLARDPGEIH DLADSQPGKL AELIEHWKRY VSETGVVEGA SPFLVR      536
```

| SEQ ID NO: 100 | moltype = AA   length = 536 |
|---|---|
| FEATURE | Location/Qualifiers |
| REGION | 1..536 |
| | note = Synthetic: PaSA139V/L325W/M465I |
| source | 1..536 |
| | mol_type = protein |
| | organism = synthetic construct |

SEQUENCE: 100
```
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGIRAIRQ GDWKAVYLPA  480
PVGPATWQLY DLARDPGEIH DLADSQPGKL AELIEHWKRY VSETGVVEGA SPFLVR      536
```

| SEQ ID NO: 101 | moltype = AA   length = 536 |
|---|---|
| FEATURE | Location/Qualifiers |
| REGION | 1..536 |
| | note = Synthetic: PaSA139V/L325W/M465W |
| source | 1..536 |
| | mol_type = protein |
| | organism = synthetic construct |

SEQUENCE: 101
```
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGWRAIRQ GDWKAVYLPA  480
PVGPATWQLY DLARDPGEIH DLADSQPGKL AELIEHWKRY VSETGVVEGA SPFLVR      536
```

| SEQ ID NO: 102 | moltype = AA   length = 536 |
|---|---|
| FEATURE | Location/Qualifiers |
| REGION | 1..536 |
| | note = Synthetic: PaSA139V/L325W/M465C |
| source | 1..536 |
| | mol_type = protein |
| | organism = synthetic construct |

SEQUENCE: 102
```
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPRILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGCRAIRQ GDWKAVYLPA  480
PVGPATWQLY DLARDPGEIH DLADSQPGKL AELIEHWKRY VSETGVVEGA SPFLVR      536
```

| SEQ ID NO: 103 | moltype = AA   length = 536 |
|---|---|
| FEATURE | Location/Qualifiers |
| REGION | 1..536 |
| | note = Synthetic: PaSA139V/L325W/M465F |
| source | 1..536 |
| | mol_type = protein |
| | organism = synthetic construct |

SEQUENCE: 103

```
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPRILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGFRAIRQ GDWKAVYLPA   480
PVGPATWQLY DLARDPGEIH DLADSQPGKL AELIEHWKRY VSETGVVEGA SPFLVR       536

SEQ ID NO: 104          moltype = AA   length = 536
FEATURE                 Location/Qualifiers
REGION                  1..536
                        note = Synthetic: PaSA139V/R155E/L325W/K158V
source                  1..536
                        mol_type = protein
                        organism = synthetic construct
SEQUENCE: 104
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILVGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 105          moltype = AA   length = 536
FEATURE                 Location/Qualifiers
REGION                  1..536
                        note = Synthetic: PaSA139V/R155E/L325W/K158R
source                  1..536
                        mol_type = protein
                        organism = synthetic construct
SEQUENCE: 105
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILRGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 106          moltype = AA   length = 536
FEATURE                 Location/Qualifiers
REGION                  1..536
                        note = Synthetic: PaSA139V/R155E/L325W/K158N
source                  1..536
                        mol_type = protein
                        organism = synthetic construct
SEQUENCE: 106
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILNGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 107          moltype = AA   length = 536
FEATURE                 Location/Qualifiers
REGION                  1..536
                        note = Synthetic: PaSA139V/R155E/L325W/K158M
source                  1..536
                        mol_type = protein
                        organism = synthetic construct
SEQUENCE: 107
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILMGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
```

```
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 108             moltype = AA  length = 536
FEATURE                    Location/Qualifiers
REGION                     1..536
                           note = Synthetic: PaSA139V/R155E/L325W/K158I
source                     1..536
                           mol_type = protein
                           organism = synthetic construct
SEQUENCE: 108
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILIGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 109             moltype = AA  length = 536
FEATURE                    Location/Qualifiers
REGION                     1..536
                           note = Synthetic: PaSA139V/R155E/L325W/K158D
source                     1..536
                           mol_type = protein
                           organism = synthetic construct
SEQUENCE: 109
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILDGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 110             moltype = AA  length = 536
FEATURE                    Location/Qualifiers
REGION                     1..536
                           note = Synthetic: PaSA139V/R155E/L325W/A323Y
source                     1..536
                           mol_type = protein
                           organism = synthetic construct
SEQUENCE: 110
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGYLWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 111             moltype = AA  length = 536
FEATURE                    Location/Qualifiers
REGION                     1..536
                           note = Synthetic: PaSA139V/R155E/L325W/A323V
source                     1..536
                           mol_type = protein
                           organism = synthetic construct
SEQUENCE: 111
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGVLWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR       536

SEQ ID NO: 112             moltype = AA  length = 536
FEATURE                    Location/Qualifiers
REGION                     1..536
                           note = Synthetic: PaSA139V/R155E/L325W/A323T
```

```
source                      1..536
                            mol_type = protein
                            organism = synthetic construct
SEQUENCE: 112
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGTLWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR      536

SEQ ID NO: 113              moltype = AA   length = 536
FEATURE                     Location/Qualifiers
REGION                      1..536
                            note = Synthetic: PaSA139V/R155E/L325W/A323M
source                      1..536
                            mol_type = protein
                            organism = synthetic construct
SEQUENCE: 113
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGMLWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR      536

SEQ ID NO: 114              moltype = AA   length = 536
FEATURE                     Location/Qualifiers
REGION                      1..536
                            note = Synthetic: PaSA139V/R155E/L325W/A323L
source                      1..536
                            mol_type = protein
                            organism = synthetic construct
SEQUENCE: 114
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGLLWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR      536

SEQ ID NO: 115              moltype = AA   length = 536
FEATURE                     Location/Qualifiers
REGION                      1..536
                            note = Synthetic: PaSA139V/R155E/L325W/A323I
source                      1..536
                            mol_type = protein
                            organism = synthetic construct
SEQUENCE: 115
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGILWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGMRAIRQ GDWKAVYLPA   480
PVGPATWQLY DLARDPGEIH DLADSQPGKL AELIEHWKRY VSETGVVEGA SPFLVR      536

SEQ ID NO: 116              moltype = AA   length = 536
FEATURE                     Location/Qualifiers
REGION                      1..536
                            note = Synthetic: PaSA139V/R155E/L325W/A323F
source                      1..536
                            mol_type = protein
                            organism = synthetic construct
SEQUENCE: 116
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
```

```
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGFLWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 117           moltype = AA   length = 536
FEATURE                  Location/Qualifiers
REGION                   1..536
                         note = Synthetic: PaSA139V/R155E/L325W/A323C
source                   1..536
                         mol_type = protein
                         organism = synthetic construct
SEQUENCE: 117
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPEILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGCLWEAFPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 118           moltype = AA   length = 536
FEATURE                  Location/Qualifiers
REGION                   1..536
                         note = Synthetic: PaSA139V/R155E/L325W/F328G
source                   1..536
                         mol_type = protein
                         organism = synthetic construct
SEQUENCE: 118
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPEILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAGPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 119           moltype = AA   length = 536
FEATURE                  Location/Qualifiers
REGION                   1..536
                         note = Synthetic: PaSA139V/R155E/L325W/F328C
source                   1..536
                         mol_type = protein
                         organism = synthetic construct
SEQUENCE: 119
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPEILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEACPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536

SEQ ID NO: 120           moltype = AA   length = 536
FEATURE                  Location/Qualifiers
REGION                   1..536
                         note = Synthetic: PaSA139V/R155E/L325W/F328V
source                   1..536
                         mol_type = protein
                         organism = synthetic construct
SEQUENCE: 120
MSKRPNFLVI VADDLGFSDI GAFGGEIATP NLDALAIAGL RLTDFHTAST CSPTRSMLLT     60
GTDHHIAGIG TMAEALTPEL EGKPGYEGHL NERVVALPEL LREAGYQTLM AGKWHLGLKP    120
EQTPHARGFE RSFSLLPGVA NHYGEEPPYD ESTPEILKGT PALYVEDERY LDTLPEGFYS    180
SDAFGDKLLQ YLKERDQSRP FFAYLPFSAP HWPLQAPREI VEKYRGRYDA GPEALRQERL    240
ARLKELGLVE ADVEAHPVLA LTREWEALED EERAKSARAM EVYAAMVERM DWNIGRVVDY    300
LRRQGELDNT FVLFMSDNGA EGALWEAVPK FGPDLLGFLD RHYDNSLENI GRANSYVWYG    360
PRWAQAATAP SRLYKAFTTQ GGIRVPALVR YPRLSRQGAI SHAFATVMDV TPTLLDLAGV    420
RHPGKRWRGR EIAEPRGRSW LGWLSGETEA AHDENTVTGW ELFGMRAIRQ GDWKAVYLPA    480
PVGPATWQLY DLARDPGEIH DLADSQPGKL AELIEHWKRY VSETGVVEGA SPFLVR        536
```

| SEQ ID NO: 121 | moltype = AA length = 536 |
| --- | --- |
| FEATURE | Location/Qualifiers |
| REGION | 1..536 |
| | note = Synthetic: PaSA139V/R155E/L325W/M465W |
| source | 1..536 |
| | mol_type = protein |
| | organism = synthetic construct |

SEQUENCE: 121
```
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGWRAIRQ GDWKAVYLPA   480
PVGPATWQLY DLARDPGEIH DLADSQPGKL AELIEHWKRY VSETGVVEGA SPFLVR      536
```

| SEQ ID NO: 122 | moltype = AA length = 536 |
| --- | --- |
| FEATURE | Location/Qualifiers |
| REGION | 1..536 |
| | note = Synthetic: PaSA139V/R155E/L325W/M465V |
| source | 1..536 |
| | mol_type = protein |
| | organism = synthetic construct |

SEQUENCE: 122
```
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGVRAIRQ GDWKAVYLPA   480
PVGPATWQLY DLARDPGEIH DLADSQPGKL AELIEHWKRY VSETGVVEGA SPFLVR      536
```

| SEQ ID NO: 123 | moltype = AA length = 536 |
| --- | --- |
| FEATURE | Location/Qualifiers |
| REGION | 1..536 |
| | note = Synthetic: PaSA139V/R155E/L325W/M465S |
| source | 1..536 |
| | mol_type = protein |
| | organism = synthetic construct |

SEQUENCE: 123
```
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGSRAIRQ GDWKAVYLPA   480
PVGPATWQLY DLARDPGEIH DLADSQPGKL AELIEHWKRY VSETGVVEGA SPFLVR      536
```

| SEQ ID NO: 124 | moltype = AA length = 536 |
| --- | --- |
| FEATURE | Location/Qualifiers |
| REGION | 1..536 |
| | note = Synthetic: PaSA139V/R155E/L325W/M465Q |
| source | 1..536 |
| | mol_type = protein |
| | organism = synthetic construct |

SEQUENCE: 124
```
MSKRPNFLVI VADDLGFSDI GAFGGEIATP NLDALAIAGL RLTDFHTAST CSPTRSMLLT    60
GTDHHIAGIG TMAEALTPEL EGKPGYEGHL NERVVALPEL LREAGYQTLM AGKWHLGLKP   120
EQTPHARGFE RSFSLLPGVA NHYGEEPPYD ESTPEILKGT PALYVEDERY LDTLPEGFYS   180
SDAFGDKLLQ YLKERDQSRP FFAYLPFSAP HWPLQAPREI VEKYRGRYDA GPEALRQERL   240
ARLKELGLVE ADVEAHPVLA LTREWEALED EERAKSARAM EVYAAMVERM DWNIGRVVDY   300
LRRQGELDNT FVLFMSDNGA EGALWEAFPK FGPDLLGFLD RHYDNSLENI GRANSYVWYG   360
PRWAQAATAP SRLYKAFTTQ GGIRVPALVR YPRLSRQGAI SHAFATVMDV TPTLLDLAGV   420
RHPGKRWRGR EIAEPRGRSW LGWLSGETEA AHDENTVTGW ELFGQRAIRQ GDWKAVYLPA   480
PVGPATWQLY DLARDPGEIH DLADSQPGKL AELIEHWKRY VSETGVVEGA SPFLVR      536
```

| SEQ ID NO: 125 | moltype = AA length = 536 |
| --- | --- |
| FEATURE | Location/Qualifiers |
| REGION | 1..536 |
| | note = Synthetic: PaSA139V/R155E/L325W/M465I |
| source | 1..536 |
| | mol_type = protein |
| | organism = synthetic construct |

```
SEQUENCE: 125
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPEILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGIRAIRQ GDWKAVYLPA  480
PVGPATWQLY DLARDPGEIH DLADSQPGKL AELIEHWKRY VSETGVVEGA SPFLVR     536

SEQ ID NO: 126          moltype = AA  length = 536
FEATURE                 Location/Qualifiers
REGION                  1..536
                        note = Synthetic: PaSA139V/R155E/L325W/M465E
source                  1..536
                        mol_type = protein
                        organism = synthetic construct
SEQUENCE: 126
MSKRPNFLVI VADDLGFSDI GAFGGEIATP NLDALAIAGL RLTDFHTAST CSPTRSMLLT   60
GTDHHIAGIG TMAEALTPEL EGKPGYEGHL NERVVALPEL LREAGYQTLM AGKWHLGLKP  120
EQTPHARGFE RSFSLLPGVA NHYGEEPPYD ESTPEILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGERAIRQ GDWKAVYLPA  480
PVGPATWQLY DLARDPGEIH DLADSQPGKL AELIEHWKRY VSETGVVEGA SPFLVR     536

SEQ ID NO: 127          moltype = AA  length = 536
FEATURE                 Location/Qualifiers
REGION                  1..536
                        note = Synthetic: PaSA139V/R155E/L325W/A75R
source                  1..536
                        mol_type = protein
                        organism = synthetic construct
SEQUENCE: 127
MSKRPNFLVI VADDLGFSDI GAFGGEIATP NLDALAIAGL RLTDFHTAST CSPTRSMLLT   60
GTDHHIAGIG TMAERLTPEL EGKPGYEGHL NERVVALPEL LREAGYQTLM AGKWHLGLKP  120
EQTPHARGFE RSFSLLPGVA NHYGEEPPYD ESTPEILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR     536

SEQ ID NO: 128          moltype = AA  length = 536
FEATURE                 Location/Qualifiers
REGION                  1..536
                        note = Synthetic: PaSA139V/R155E/L325W/A75Q
source                  1..536
                        mol_type = protein
                        organism = synthetic construct
SEQUENCE: 128
MSKRPNFLVI VADDLGFSDI GAFGGEIATP NLDALAIAGL RLTDFHTAST CSPTRSMLLT   60
GTDHHIAGIG TMAEQLTPEL EGKPGYEGHL NERVVALPEL LREAGYQTLM AGKWHLGLKP  120
EQTPHARGFE RSFSLLPGVA NHYGEEPPYD ESTPEILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
PRWAQAATAP SRLYKAFTTQ GGIRVPALVR YPRLSRQGAI SHAFATVMDV TPTLLDLAGV  420
RHPGKRWRGR EIAEPRGRSW LGWLSGETEA AHDENTVTGW ELFGMRAIRQ GDWKAVYLPA  480
PVGPATWQLY DLARDPGEIH DLADSQPGKL AELIEHWKRY VSETGVVEGA SPFLVR     536

SEQ ID NO: 129          moltype = AA  length = 536
FEATURE                 Location/Qualifiers
REGION                  1..536
                        note = Synthetic: PaSA139V/R155E/L325W/A75H
source                  1..536
                        mol_type = protein
                        organism = synthetic construct
SEQUENCE: 129
MSKRPNFLVI VADDLGFSDI GAFGGEIATP NLDALAIAGL RLTDFHTAST CSPTRSMLLT   60
GTDHHIAGIG TMAEHLTPEL EGKPGYEGHL NERVVALPEL LREAGYQTLM AGKWHLGLKP  120
EQTPHARGFE RSFSLLPGVA NHYGEEPPYD ESTPEILKGT PALYVEDERY LDTLPEGFYS  180
SDAFGDKLLQ YLKERDQSRP FFAYLPFSAP HWPLQAPREI VEKYRGRYDA GPEALRQERL  240
ARLKELGLVE ADVEAHPVLA LTREWEALED EERAKSARAM EVYAAMVERM DWNIGRVVDY  300
LRRQGELDNT FVLFMSDNGA EGALWEAFPK FGPDLLGFLD RHYDNSLENI GRANSYVWYG  360
```

```
PRWAQAATAP  SRLYKAFTTQ  GGIRVPALVR  YPRLSRQGAI  SHAFATVMDV  TPTLLDLAGV   420
RHPGKRWRGR  EIAEPRGRSW  LGWLSGETEA  AHDENTVTGW  ELFGMRAIRQ  GDWKAVYLPA   480
PVGPATWQLY  DLARDPGEIH  DLADSQPGKL  AELIEHWKRY  VSETGVVEGA  SPFLVR       536

SEQ ID NO: 130          moltype = AA   length = 536
FEATURE                 Location/Qualifiers
REGION                  1..536
                        note = Synthetic: PaSA139V/R155E/L325W/A75G
source                  1..536
                        mol_type = protein
                        organism = synthetic construct
SEQUENCE: 130
MSKRPNFLVI  VADDLGFSDI  GAFGGEIATP  NLDALAIAGL  RLTDFHTAST  CSPTRSMLLT    60
GTDHHIAGIG  TMAEGLTPEL  EGKPGYEGHL  NERVVALPEL  LREAGYQTLM  AGKWHLGLKP   120
EQTPHARGFE  RSFSLLPGVA  NHYGEEPPYD  ESTPEILKGT  PALYVEDERY  LDTLPEGFYS   180
SDAFGDKLLQ  YLKERDQSRP  FFAYLPFSAP  HWPLQAPREI  VEKYRGRYDA  GPEALRQERL   240
ARLKELGLVE  ADVEAHPVLA  LTREWEALED  EERAKSARAM  EVYAAMVERM  DWNIGRVVDY   300
LRRQGELDNT  FVLFMSDNGA  EGALWEAFPK  FGPDLLGFLD  RHYDNSLENI  GRANSYVWYG   360
PRWAQAATAP  SRLYKAFTTQ  GGIRVPALVR  YPRLSRQGAI  SHAFATVMDV  TPTLLDLAGV   420
RHPGKRWRGR  EIAEPRGRSW  LGWLSGETEA  AHDENTVTGW  ELFGMRAIRQ  GDWKAVYLPA   480
PVGPATWQLY  DLARDPGEIH  DLADSQPGKL  AELIEHWKRY  VSETGVVEGA  SPFLVR       536

SEQ ID NO: 131          moltype = AA   length = 536
FEATURE                 Location/Qualifiers
REGION                  1..536
                        note = Synthetic: PaSA139V/R155E/L325W/A75F
source                  1..536
                        mol_type = protein
                        organism = synthetic construct
SEQUENCE: 131
MSKRPNFLVI  VADDLGFSDI  GAFGGEIATP  NLDALAIAGL  RLTDFHTAST  CSPTRSMLLT    60
GTDHHIAGIG  TMAEFLTPEL  EGKPGYEGHL  NERVVALPEL  LREAGYQTLM  AGKWHLGLKP   120
EQTPHARGFE  RSFSLLPGVA  NHYGEEPPYD  ESTPEILKGT  PALYVEDERY  LDTLPEGFYS   180
SDAFGDKLLQ  YLKERDQSRP  FFAYLPFSAP  HWPLQAPREI  VEKYRGRYDA  GPEALRQERL   240
ARLKELGLVE  ADVEAHPVLA  LTREWEALED  EERAKSARAM  EVYAAMVERM  DWNIGRVVDY   300
LRRQGELDNT  FVLFMSDNGA  EGALWEAFPK  FGPDLLGFLD  RHYDNSLENI  GRANSYVWYG   360
PRWAQAATAP  SRLYKAFTTQ  GGIRVPALVR  YPRLSRQGAI  SHAFATVMDV  TPTLLDLAGV   420
RHPGKRWRGR  EIAEPRGRSW  LGWLSGETEA  AHDENTVTGW  ELFGMRAIRQ  GDWKAVYLPA   480
PVGPATWQLY  DLARDPGEIH  DLADSQPGKL  AELIEHWKRY  VSETGVVEGA  SPFLVR       536

SEQ ID NO: 132          moltype = AA   length = 536
FEATURE                 Location/Qualifiers
REGION                  1..536
                        note = Synthetic: PaSA139V/R155E/T160S/L325W
source                  1..536
                        mol_type = protein
                        organism = synthetic construct
SEQUENCE: 132
MSKRPNFLVI  VADDLGFSDI  GAFGGEIATP  NLDALAIAGL  RLTDFHTAST  CSPTRSMLLT    60
GTDHHIAGIG  TMAEALTPEL  EGKPGYEGHL  NERVVALPEL  LREAGYQTLM  AGKWHLGLKP   120
EQTPHARGFE  RSFSLLPGVA  NHYGEEPPYD  ESTPEILKGS  PALYVEDERY  LDTLPEGFYS   180
SDAFGDKLLQ  YLKERDQSRP  FFAYLPFSAP  HWPLQAPREI  VEKYRGRYDA  GPEALRQERL   240
ARLKELGLVE  ADVEAHPVLA  LTREWEALED  EERAKSARAM  EVYAAMVERM  DWNIGRVVDY   300
LRRQGELDNT  FVLFMSDNGA  EGALWEAFPK  FGPDLLGFLD  RHYDNSLENI  GRANSYVWYG   360
PRWAQAATAP  SRLYKAFTTQ  GGIRVPALVR  YPRLSRQGAI  SHAFATVMDV  TPTLLDLAGV   420
RHPGKRWRGR  EIAEPRGRSW  LGWLSGETEA  AHDENTVTGW  ELFGMRAIRQ  GDWKAVYLPA   480
PVGPATWQLY  DLARDPGEIH  DLADSQPGKL  AELIEHWKRY  VSETGVVEGA  SPFLVR       536

SEQ ID NO: 133          moltype = AA   length = 536
FEATURE                 Location/Qualifiers
REGION                  1..536
                        note = Synthetic: PaSA139V/R155E/T160S/L325W/A75G
source                  1..536
                        mol_type = protein
                        organism = synthetic construct
SEQUENCE: 133
MSKRPNFLVI  VADDLGFSDI  GAFGGEIATP  NLDALAIAGL  RLTDFHTAST  CSPTRSMLLT    60
GTDHHIAGIG  TMAEGLTPEL  EGKPGYEGHL  NERVVALPEL  LREAGYQTLM  AGKWHLGLKP   120
EQTPHARGFE  RSFSLLPGVA  NHYGEEPPYD  ESTPEILKGS  PALYVEDERY  LDTLPEGFYS   180
SDAFGDKLLQ  YLKERDQSRP  FFAYLPFSAP  HWPLQAPREI  VEKYRGRYDA  GPEALRQERL   240
ARLKELGLVE  ADVEAHPVLA  LTREWEALED  EERAKSARAM  EVYAAMVERM  DWNIGRVVDY   300
LRRQGELDNT  FVLFMSDNGA  EGALWEAFPK  FGPDLLGFLD  RHYDNSLENI  GRANSYVWYG   360
PRWAQAATAP  SRLYKAFTTQ  GGIRVPALVR  YPRLSRQGAI  SHAFATVMDV  TPTLLDLAGV   420
RHPGKRWRGR  EIAEPRGRSW  LGWLSGETEA  AHDENTVTGW  ELFGMRAIRQ  GDWKAVYLPA   480
PVGPATWQLY  DLARDPGEIH  DLADSQPGKL  AELIEHWKRY  VSETGVVEGA  SPFLVR       536
```